US012168087B2

(12) United States Patent
Min et al.

(10) Patent No.: US 12,168,087 B2
(45) Date of Patent: Dec. 17, 2024

(54) COLLECTION, GENOME EDITING, AND WASHING OF T-CELL LYMPHOCYTES

(71) Applicant: Fenwal, Inc., Lake Zurich, IL (US)

(72) Inventors: Kyungyoon Min, Kildeer, IL (US); Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 1325 days.

(21) Appl. No.: 16/807,254

(22) Filed: Mar. 3, 2020

(65) Prior Publication Data

US 2020/0282116 A1 Sep. 10, 2020

Related U.S. Application Data

(60) Provisional application No. 62/814,050, filed on Mar. 5, 2019.

(51) Int. Cl.
| | |
|---|---|
| *C12N 5/078* | (2010.01) |
| *A61K 35/17* | (2015.01) |
| *A61M 1/02* | (2006.01) |
| *A61M 1/34* | (2006.01) |
| *A61M 1/36* | (2006.01) |
| *A61M 1/38* | (2006.01) |
| *C12M 1/00* | (2006.01) |
| *C12M 1/42* | (2006.01) |
| *C12N 5/00* | (2006.01) |
| *C12N 5/0783* | (2010.01) |
| *C12N 5/10* | (2006.01) |
| *C12N 13/00* | (2006.01) |
| *C12N 15/85* | (2006.01) |

(52) U.S. Cl.
CPC ........ *A61M 1/0281* (2013.01); *A61M 1/0218* (2014.02); *A61M 1/0231* (2014.02); *A61M 1/362227* (2022.05); *A61M 1/36224* (2022.05); *A61M 1/36225* (2022.05); *A61M 1/362261* (2022.05); *A61M 1/362265* (2022.05); *A61M 1/3696* (2014.02); *C12M 35/02* (2013.01); *C12M 45/05* (2013.01); *C12N 5/0087* (2013.01); *C12N 5/10* (2013.01); *C12N 13/00* (2013.01); *A61M 2202/0411* (2013.01); *A61M 2205/3303* (2013.01); *A61M 2206/16* (2013.01)

(58) Field of Classification Search
None
See application file for complete search history.

(56) References Cited

U.S. PATENT DOCUMENTS

| | | | |
|---|---|---|---|
| 5,194,145 A | 3/1993 | Schoendorfer | |
| 5,360,542 A | 11/1994 | Willamson et al. | |
| 5,632,893 A | 5/1997 | Brown et al. | |
| 5,720,921 A * | 2/1998 | Meserol | A61M 1/34 |
| | | | 435/173.6 |
| 5,868,696 A | 2/1999 | Giesler et al. | |
| 5,980,760 A | 11/1999 | Min et al. | |
| 6,027,657 A | 2/2000 | Min et al. | |
| 6,419,822 B2 | 7/2002 | Muller et al. | |
| 6,471,855 B1 | 10/2002 | Odak et al. | |
| 6,569,112 B2 | 5/2003 | Strahilevitz | |
| 6,579,219 B2 | 6/2003 | Dolecek et al. | |
| 6,582,386 B2 | 6/2003 | Min et al. | |
| 6,629,919 B2 | 10/2003 | Egozy et al. | |
| 6,706,008 B2 | 3/2004 | Vishnoi et al. | |
| 6,770,883 B2 | 8/2004 | McNeal et al. | |
| 6,808,503 B2 | 10/2004 | Farrell et al. | |
| 6,866,826 B2 | 3/2005 | Moore et al. | |
| 6,884,228 B2 | 4/2005 | Brown et al. | |
| 7,049,622 B1 | 5/2006 | Weiss | |
| 7,081,082 B2 | 7/2006 | Scholz et al. | |
| 7,150,834 B2 | 12/2006 | Mueth et al. | |
| 7,186,230 B2 | 3/2007 | Briggs et al. | |
| 7,186,231 B2 | 3/2007 | Takagi et al. | |
| 7,211,037 B2 | 5/2007 | Briggs et al. | |

(Continued)

FOREIGN PATENT DOCUMENTS

| | | |
|---|---|---|
| EP | 1946784 B1 | 10/2012 |
| EP | 2720730 B1 | 1/2017 |

(Continued)

OTHER PUBLICATIONS

Ulrike Mock et al.: "Automated Manufacturing of Chimeric Antigen Receptor T Cells for Adoptive Immunotherapy Using CliniMACS Prodigy", Cytotherapy, vol. 18, No. 8, Aug. 1, 2016 (Aug. 1, 2016), pp. 1002-1011.

(Continued)

*Primary Examiner* — Maria Marvich
(74) *Attorney, Agent, or Firm* — Cook Alex Ltd.

(57) ABSTRACT

Blood from a blood source is drawn into a fluid flow circuit. A mononuclear cell product is separated from the blood, followed by at least a portion of the mononuclear cell product being conveyed into an electroporation device without disconnecting the blood source from the fluid flow circuit. The electroporation device opens pores in a membrane of at least one of the cells of the mononuclear cell product to allow DNA material (which is added to the mononuclear cell product prior to electroporation) to enter and modify the genome of the cell. At least a portion of the modified mononuclear cell product is returned to the blood source. The mononuclear cell product may be washed prior to being conveyed into the electroporation device. The modified mononuclear cell product may be washed after exiting the electroporation device.

11 Claims, 32 Drawing Sheets

(56) References Cited

U.S. PATENT DOCUMENTS

| | | |
|---|---|---|
| 7,294,513 B2 | 11/2007 | Wyatt |
| 7,347,948 B2 | 3/2008 | Dolecek et al. |
| 7,354,515 B2 | 4/2008 | Coull et al. |
| 7,381,291 B2 | 6/2008 | Tobe et al. |
| 7,422,693 B2 | 9/2008 | Carter et al. |
| 7,485,084 B2 | 2/2009 | Borgstrom et al. |
| 7,563,376 B2 | 7/2009 | Oishi |
| 7,648,639 B2 | 1/2010 | Holmes et al. |
| 7,806,845 B2 | 10/2010 | Arm et al. |
| 7,906,771 B2 | 3/2011 | Carter et al. |
| 7,951,059 B2 | 5/2011 | Sweat |
| 8,057,377 B2 | 11/2011 | Holmes et al. |
| 8,075,468 B2 | 12/2011 | Min et al. |
| 8,163,276 B2 | 4/2012 | Hedrick et al. |
| 8,287,742 B2 | 10/2012 | Holmes |
| 8,317,672 B2 | 11/2012 | Nash et al. |
| 8,337,379 B2 | 12/2012 | Fletcher et al. |
| 8,535,210 B2 | 9/2013 | Kolenbrander et al. |
| 8,556,793 B2 | 10/2013 | Foley et al. |
| 8,758,211 B2 | 6/2014 | Nash et al. |
| 8,974,362 B2 | 3/2015 | Nash et al. |
| 9,011,687 B2 | 4/2015 | Swift et al. |
| 9,156,039 B2 | 10/2015 | Holmes et al. |
| 9,302,042 B2 | 4/2016 | Pages |
| 9,302,276 B2 | 4/2016 | Pesetsky et al. |
| 9,370,615 B2 | 6/2016 | Ragusa et al. |
| 9,399,182 B2 | 7/2016 | Pesetsky et al. |
| 9,550,016 B2 | 1/2017 | Gifford |
| 9,610,590 B2 | 4/2017 | Hamandi |
| 9,789,235 B2 | 10/2017 | Gifford et al. |
| 10,086,128 B2 | 10/2018 | Kyle et al. |
| 10,166,322 B2 | 1/2019 | Sweat et al. |
| 10,238,787 B2 | 3/2019 | Takuwa |
| 10,293,097 B2 | 5/2019 | Murphy et al. |
| 10,399,881 B2 | 9/2019 | Donais et al. |
| 10,493,467 B2 | 12/2019 | Lundquist et al. |
| 10,518,007 B2 | 12/2019 | Kimura |
| 10,561,783 B2 | 2/2020 | Hamandi et al. |
| 2002/0128583 A1 | 9/2002 | Min et al. |
| 2004/0195190 A1 | 10/2004 | Min et al. |
| 2009/0215602 A1 | 8/2009 | Min et al. |
| 2011/0003675 A1 | 1/2011 | Dolecek |
| 2011/0104128 A1 | 5/2011 | Cooper et al. |
| 2011/0294641 A1 | 12/2011 | Dolecek et al. |
| 2013/0197419 A1 | 8/2013 | Min et al. |
| 2014/0370491 A1 | 12/2014 | Radwanski |
| 2014/0378292 A1 | 12/2014 | Igarashi |
| 2015/0060363 A1* | 3/2015 | Kusters ............... A61M 1/0218 |
| | | 210/651 |
| 2015/0068959 A1 | 3/2015 | Zheng |
| 2015/0104824 A1 | 4/2015 | Walker et al. |
| 2015/0218517 A1 | 8/2015 | Kusters et al. |
| 2015/0367063 A1 | 12/2015 | Kimura |
| 2017/0153431 A1 | 6/2017 | Nguyen et al. |
| 2017/0197023 A1 | 7/2017 | Radwanski et al. |
| 2018/0043374 A1 | 2/2018 | Meinig et al. |
| 2018/0164141 A1 | 6/2018 | Bordignon et al. |
| 2018/0185772 A1 | 7/2018 | Karhiniemi et al. |
| 2019/0003873 A1 | 1/2019 | Araujo et al. |
| 2019/0030545 A1 | 1/2019 | Hamada et al. |
| 2019/0083696 A1 | 3/2019 | Igarashi |
| 2021/0244871 A1* | 8/2021 | Peritt ..................... A61P 35/00 |

FOREIGN PATENT DOCUMENTS

| | | |
|---|---|---|
| WO | WO 2010/075061 A2 | 7/2010 |
| WO | WO2012/091720 A1 | 7/2012 |
| WO | WO 2012/125457 A1 | 9/2012 |
| WO | WO 2012/141697 A1 | 10/2012 |
| WO | WO 2013/043433 A2 | 3/2013 |
| WO | WO 2014/039091 A1 | 3/2014 |
| WO | WO 2018/015561 A1 | 1/2018 |
| WO | WO 2018/053217 A1 | 3/2018 |
| WO | WO2018/154115 A2 | 8/2018 |
| WO | WO 2019/046766 A2 | 3/2019 |
| WO | WO2019/047498 A1 | 3/2019 |
| WO | WO2019/165478 A1 | 8/2019 |
| WO | WO 2019/217964 A1 | 11/2019 |
| WO | WO2020/002059 A1 | 1/2020 |
| WO | WO2020/055958 A1 | 3/2020 |
| WO | WO 2020/123649 A1 | 6/2020 |

OTHER PUBLICATIONS

Bruce L. Levine et al.: "Global Manufacturing of CAR T Cell Therapy", Molecular Therapy—Methods & Clinical Development, vol. 4, Mar. 4, 2017 (Mar. 4, 2017), pp. 92-101.

* cited by examiner

COLLECTION, GENOME EDITING, AND WASHING OF T-CELL LYMPHOCYTES

CROSS-REFERENCE TO RELATED APPLICATIONS

This application claims the benefit of and priority of U.S. Provisional Patent Application Ser. No. 62/814,050, filed Mar. 5, 2019, the contents of which are incorporated by reference herein.

BACKGROUND

Field of the Disclosure

The present disclosure relates to collection of mononuclear cells ("MNCs") and T-cell lymphocytes. More particularly, the present disclosure relates to the collection, genome editing, and washing of T-cell lymphocytes.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber.

An exemplary method of centrifugally separating and collecting MNCs including T-cell lymphocytes) is described in U.S. Pat. No. 5,980,760, which is incorporated herein by reference. In such a procedure, whole blood in a centrifuge is separated into platelet-poor plasma, an interface or MNC-containing layer, and packed red blood cells. The platelet-poor plasma is collected for later use, while the packed red blood cells are returned to the blood source and the MNC-containing layer remains in the centrifuge. When a target amount of platelet-poor plasma has been collected, an MNC accumulation phase begins. During this phase, the position of the interface within the centrifuge is moved closer to the low-G wall, such that platelet-rich plasma and packed red blood cells are removed from the centrifuge while the MNC-containing layer continues to build up in the centrifuge. Portions of the platelet-rich plasma and the packed red blood cells are returned to the blood source, with the remainder of the platelet-rich plasma and packed red blood cells being recirculated through the centrifuge to maintain a proper hematocrit.

When a certain amount of blood has been processed, the return and recirculation of the packed red blood cells is ended and a red blood cell collection phase begins. During this phase, recirculation and return of the platelet-rich plasma continues, while the packed red blood cells are conveyed from the centrifuge via an outlet port to a red blood cell collection container for later use.

When a target amount of packed red blood cells has been collected, an MNC harvest phase begins. To harvest the MNCs in the MNC-containing layer, the packed red blood cells are temporarily prevented from exiting the centrifuge. At least a portion of the collected red blood cells is conveyed into the centrifuge via the same inlet port by which whole blood had previously been flowing into the centrifuge, which forces the MNC-containing layer to exit the centrifuge via the same outlet as the platelet-rich plasma. The platelet-rich plasma exiting the centrifuge ahead of the MNC-containing layer is directed into the platelet-poor plasma container, with the MNC-containing layer subsequently being directed into an MNC collection container.

Following the MNC harvest phase, a plasma flush phase begins. During this phase, plasma from the platelet-poor plasma container is used to flush any MNC-containing layer positioned between the separation chamber and the MNC collection container back into the separation chamber. The MNC-containing layer flushed back into the separation chamber may be subsequently collected by repeating the various phases, until a target amount of MNC product has been collected.

Following collection, the MNC product may be treated to further processing, including electroporation-based treatment, such as chimeric antigen receptor ("CAR") T-cell therapy. CAR T-cell therapy includes employing electroporation to open the pores of a cell membrane, which allows DNA to enter and modify the genome of a T-cell, such as in a way that will help aid the cell in targeting cancer cells when reinfused into a patient. Typically, the MNC product is subjected to CAR T-cell therapy at a different location than the location in which the MNC product is collected, which requires disconnection of the patient from the apheresis device and subsequent reconnection of the patient for reinfusion (if the blood source is the same patient receiving the genetically modified T-cells), with a possibly significant delay between blood draw and reinfusion. Transporting the MNC product between the locations may also be expensive.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing system includes a separation device, an electroporation device, a pump assembly including a plurality of pumps, and a controller. The controller is configured to actuate the pump assembly to convey blood from a blood source into the separation device, actuate the separation device to separate a mononuclear cell product from the blood, actuate the pump assembly to convey at least a portion of the mononuclear cell product into the electroporation device to modify a genome of at least one of the cells of the mononuclear cell product, and actuate the pump assembly to convey at least a portion of the modified mononuclear cell product to the blood source.

In another aspect, a method is provided for processing blood. The method includes drawing blood from a blood source into a fluid flow circuit and separating a mononuclear cell product from the blood. At least a portion of the mononuclear cell product is conveyed into an electroporation device without disconnecting the blood source from the fluid flow circuit to modify a genome of at least one of the cells of the mononuclear cell product. At least a portion of the modified mononuclear cell product is returned to the blood source.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
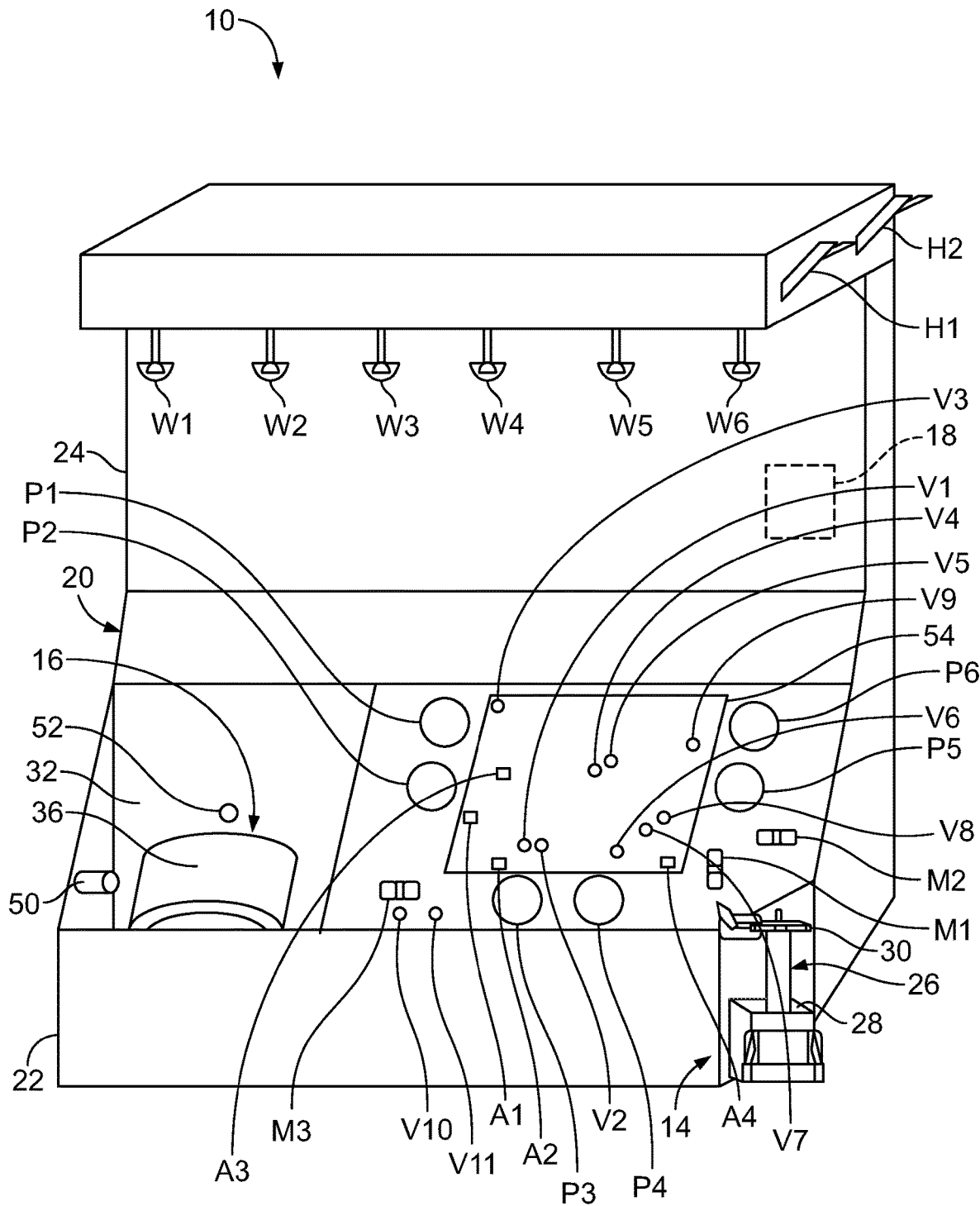
FIG. 1 is a perspective view of an exemplary blood separation device that comprises a component of a blood separation system according to an aspect of the present disclosure.
Figure 2:
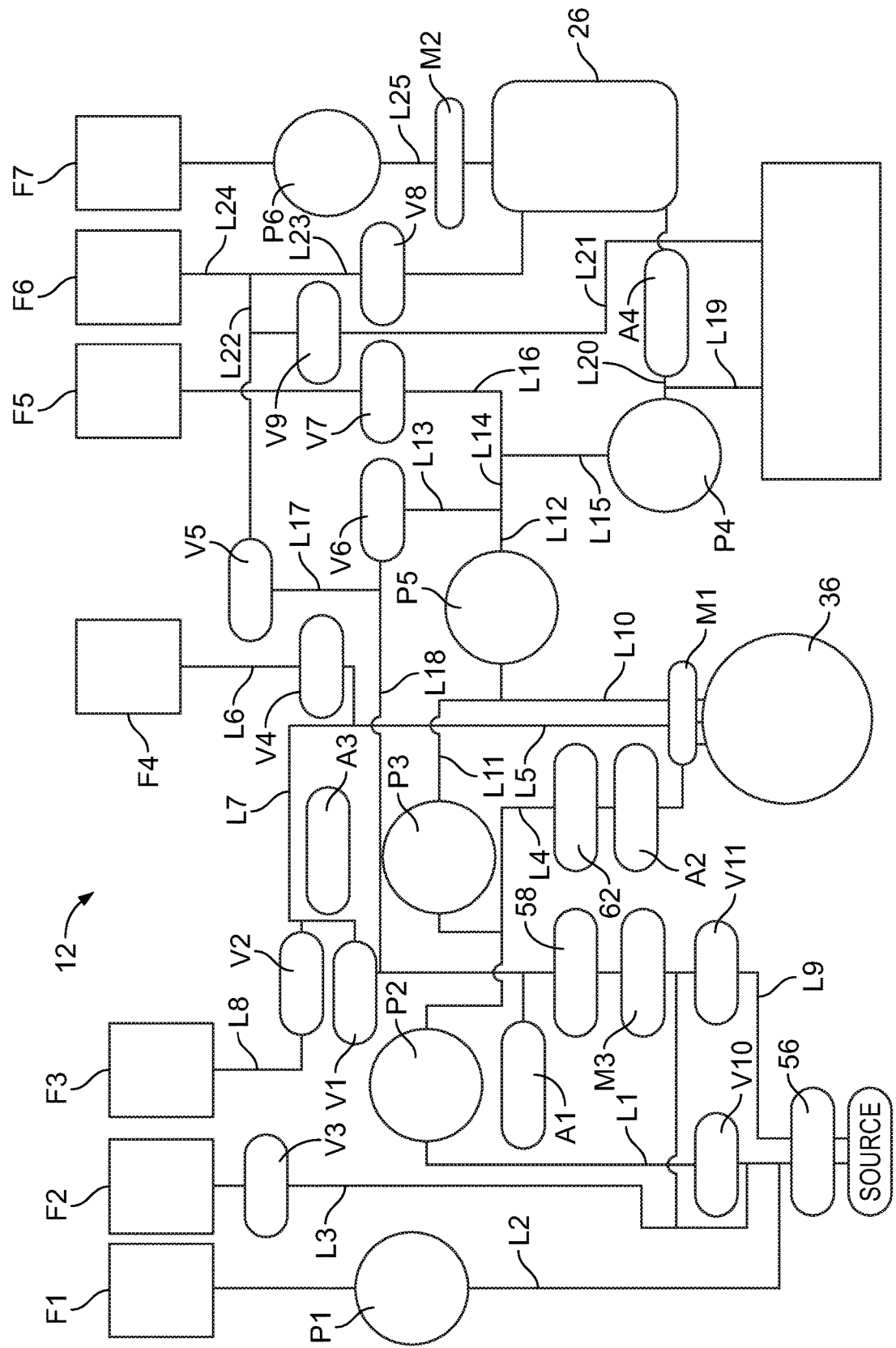
FIG. 2 is a schematic view of an exemplary disposable fluid flow circuit that may be mounted to the blood separation device of FIG. 1 to complete a blood separation system according to an aspect of the present disclosure.
Figure 58:
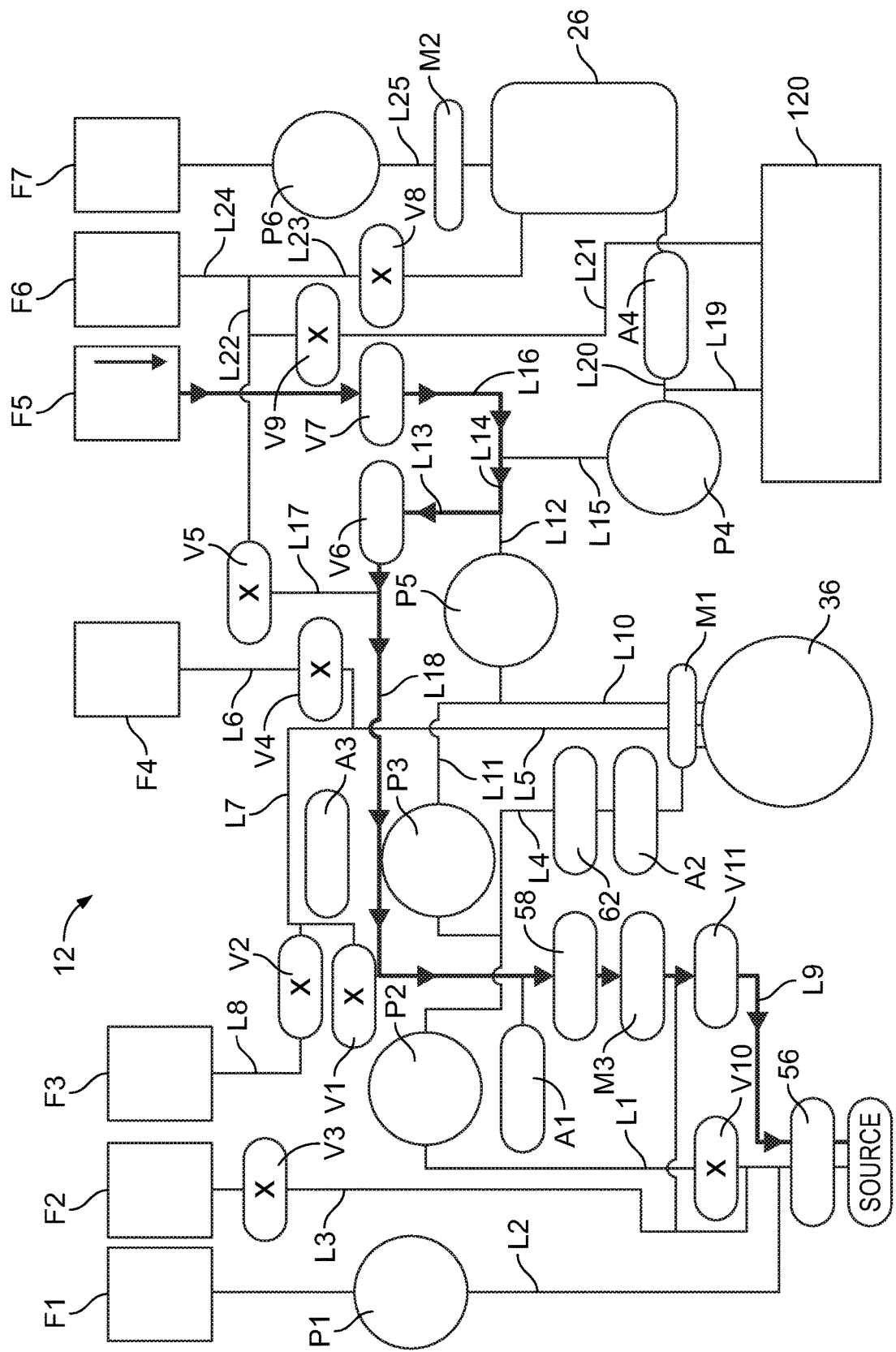

FIGS. 1-58 show components of a blood or fluid separation system that embodies various aspects of the present subject matter. Generally speaking, the system includes two principal components, a durable and reusable blood separation device 10 (FIG. 1) and a disposable fluid flow circuit 12 (FIG. 2). The blood separation device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the blood separation device 10 to perform a blood processing and collection procedure selected by the operator, as will be described in greater detail I. The Durable Blood Separation Device The blood separation device 10 (FIG. 1) is configured as a durable item that is capable of long-term use. It should be understood that the blood separation device 10 of FIG. 1 is merely exemplary of one possible configuration and that blood separation devices according to the present disclosure may be differently configured.

In the illustrated embodiment, the blood separation device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24. The configuration and operation of the spinning membrane separator drive unit 14, the centrifugal separator 16, the controller 18, and selected other components of the blood separation device 10 will be described in greater detail.

In the illustrated embodiment, the generally horizontal portion 22 is intended to rest on an elevated, generally horizontal support surface (e.g., a countertop or a tabletop), but it is also within the scope of the present disclosure for the case 20 to include a support base to allow the case 20 to be appropriately positioned and oriented when placed onto a floor or ground surface. It is also within the scope of the present disclosure for the case 20 to be mounted to a generally vertical surface (e.g., a wall), by either fixedly or removably securing the generally vertical portion 24 of the case 20 to the surface.

The case 20 may be configured to assume only the position or configuration of FIG. 1 or may be configured to move between two or more positions or configurations. For example, in one embodiment, the generally horizontal and vertical portions 22 and 24 are joined by a hinge or pivot, which allows the case 20 to be moved between a functional or open configuration (FIG. 1) in which the generally vertical portion 24 is oriented at approximately 90 degrees to the generally horizontal portion 22 and a transport or closed configuration in which the generally vertical portion 24 is rotated about the hinge to approach the generally horizontal portion 22. In such a reconfigurable embodiment, the generally vertical portion 24 may be considered to be the lid of the case 20, while the generally horizontal portion 22 may be considered to be the base. If the case 20 is so reconfigurable, then it may include a latch for releasably locking the case 20 in its closed configuration and/or a handle, which the operator can grasp for transporting the case 20 in its closed configuration.

While it may be advantageous for the blood separation device 10 to be embodied in a compact, portable case 20, it is also within the scope of the present disclosure for the blood separation device to be embodied in a larger case or fixture that is intended to be installed in a single location and remain in that location for an extended period of time. If the blood separation device is provided as a fixture, it may be provided with more components and functionality than a more portable version.

A. Spinning Membrane Separator Drive Unit

The illustrated blood separation device 10 includes a spinner support or spinning membrane separator drive unit 14 (FIG. 1) for accommodating a generally cylindrical spinning membrane separator 26 of the fluid flow circuit 12. U.S. Pat. No. 5,194,145 describes an exemplary spinning membrane separator drive unit that would be suitable for incorporation into the blood separation device 10, but it should be understood that the spinning membrane separator drive unit 14 may be differently configured without departing from the scope of the present disclosure.

The illustrated spinning membrane separator drive unit 14 has a base 28 configured to receive a lower portion of the spinning membrane separator 26 and an upper end cap 30 to receive an upper portion of the spinning membrane separator 26. Preferably, the upper end cap 30 is positioned directly above the base 28 to orient a spinning membrane separator 26 received by the spinning membrane separator drive unit 14 vertically and to define a vertical axis about which the spinning membrane separator 26 is spun. While it may be advantageous for the spinning membrane separator drive unit 14 to vertically orient a spinning membrane separator 26, it is also within the scope of the present disclosure for the spinning membrane separator 26 to be differently oriented when mounted to the blood separation device 10.

In one embodiment, one of the components of the spinning membrane separator drive unit 14 is movable with respect to the other component, which may allow differently sized spinning membrane separators 26 to be received by the spinning membrane separator drive unit 14. For example, the upper end cap 30 may be translated vertically with respect to the base 28 and locked in a plurality of different positions, with each locking position corresponding to a differently sized spinning membrane separator 26.

At least one of the base 28 and the upper end cap 30 is configured to spin one or more components of the spinning membrane separator 26 about the axis defined by the spinning membrane separator drive unit 14. The mechanism by which the spinning membrane separator drive unit 14 spins one or more components of the spinning membrane separator 26 may vary without departing from the scope of the present disclosure. In one embodiment, a component of the spinning membrane separator 26 to be spun includes at least one element configured to be acted upon by a magnet (e.g., a metallic material), while the spinning membrane separator drive unit 14 includes a magnet (e.g., a series of magnetic coils or semi-circular arcs). By modulating the magnetic field acting upon the aforementioned element of the spinning membrane separator 26, the component or components of the spinning membrane separator 26 may be made to spin in different directions and at varying speeds. In other embodiments, different mechanisms may be employed to spin the component or components of the spinning membrane separator 26.

Regardless of the mechanism by which the spinning membrane separator drive unit 14 spins the component or components of the spinning membrane separator 26, the component or components of the spinning membrane separator 26 is preferably spun at a speed that is sufficient to create Taylor vortices in a gap between the spinning component and a stationary component of the spinning membrane separator 26 (or a component that spins at a different speed). Fluid to be separated within the spinning membrane separator 26 flows through this gap, and filtration may be dramatically improved by the creation of Taylor vortices.

B. Centrifugal Separator

Figure 3:
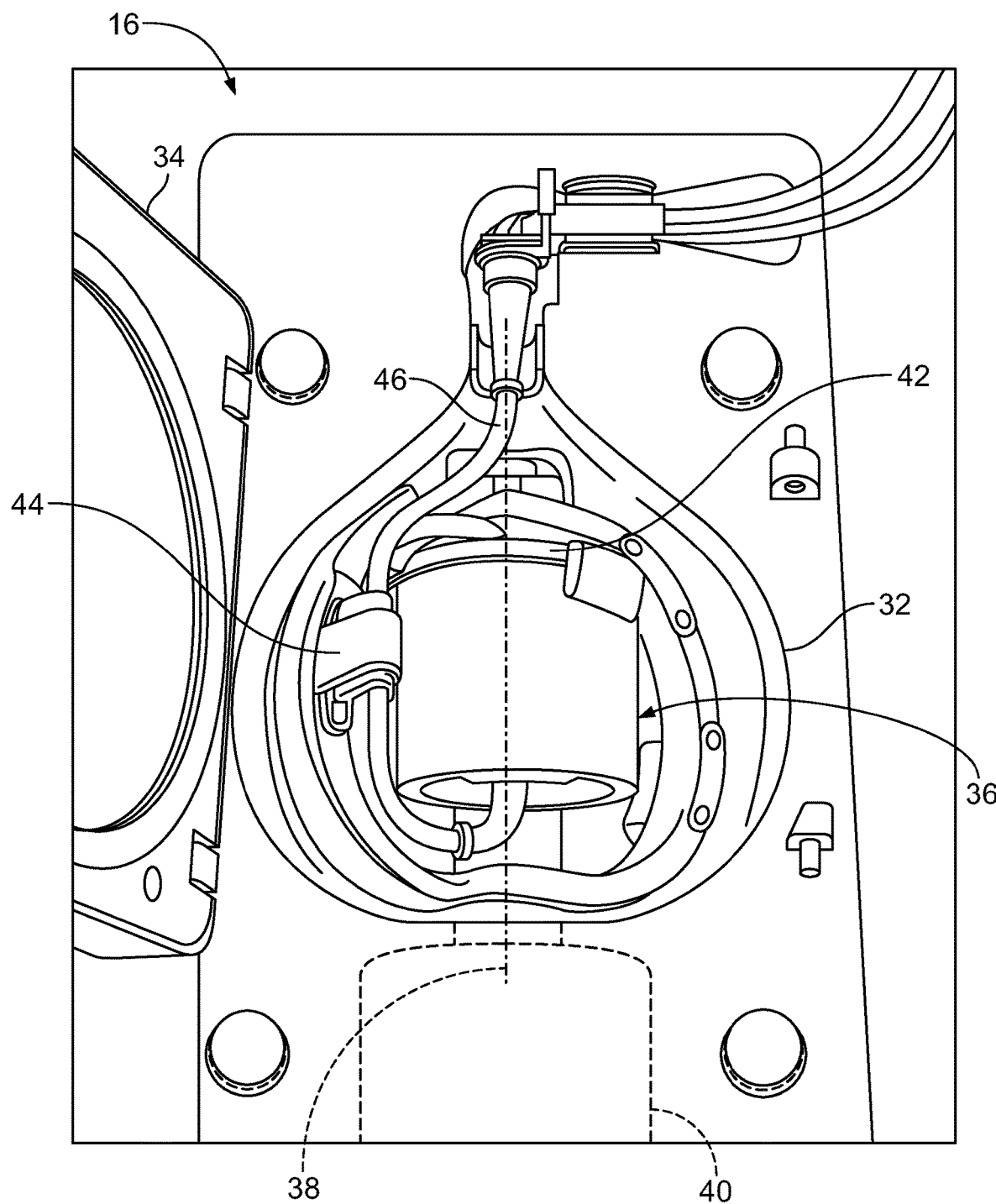
FIG. 3 is a perspective view of an exemplary centrifugal separator of the blood separation device of FIG. 1, with the centrifugal separation chamber of a fluid flow circuit mounted therein.

As for the centrifugal separator 16, it includes a centrifuge compartment 32 that may receive the other components of the centrifugal separator 16 (FIG. 3). The centrifuge compartment 32 may include a lid 34 that is opened to insert and remove a centrifugal separation chamber 36 of the fluid flow circuit 12. During a separation procedure, the lid 34 may be closed with the centrifugal separation chamber 36 positioned within the centrifuge compartment 32, as the centrifugal separation chamber 36 is spun or rotated about an axis 38 under the power of an electric drive motor or rotor 40 of the centrifugal separator 16.

Figure 4:
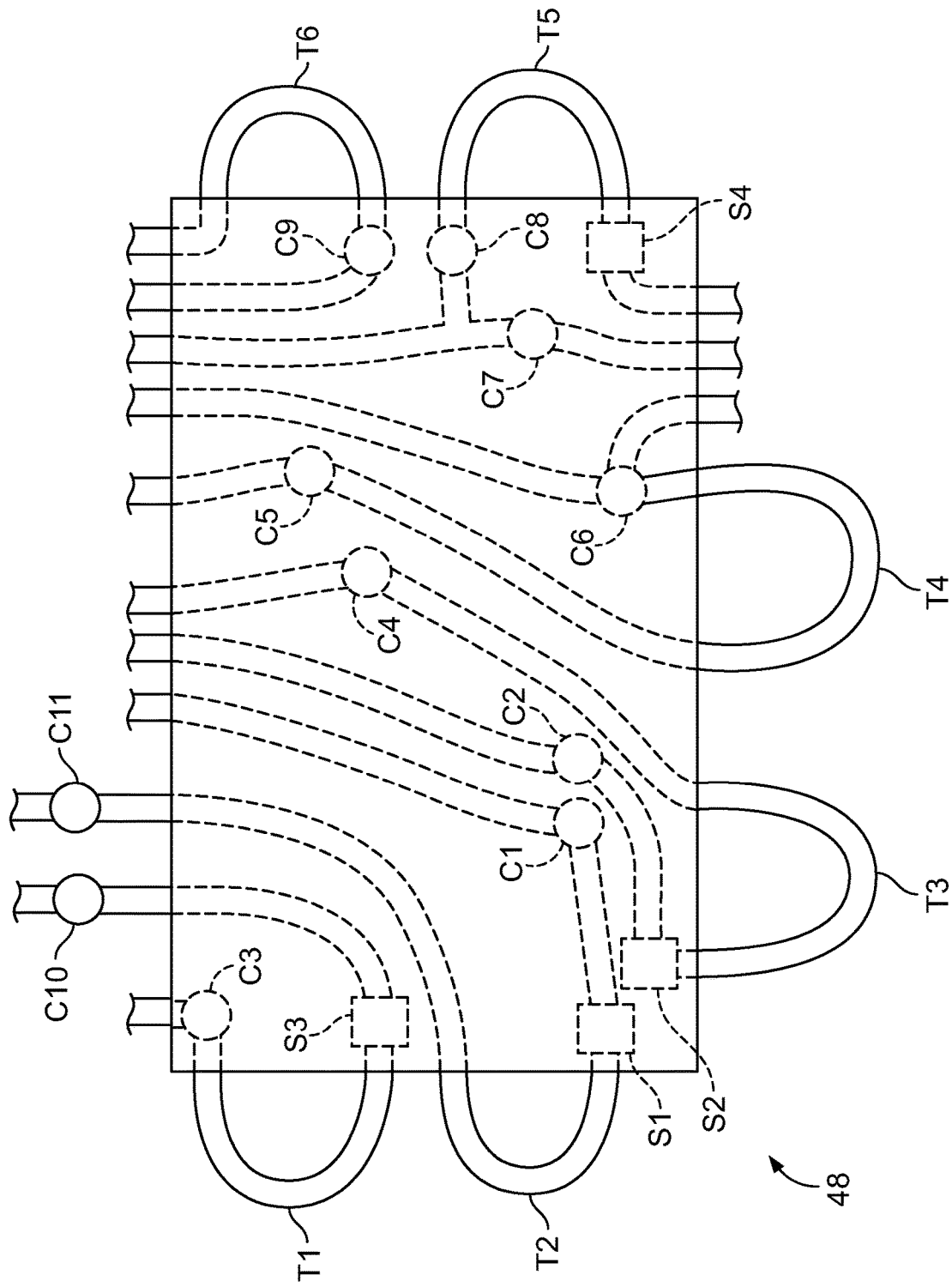
FIG. 4 is a top plan view of an exemplary cassette of a fluid flow circuit, which can be actuated to perform a variety of different blood processing procedures in association with the blood separation device shown in FIG. 1.

The particular configuration and operation of the centrifugal separator 16 depends upon the particular configuration of the centrifugal separation chamber 36 of the fluid flow circuit 12. In one embodiment, the centrifugal separator 16 is similar in structure and operation to that of the ALYX system manufactured by Fenwal, Inc. of Lake Zurich, Illinois, which is an affiliate of Fresenius Kabi AG of Bad Homburg, Germany, as described in greater detail in U.S. Pat. No. 8,075,468, which is incorporated herein by reference. More particularly, the centrifugal separator 16 may include a carriage or support 42 that holds the centrifugal separation chamber 36 and a yoke member 44. The yoke member 44 engages an umbilicus 46 of the fluid flow circuit 12, which extends between the centrifugal separation chamber 36 and a cassette 48 of the fluid flow circuit 12 (FIG. 4). The yoke member 44 causes the umbilicus 46 to orbit around the centrifugal separation chamber 36 at a one omega rotational speed. The umbilicus 46 twists about its own axis as it orbits around the centrifugal separation chamber 36. The twisting of the umbilicus 46 about its axis as it rotates at one omega with the yoke member 44 imparts a two omega rotation to the centrifugal separation chamber 36, according to known design. The relative rotation of the yoke member 44 at a one omega rotational speed and the centrifugal separation chamber 36 at a two omega rotational speed keeps the umbilicus 46 untwisted, avoiding the need for rotating seals.

Figure 6:
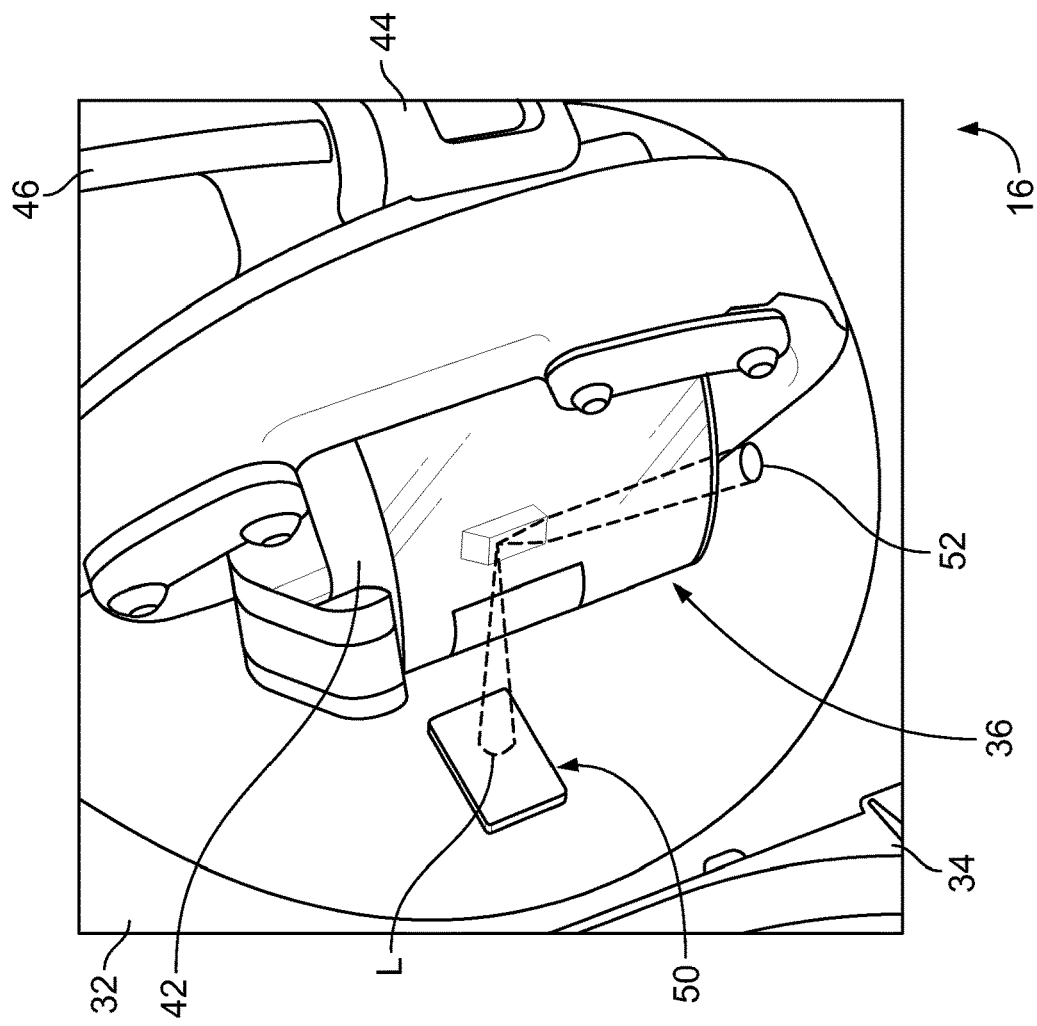
FIG. 6 is a perspective view of the centrifugal separator of FIG. 3, with the light source operating to transmit a light beam to a light detector of the interface monitoring system.
Figure 5:
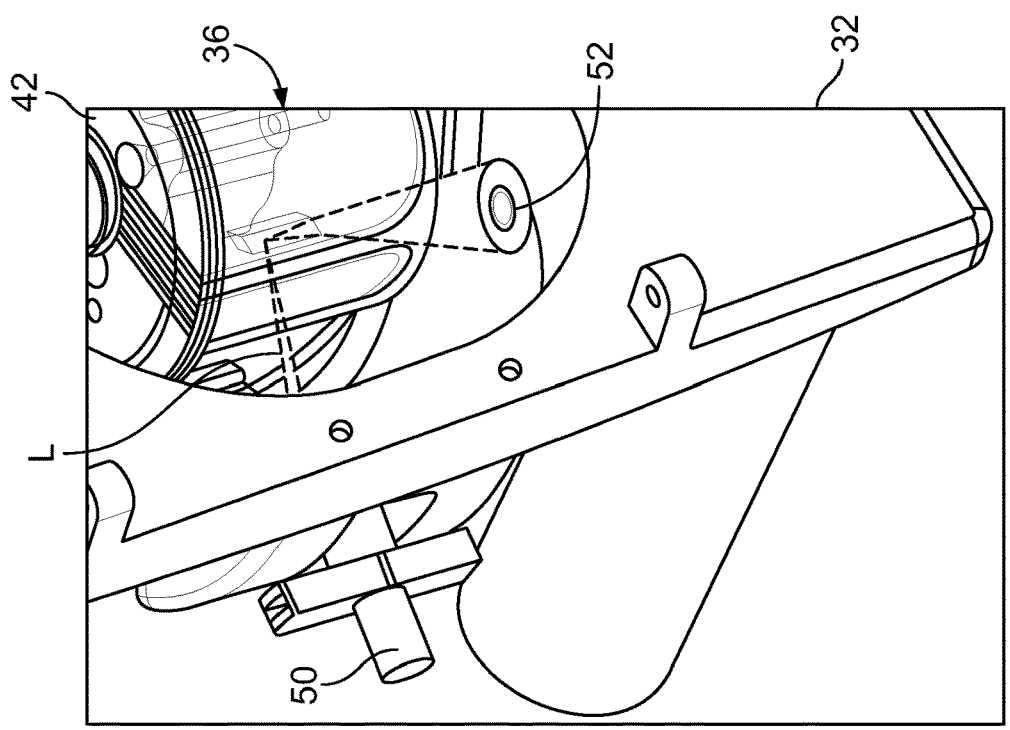
FIG. 5 is a perspective view of the centrifugal separator of FIG. 3, with selected portions thereof broken away to show a light source of an interface monitoring system.
Figure 7:
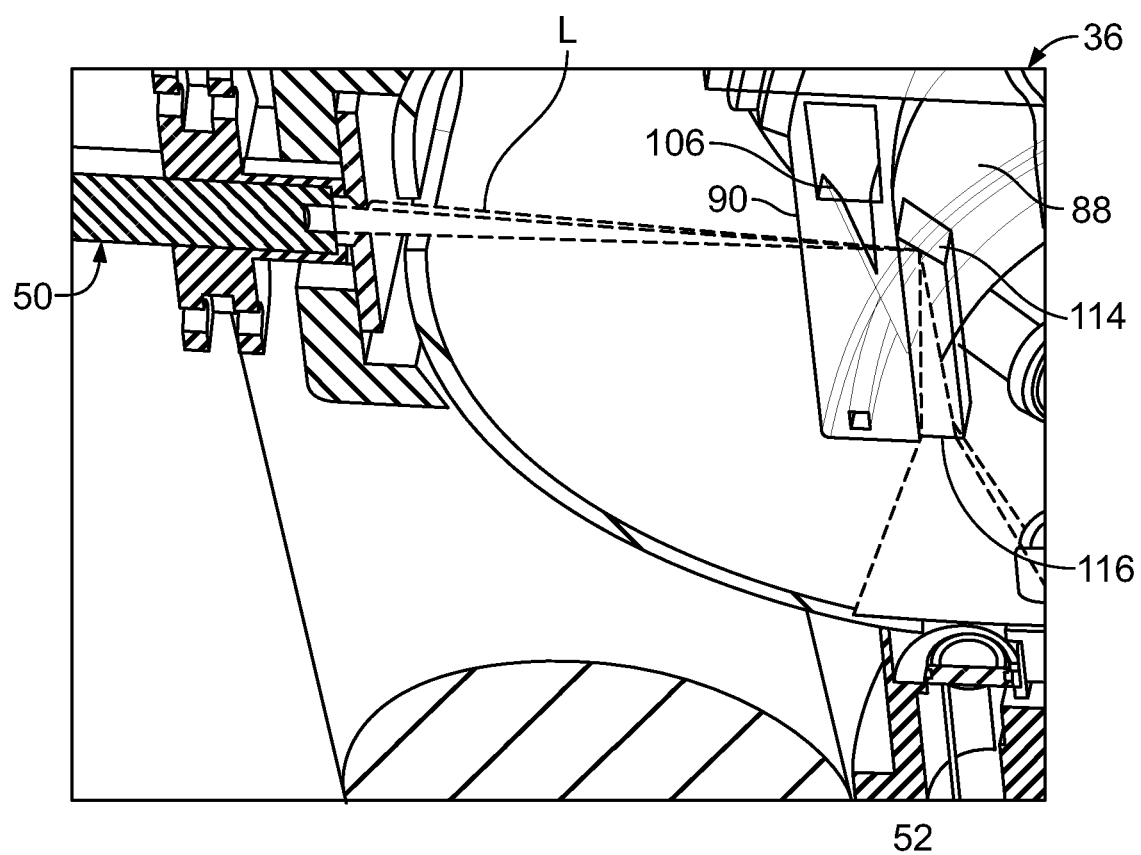
FIG. 7 is a perspective view of the centrifugal separator of FIG. 3, with selected portions thereof broken away to show the light source and light detector of the interface monitoring system.

Blood is introduced into the centrifugal separation chamber 36 by the umbilicus 46, with the blood being separated (e.g., into a layer of less dense components, such as platelet-rich plasma, and a layer of more dense components, such as packed red blood cells) within the centrifugal separation chamber 36 as a result of centrifugal forces as it rotates. Components of an interface monitoring system may be positioned within the centrifuge compartment 32 to oversee separation of blood within the centrifugal separation chamber 36. As shown in FIGS. 5-7, the interface monitoring system may include a light source 50 and a light detector 52, which is positioned and oriented to receive at least a portion of the light emitted by the light source 50. Preferably, the light source 50 and the light detector 52 are positioned on stationary surfaces of the centrifuge compartment 32, but it is also within the scope of the present disclosure for one or both to be mounted to a movable component of the centrifugal separator 16 (e.g., to the yoke member 44, which rotates at a one omega speed).

The orientation of the various components of the interface monitoring system depends at least in part on the particular configuration of the centrifugal separation chamber 36, which will be described in greater detail herein. In general, though, the light source 50 emits a light beam (e.g., a laser light beam) through the separated blood components within the centrifugal separation chamber 36 (which may be formed of a material that substantially transmits the light or at least a particular wavelength of the light without absorbing it). A portion of the light reaches the light detector 52, which transmits a signal to the controller 18 that is indicative of the location of an interface between the separated blood components. If the controller 18 determines that the interface is in the wrong location (which can affect the separation efficiency of the centrifugal separator 16 and/or the quality of the separated blood components), then it can issue commands to the appropriate components of the blood separation device 10 to modify their operation so as to move the interface to the proper location.

C. Other Components of the Blood Separation Device

In addition to the spinning membrane separator drive unit 14 and the centrifugal separator 16, the blood separation device 10 may include other components compactly arranged to aid blood processing.

The generally horizontal portion 22 of the case 20 of the illustrated blood separation device 10 includes a cassette station 54, which accommodates a cassette 48 of the fluid flow circuit 12 (FIG. 4). In one embodiment, the cassette station 54 is similarly configured to the cassette station of U.S. Pat. No. 5,868,696 (which is incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 2 and 4). Depending on the configuration of the fluid flow circuit 12, its cassette 48 may not include a valve station C1-C9 for each valve V1-V9 of the cassette station 54, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 52 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the blood source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifugal separation chamber 36. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The blood separation device 10 may also include a plurality of pumps P1-P6 (which may be collectively referred to as a pump assembly) cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 4) and may be selectively operated under command of the controller 18 to cause fluid to flow through a portion of the fluid flow circuit 12, as will be described in greater detail. In one embodiment, all or a portion of the cassette station 54 may be capable of translational motion in and out of the case 20 to allow for automatic loading of the tubing loops T1-T6 into the associated pump P1-P6.

The illustrated blood separation device 10 also includes a centrifugal separator sensor M1 for determining one or more properties of fluids flowing out of and/or into the centrifugal separator 16. If the fluid flowing out of the centrifugal separator 16 includes red blood cells, the centrifugal separator sensor M1 may be configured to determine the hematocrit of the fluid. If the fluid flowing out of the centrifugal separator 16 is platelet-rich plasma, the centrifugal separator sensor M1 may be configured to determine the platelet concentration of the platelet-rich plasma. The centrifugal separator sensor M1 may detect the one or more properties of a fluid by optically monitoring the fluid as it flows through tubing of the fluid flow circuit 12 or by any other suitable approach. The controller 18 may receive signals from the centrifugal separator sensor M1 that are indicative of the one or more properties of fluid flowing out of the centrifugal separator 16 and use the signals to optimize the separation procedure based upon that property or properties. If the property or properties is/are outside of an acceptable range, then the controller 18 may initiate an alarm or error condition to alert an operator to the condition. A suitable device and method for monitoring hematocrit and/or platelet concentration is described in U.S. Pat. No. 6,419,822 (which is incorporated herein by reference), but it should be understood that a different approach may also be employed for monitoring hematocrit and/or platelet concentration of fluid flowing out of the centrifugal separator 16.

The illustrated blood separation device 10 further includes a spinner outlet sensor M2, which accommodates tubing of the fluid flow circuit 12 that flows a separated substance out of the spinning membrane separator 26. The spinner outlet sensor M2 monitors the substance to determine one or more properties of the substance, and may do so by optically monitoring the substance as it flows through the tubing or by any other suitable approach. For example, a supernatant or a combination of a supernatant, platelets, and smaller red blood cells may flow through the tubing as a waste product, in which case the spinner outlet sensor M2 may be configured to monitor the optical characteristics of the waste product for quality purposes, such as monitoring for cell loss or hemolysis.

The illustrated blood separation device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F7 of the fluid flow circuit 12 (FIG. 2). The containers F1-F7 receive blood components or waste products separated during processing or intravenous fluids or additive fluids. Each weight scale W1-W6 transmits to the controller 18 a signal that is indicative of the weight of the fluid within the associated container F1-F7 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 12 or other suitably sized and configured objects.

D. Controller

According to an aspect of the present disclosure, the blood separation device 10 includes a controller 18, which is suitably configured and/or programmed to control operation of the blood separation device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the blood separation device 10.

The controller 18 is configured and/or programmed to execute at least one blood processing application but, more advantageously, is configured and/or programmed to execute a variety of different blood processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and (as will be described in detail herein) an MNC collection procedure. Additional or alternative procedure applications can be included without departing from the scope of the present disclosure.

More particularly, in carrying out any one of these blood processing applications, the controller 18 is configured and/or programmed to control one or more of the following tasks: drawing blood into a fluid flow circuit 12 mounted to the blood separation device 10, conveying blood through the fluid flow circuit 12 to a location for separation (i.e., into a spinning membrane separator 26 or centrifugal separation chamber 36 of the fluid flow circuit 12), separating the blood into two or more components as desired, and conveying the separated components into storage containers, to a second location for further separation (e.g., into whichever of the spinning membrane separator 26 and centrifugal separation chamber 36 that was not used in the initial separation stage), or to a recipient (which may be the source from which the blood was originally drawn).

This may include instructing the spinning membrane separator drive unit 14 and/or the centrifugal separator 16 to operate at a particular rotational speed and instructing a pump P1-P6 to convey fluid through a portion of the fluid flow circuit 12 at a particular flow rate. Hence, while it may be described herein that a particular component of the blood separation device 10 (e.g., the spinning membrane separator drive unit 14 or the centrifugal separator 16) performs a particular function, it should be understood that that component is being controlled by the controller 18 to perform that function.

As will be described, a procedure may call for the use of both the centrifugal separator 16 and the spinning membrane separator drive unit 14, in which case a properly programmed controller 18 is especially important to coordinate the operation of these two components, along with the other components of the blood separation device 10 to ensure that flow to and from the centrifugal separator 16 and spinning membrane separator drive unit 14 is at the proper level and that the components are functioning properly to process the blood circulating through the fluid flow circuit 12.

Before, during, and after a procedure, the controller 18 may receive signals from various components of the blood separation device 10 (e.g., the pressure sensors A1-A4) to monitor various aspects of the operation of the blood separation device 10 and characteristics of the blood and separated blood components as they flow through the fluid flow circuit 12. If the operation of any of the components and/or one or more characteristics of the blood or separated blood components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring system. The signals that the controller 18 receives from the light detector 52 are indicative of the location of an interface between the separated blood components within the centrifugal separation chamber 36. If the controller 18 determines that the interface is in the wrong location, then it can issue commands to the appropriate components of the blood separation device 10 to modify their operation so as to move the interface to the proper location. For example, the controller 18 may instruct one of the pumps P1-P6 to cause blood to flow into the centrifugal separation chamber 36 at a different rate and/or for a separated blood component to be removed from the centrifugal separation chamber 36 at a different rate and/or for the centrifugal separation chamber 36 to be spun at a different speed by the centrifugal separator 16. A particular protocol carried out by the interface control module in adjusting the position of the interface within the centrifugal separation chamber 36 will be described in greater detail with respect to an exemplary centrifugal separation chamber 36.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIG. 2), it is intended to be a sterile, single use, disposable item. Before beginning a given blood processing and collection procedure, the operator loads various components of the fluid flow circuit 12 in the case 20 in association with the blood separation device 10. The controller 18 implements the procedure based upon preset protocols, taking into account other input from the operator. Upon completing the procedure, the operator removes the fluid flow circuit 12 from association with the blood separation device 10. The portions of the fluid flow circuit 12 holding the collected blood component or components (e.g., collection containers or bags) are removed from the case 20 and retained for storage, transfusion, or further processing. The remainder of the fluid flow circuit 12 is removed from the case 20 and discarded.

A variety of different disposable fluid flow circuits may be used in combination with the blood separation device 10, with the appropriate fluid flow circuit depending on the separation procedure to be carried out using the system. Generally speaking, though, the fluid flow circuit 12 includes a cassette 48 (FIG. 4), to which the other components of the fluid flow circuit 12 are connected by flexible tubing. The other components may include a plurality of fluid containers F1-F7 (for holding blood, a separated blood component, an intravenous fluid, or an additive solution, for example), one or more blood source access devices (e.g., a connector for accessing blood within a fluid container), and a spinning membrane separator 26 (FIGS. 8 and 9) and/or a centrifugal separation chamber 36 (FIGS. 10-17).

B. Cassette And Tubing

The cassette 48 (FIG. 4) provides a centralized, programmable, integrated platform for all the pumping and many of the valving functions required for a given blood processing procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the blood separation device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted and lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the blood separation device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure (as will be described in greater detail), but in one embodiment, a different one of the pumps P1-P6 may be configured to serve as an anticoagulant pump P1, a source pump P2, a recirculation pump P3, a transfer pump P4, a plasma pump P5, and a waste pump P6. Certain procedures require fewer than all of the sensor stations, valve stations, and/or tubing loops illustrated in the exemplary cassette 48 of FIG. 4, such that it should be understood that the cassettes of different fluid flow circuits 12 may be differently configured (e.g., with fewer sensor stations, valve stations, and/or tubing loops) without departing from the scope of the present disclosure.

Additional tubing extends from the side surface of the cassette 48 to connect to the other components of the fluid flow circuit 12, such as the various fluid containers F1-F5, the spinning membrane separator 26, and the centrifugal separation chamber 36. The number and content of the various fluid containers F1-F7 depends upon the procedure for which the fluid flow circuit 12 is used, with the fluid containers F1-F7 of one particular fluid flow circuit 12 and procedure being described in greater detail herein. If the fluid flow circuit 12 includes a centrifugal separation chamber 36, then the tubing connected to it (which includes one inlet tube and two outlet tubes) may be aggregated into an umbilicus 46 (FIG. 3) that is engaged by the yoke member 44 of the centrifugal separator 16 (as described above) to cause the umbilicus 46 to orbit around and spin or rotate the centrifugal separation chamber 36 during a separation procedure.

Various additional components may be incorporated into the tubing leading out of the cassette 48 or into one of the cavities of the cassette 48. For example, as shown in FIG. 2, a manual clamp 56 may be associated with a line or lines leading to the blood source and/or fluid recipient, a return line filter 58 (e.g., a microaggregate filter) may be associated with a line leading to a fluid recipient, filters (not illustrated) may be positioned upstream of one or more of the fluid containers to remove a substance (e.g., leukocytes) from a separated component (e.g., red blood cells or platelets) flowing into the fluid container, and/or an air trap 62 may be positioned on a line upstream of the centrifugal separation chamber 36.

C. Spinning Membrane Separator

Figure 8:
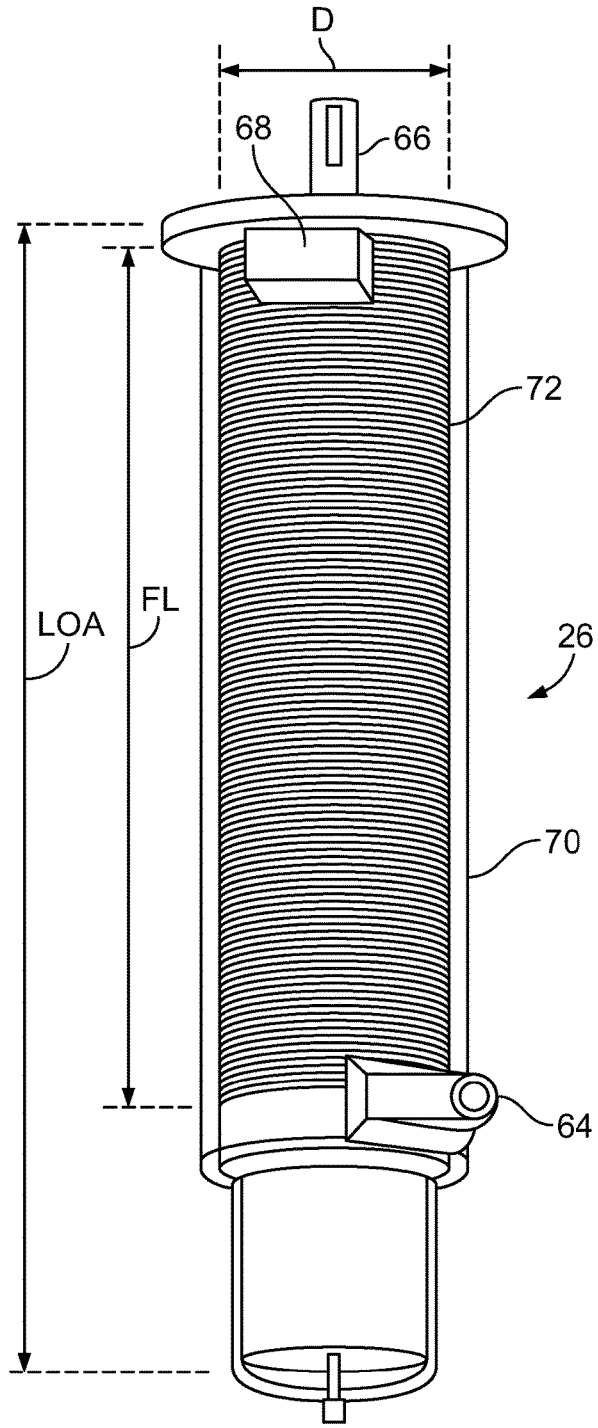
FIG. 8 is a perspective view of an exemplary spinning membrane separator of a fluid flow circuit.
Figure 9:
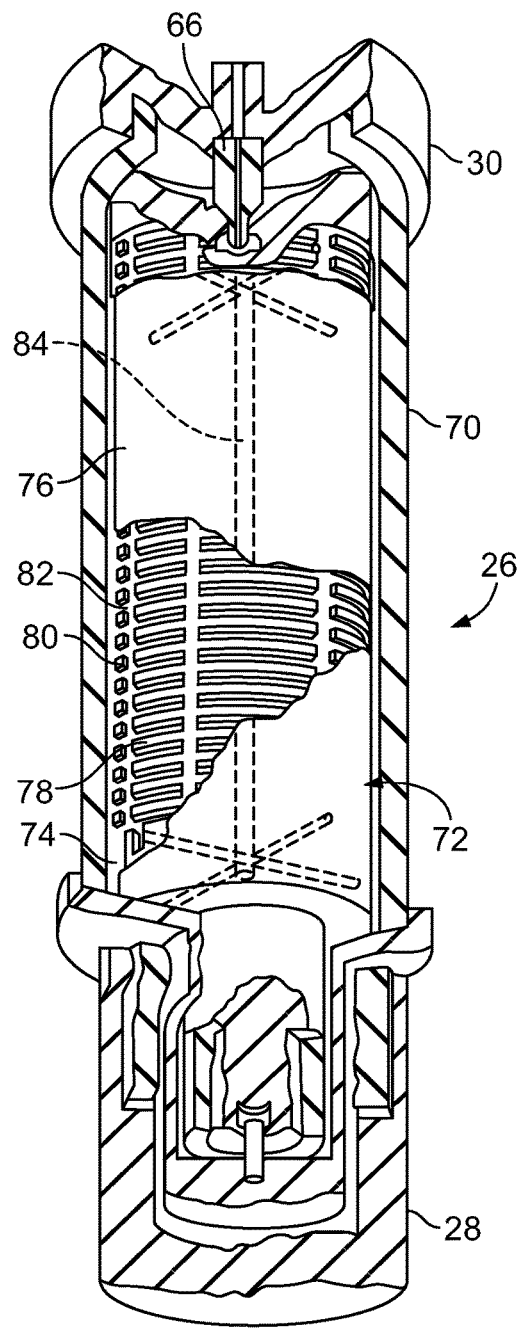
FIG. 9 is a perspective view of the spinning membrane separator of FIG. 8 and a portion of a spinning membrane separator drive unit, with portions of both being cut away for illustrative purposes.

Turning to FIGS. 8 and 9, a spinning membrane separator 26 is shown. As will be described in greater detail, the spinning membrane separator 26 may be used for washing a mononuclear cell product (including T-cell lymphocytes). The spinning membrane separator 26 is associated with the remainder of the fluid flow circuit 12 by an inlet port 64 and two outlet ports 66 and 68. The inlet port 64 is shown as being associated with a bottom end or portion of the spinning membrane separator 26, while the outlet ports 66 and 68 are associated with an upper end or portion of the spinning membrane separator 26, but it is within the scope of the present disclosure for the spinning membrane separator 26 to be inverted, with fluid entering an upper end or portion of the spinning membrane separator 26 and fluid exiting a lower end or portion of the spinning membrane separator 26.

The illustrated spinning membrane separator 26 includes a generally cylindrical housing 70 mounted concentrically about a longitudinal vertical central axis. An internal member or rotor 72 is mounted concentrically with the central axis. The housing 70 and rotor 72 are relatively rotatable, as described above with respect to the spinning membrane separator drive unit 14. In a preferred embodiment, the housing 70 is stationary and the rotor 72 is a rotating spinner that is rotatable concentrically within the cylindrical housing 70. In such an embodiment, the housing 70 (or at least its upper and lower ends) are formed of non-magnetic material, while the rotor 72 includes an element (e.g., a metallic material) that interacts with a magnet of the spinning membrane separator drive unit 14 to rotate the rotor 72 within the housing 70, as described above.

The boundaries of the blood flow path are generally defined by the gap 74 between the interior surface of the housing 70 and the exterior surface of the rotor 72, which is sometimes referred to as the shear gap. A typical shear gap 74 may be approximately 0.025-0.050 inches (0.067-0.127 cm) and may be of a uniform dimension along the axis, for example, where the axis of the housing 70 and rotor 72 are coincident. Alternatively, the width of the shear gap 74 also may vary along the axial direction, for example with the width of the gap 74 increasing in the direction of flow to limit hemolysis. Such a gap width may range from about 0.025 to about 0.075 inches (0.06-0.19 cm). For example, in one embodiment, the axes of the housing 70 and rotor 72 are coincident, with the outer diameter of the rotor 72 decreasing in the direction of flow, while the inner diameter of the housing 70 remaining constant. In other embodiments, the inner diameter of the housing 70 may increase while the outer rotor diameter remains constant or both surfaces may vary in diameter. In one exemplary embodiment, the gap width may be about 0.035 inches (0.088 cm) at the upstream or inlet end of the gap 74 and about 0.059 inches (0.15 cm) at the downstream end or terminus of the gap 74. The gap width could change linearly or stepwise or in some other manner as may be desired. In any event, the width dimension of the gap 74 is preferably selected so that at the desired relative rotational speed, Taylor-Couette flow, such as Taylor vortices, are created in the gap 74 and hemolysis is limited.

A fluid to be washed is fed into the gap 74 by the inlet port 64 (FIG. 8), which directs the fluid into the fluid flow entrance region at or adjacent to the bottom end of the spinning membrane separator 26. The spinning membrane separator drive unit 14 causes relative rotation of the housing 70 and rotor 72, creating Taylor vortices within the gap 74. The outer surface of the rotor 72 and/or the inner surface of the housing 70 is at least partially (and more preferably, substantially or entirely) covered by a cylindrical porous membrane 76 (shown in FIG. 9 as being mounted to the outer surface of the rotor 72). It should be, thus, understood that the term "spinning membrane separator" does not necessarily require that the membrane 76 is mounted to a component of the spinning membrane separator 26 that spins, but may also include a device in which the membrane 76 is mounted to a stationary component that includes another component that rotates with respect to the stationary membrane 76.

The membrane 76 typically has a nominal pore size that may vary, depending on the nature of the substances to be removed. For example, if only a supernatant is to be filtered out during cell washing of an MNC product, then a nominal pore size of 0.65-0.8 microns may be employed. In another example, in which supernatant, platelets, and some smaller red blood cells are to be filtered out, a nominal pore size of 4.0 microns may be advantageous. It should be understood that these are only exemplary and that membranes having other pore sizes may alternatively be used without departing from the scope of the present disclosure. Membranes useful in the methods described herein may be fibrous mesh membranes, cast membranes, track-etched membranes or other types of membranes that will be known to those of skill in the art. For example, in one embodiment, the membrane 76 may have a polyester mesh (substrate) with nylon particles solidified thereon, thereby creating a tortuous path through which only certain sized components will pass. In another embodiment, the membrane 76 may be made of a thin (approximately 15 micron thick) sheet of, for example, polycarbonate with pores or holes defined therein that are sized and configured to allow passage of only a selected one or more blood components.

In an embodiment in which the rotor 72 spins within the housing 70 and the membrane 76 is mounted to the outer surface of the rotor 72, the outer surface of the rotor 72 may be shaped to define a series of spaced-apart circumferential grooves or ribs 78 separated by annular lands 80 (FIG. 9). The surface channels defined by the circumferential grooves 78 are interconnected by longitudinal grooves 82. At one or both ends of the rotor 72, these grooves 78 are in communication with a central orifice or manifold 84. Pumping fluid into and out of the spinning membrane separator 26 causes the substance being filtered out (e.g., a supernatant) to flow through the membrane 76 and grooves 78, while the while remainder of the fluid (e.g., T-cells) remains within the gap 74 as fluid flows from the inlet port 64 at the bottom portion of the spinning membrane separator 26 toward the upper portion. Relative rotation of the rotor 72 and housing 70 causes a particular flow pattern within the gap 74 (described above) that enables filtration without clogging the membrane 76.

At the upper portion of the spinning membrane separator 26, the substance being filtered out (e.g., the supernatant) exits the spinning membrane separator 26 via an outlet port 66 that is concentric with the rotational axis and in fluid communication with the central orifice 84 of the rotor 72 (FIG. 9), with the substance flowing into a line associated with the outlet port 66. The remainder of the fluid (e.g., the T-cells) exits the gap 74 via an outlet port 68 defined in the upper end or portion of the housing 70 and oriented generally tangentially to the gap 74 (FIG. 8), flowing into a line associated with the outlet port 68.

As described above, it may be advantageous to use differently sized spinning membrane separators 26 depending on the particular blood separation procedure being carried out. FIG. 8 shows a spinning membrane separator 26 having a rotor 72 with a spinner diameter D, a filtration length FL, and an overall length LOA. An exemplary smaller spinning membrane separator may have a spinner diameter D of approximately 1.1", a filtration length FL of approximately 3", and an overall length LOA of approximately 5.0". By comparison, an exemplary larger spinning membrane separator may have a spinner diameter D of approximately 1.65", a filtration length FL of approximately 5.52", and an overall length LOA of approximately 7.7". An exemplary smaller spinning membrane separator is described in greater detail in U.S. Pat. No. 5,194,145, while an exemplary larger spinning membrane separator is described in greater detail in U.S. Patent Application Publication No. 2015/0218517, which is incorporated herein by reference.

D. Centrifugal Separation Chamber

Figure 10:
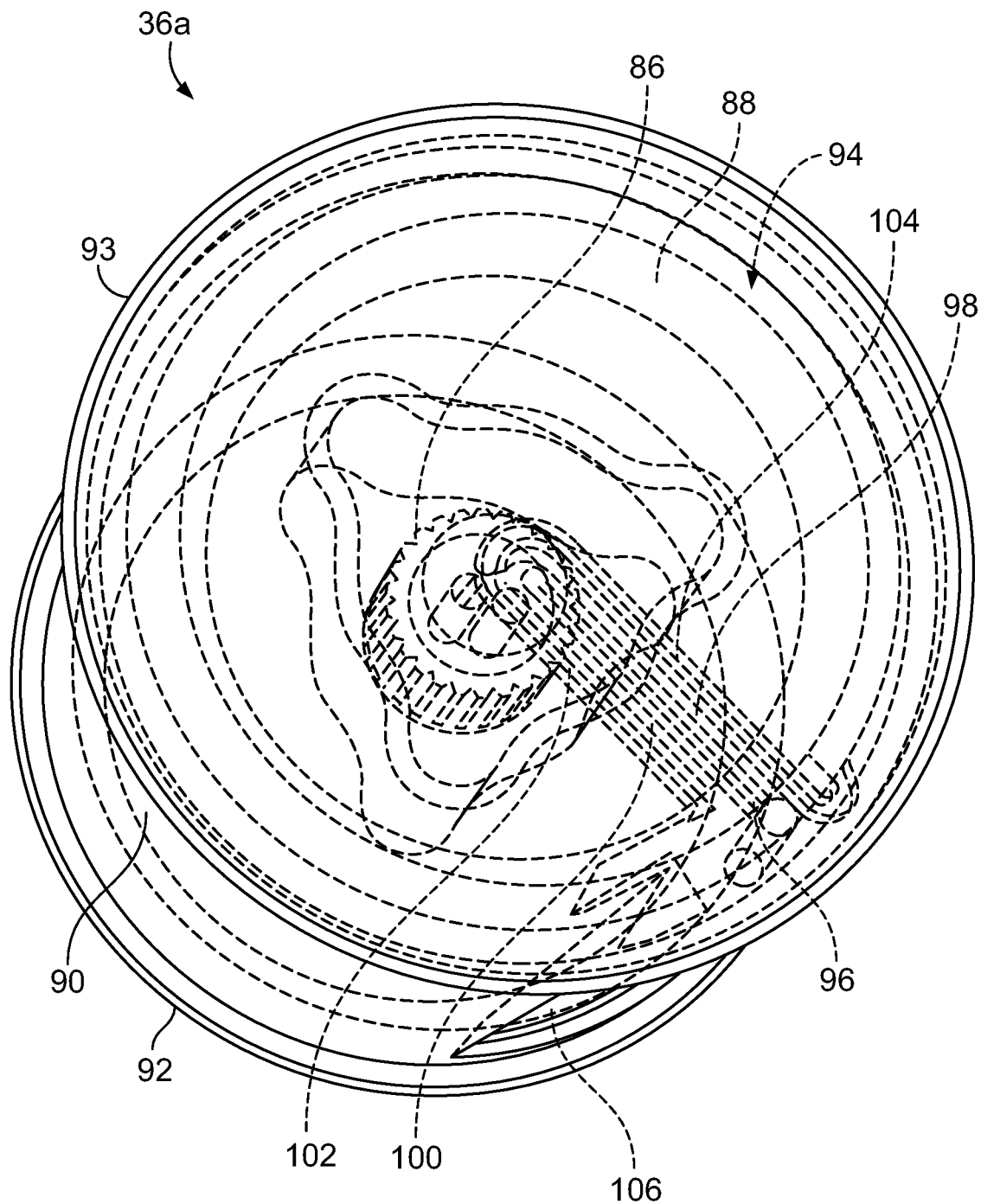
FIG. 10 is a perspective view of an exemplary centrifugal separation chamber of a fluid flow circuit.
Figure 11:
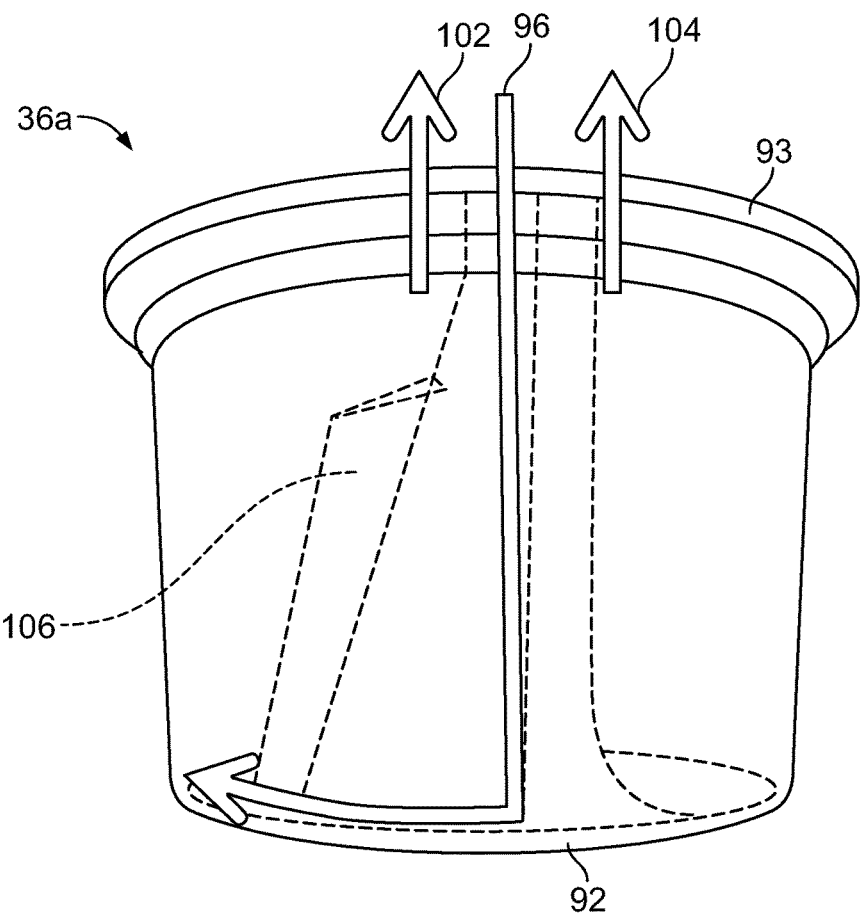
FIG. 11 is a front elevational view of the centrifugal separation chamber of FIG. 10.
Figure 12:
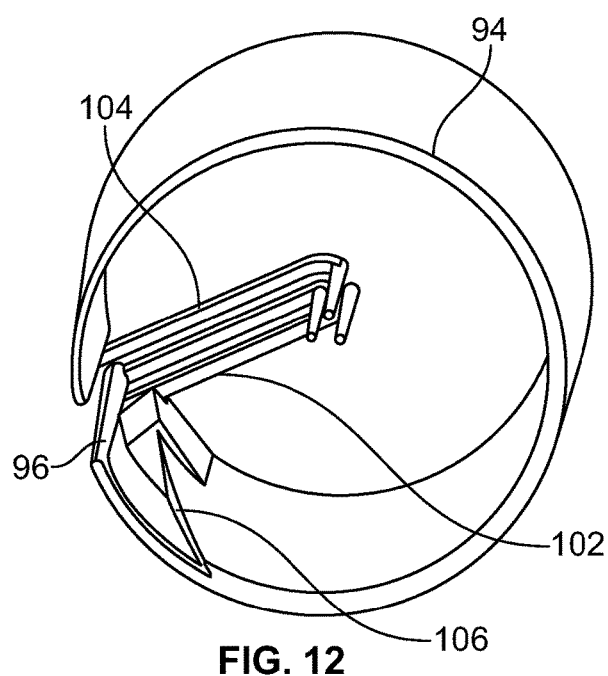
FIG. 12 is a bottom perspective view of the fluid flow path through the centrifugal separation chamber of FIG. 10.

A fluid flow circuit 12 may be provided with a centrifugal separation chamber 36 if platelets, white blood cells, and/or (as described herein) MNCs are to be separated and collected. An exemplary centrifugal separation chamber 36a is shown in FIGS. 10 and 11, while FIG. 12 illustrates the fluid flow path defined by the centrifugal separation chamber 36a. In the illustrated embodiment, the body of the centrifugal separation chamber 36a is pre-formed in a desired shape and configuration (e.g., by injection molding) from a rigid, biocompatible plastic material, such as a non-plasticized medical grade acrylonitrile-butadiene-styrene (ABS). All contours, ports, channels, and walls that affect the blood separation process are preformed in a single, injection molded operation. Alternatively, the centrifugal separation chamber 36a can be formed by separate molded parts, either by nesting cup-shaped subassemblies or two symmetric halves.

The underside of the centrifugal separation chamber 36a includes a shaped receptacle 86 that is suitable for receiving an end of the umbilicus 46 of the fluid flow circuit 12 (FIG. 3). A suitable receptacle 86 and the manner in which the umbilicus 46 may cooperate with the receptacle 86 to deliver fluid to and remove fluid from the centrifugal separation chamber 36a are described in greater detail in U.S. Pat. No. 8,075,468.

The illustrated centrifugal separation chamber 36a has radially spaced apart inner (low-g) and outer (high-g) side wall portions 88 and 90, a bottom or first end wall portion 92, and a cover or second end wall portion 93. The cover 93 comprises a simple flat part that can be easily welded or otherwise secured to the body of the centrifugal separation chamber 36a. Because all features that affect the separation process are incorporated into one injection molded component, any tolerance differences between the cover 93 and the body of the centrifugal separation chamber 36a will not affect the separation efficiencies of the centrifugal separation chamber 36a. The wall portions 88 and 90, the bottom 92, and the cover 93 together define an enclosed, generally annular channel 94 (FIG. 12).

The (whole blood) inlet 96 communicating with the channel 94 is defined between opposing interior radial walls 98 and 100. One of the interior walls 98 joins the outer (high-g) wall portion 90 and separates the upstream and downstream ends of the channel 94. The interior walls 98 and 100 define the inlet passageway 96 of the centrifugal separation chamber 36a which, in one flow configuration, allows fluid to flow from the umbilicus 46 to the upstream end of the channel 94.

The illustrated centrifugal separation chamber 36a further includes first and second outlets 102 and 104, respectively, which may be defined by opposing surfaces of interior radial walls. Both the first and second outlets 102 and 104 extend radially inward from the channel 94. The first (plasma) outlet 102 extends radially inward from an opening which, in the illustrated embodiment, is located at the inner side wall portion 88, while the second (red blood cell) outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

Figure 13:
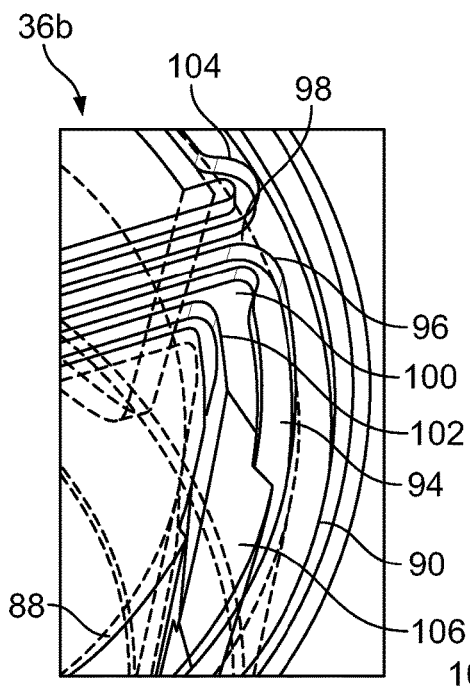
FIG. 13 is a perspective view of another embodiment of a centrifugal separation chamber of a fluid flow circuit.
Figure 14:
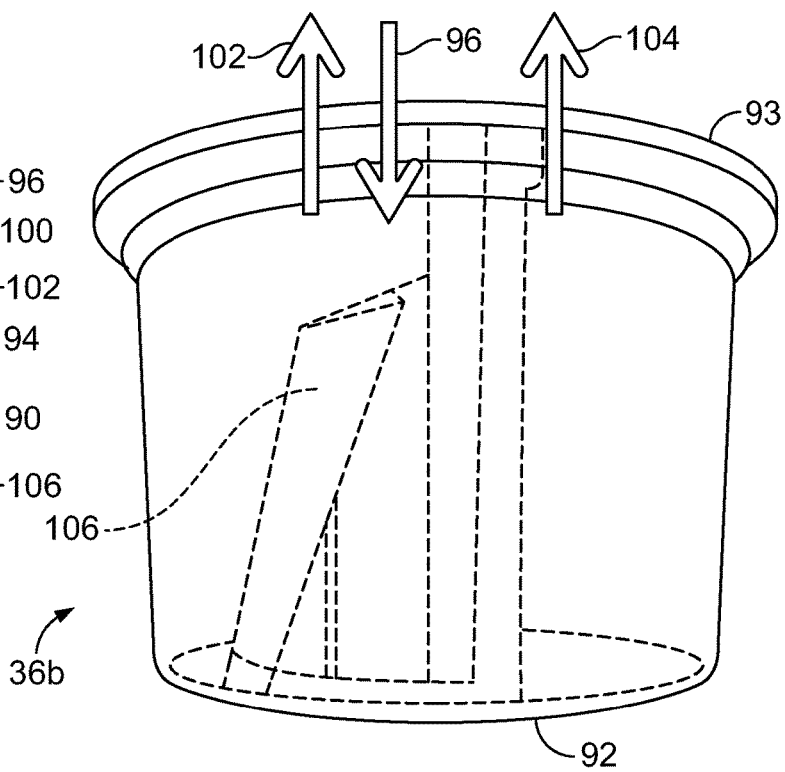
FIG. 14 is a front elevational view of the centrifugal separation chamber of FIG. 13.
Figure 15:
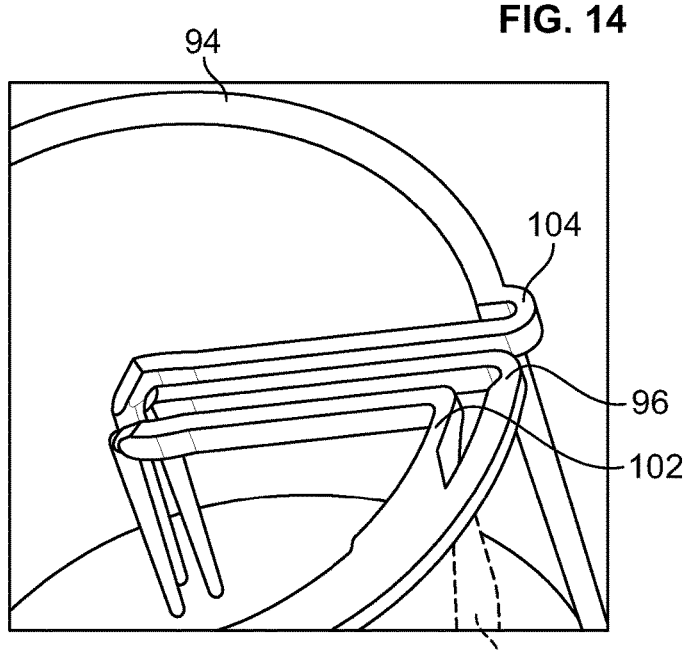
FIG. 15 is a top perspective view of the fluid flow path through the centrifugal separation chamber of FIG. 13.

It should be understood that the centrifugal separation chamber 36a illustrated in FIG. 10 is merely exemplary and that the centrifugal separation chamber 36 may be differently configured without departing from the scope of the present disclosure. For example, FIGS. 13 and 14 show an alternative embodiment of a centrifugal separation chamber 36b, while FIG. 15 illustrates the fluid flow path defined by the centrifugal separation chamber 36b. The centrifugal separation chamber 36b is similar to the centrifugal separation chamber 36a except for the location at which the inlet 96 opens into the channel 94. In the centrifugal separation chamber 36a of FIG. 10, the inlet 96 opens into the channel 94 adjacent to the first end wall portion 92 (while the outlets 102 and 104 open into the channel 94 adjacent to the second end wall portion 93), as best shown in FIGS. 11 and 12. In contrast, the inlet 96 of the centrifugal separation chamber 36b of FIG. 13 opens into the channel 94 adjacent to the second end wall portion 93 (along with the outlets 102 and 104), as best shown in FIGS. 14 and 15. The location at which the inlet 96 opens into the channel 94 may affect the separation of fluid within the channel 94, so the centrifugal separation chamber 36a of FIG. 10 may be preferable for certain procedures or for use in combination with certain blood separation devices, while the centrifugal separation chamber 36b of FIG. 13 may be preferable for other procedures or for use in combination with other blood separation devices.

Figure 16:
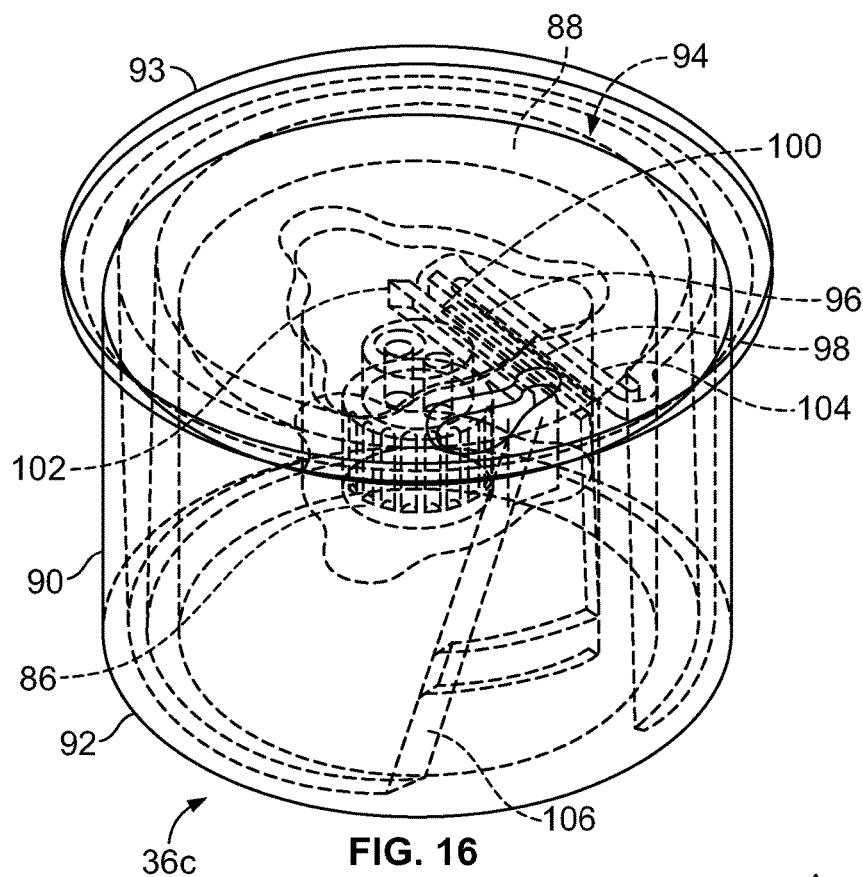
FIG. 16 is a perspective view of a third embodiment of a centrifugal separation chamber of a fluid flow circuit.
Figure 17:
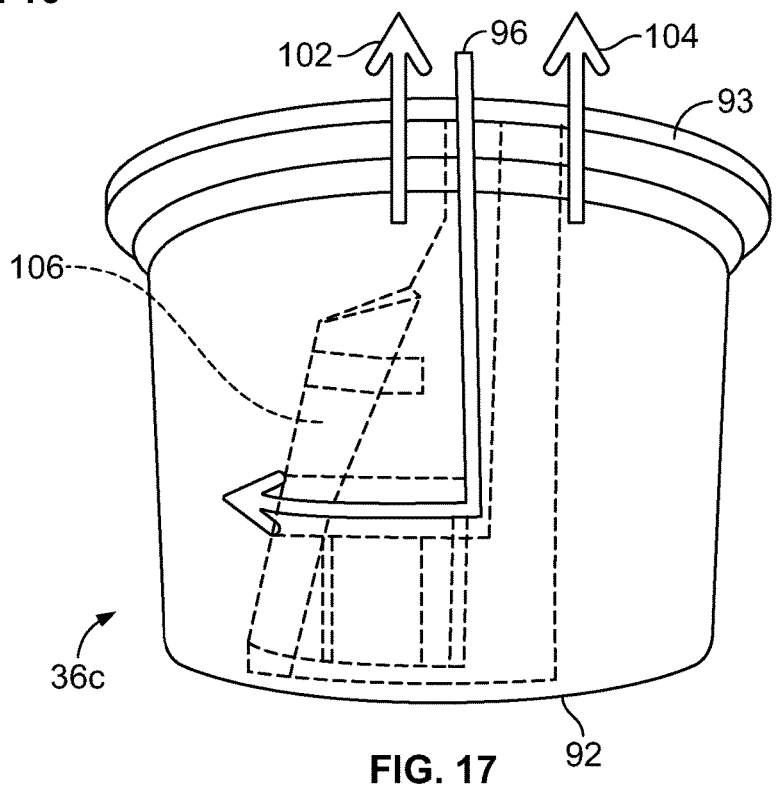
FIG. 17 is a front elevational view of the centrifugal separation chamber of FIG. 16.

FIGS. 16 and 17 show another exemplary embodiment of a centrifugal separation chamber 36c suitable for incorporation into a fluid flow circuit 12. The centrifugal separation chamber 36c is similar to the centrifugal separation chambers 36a and 36b of FIGS. 10 and 13 except for the location at which the inlet 96 opens into the channel 94. In contrast to the inlets 96 of the centrifugal separation chambers 36a and 36b of FIGS. 10 and 13, the inlet 96 of the centrifugal separation chamber 36c of FIG. 16 opens into the channel 94 at an intermediate axial location that is spaced from the first and second end wall portion 92 and 93 (while the outlets 102 and 104 open into the channel adjacent to the second end wall portion 93), as best shown in FIG. 17. The inlet 96 may open into the channel 94 at a location that is closer to the first end wall portion 92 than to the second end wall portion 93, at a location that is closer to the second end wall portion 93 than to the first end wall portion 92, or at a location that is equally spaced between the first and second end wall portions 92 and 93. The axial location at which the inlet 96 opens into the channel 94 may affect the separation of fluid within the channel 94, so the preferred location at which the inlet 96 opens into the channel 94 (which may also depend upon the nature of the blood separation device paired with the centrifugal separation chamber 36c) may be experimentally determined.

1. Centrifugal Separation and Interface Detection Principles

Blood flowed into the channel 94 separates into an optically dense layer RBC and a less optically dense layer PLS (FIGS. 18-20) as the centrifugal separation chamber 36 is rotated about the rotational axis 38. The optically dense layer RBC forms as larger and/or heavier blood particles move under the influence of centrifugal force toward the outer (high-g) wall portion 90. The optically dense layer RBC will typically include red blood cells (and, hence, may be referred to herein as the "RBC layer") but, depending on the speed at which the centrifugal separation chamber 36 is rotated, other cellular components (e.g., larger white blood cells) may also be present in the optically dense layer RBC.

The less optically dense layer PLS typically includes a plasma constituent, such as platelet-rich plasma or platelet-poor plasma (and, hence, will be referred to herein as the "PLS layer"). Depending on the speed at which the centrifugal separation chamber 36 is rotated and the length of time that the blood is resident therein, other components (e.g., smaller white blood cells and anticoagulant) may also be present in the less optically dense layer PLS.

In one embodiment, blood introduced into the channel 94 via the inlet 96 will travel in a generally clockwise direction (in the orientation of FIG. 10) as the optically dense layer RBC separates from the less optically dense layer PLS. The optically dense layer RBC continues moving in the clockwise direction as it travels the length of the channel 94 along the outer side wall portion 90, from the upstream end to the downstream end, where it exits the channel 94 via the second outlet 104. The less optically dense layer PLS separated from the optically dense layer RBC reverses direction, moving counterclockwise along the inner side wall portion 88 to the first outlet 102, adjacent to the inlet 96. The inner side wall portion 88 may be tapered inward as it approaches the second outlet 104 to force the plasma liberated at or adjacent to the downstream end of the channel 94 to drag the interface back towards the upstream end of the channel 94, where the lower surface hematocrit will re-suspend any platelets settled on the interface.

Figure 18:
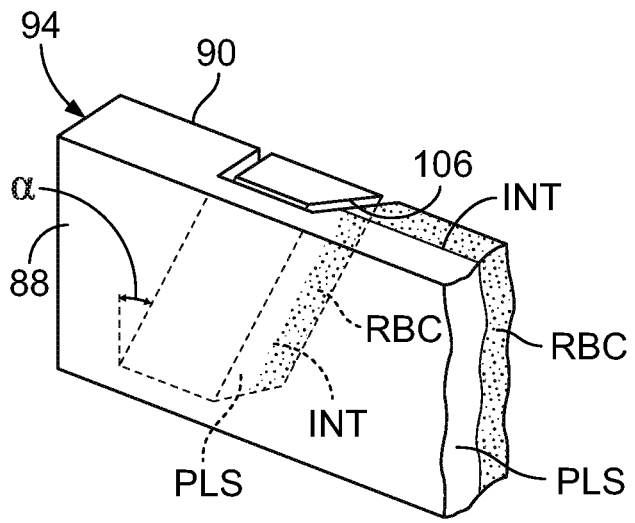
FIG. 18 is an enlarged perspective view of a portion of a channel of any of the centrifugal separation chambers of FIGS. 10-17, with an interface between separated blood components being positioned at a (typically) desired location on a ramp defined within the channel.
Figure 19:
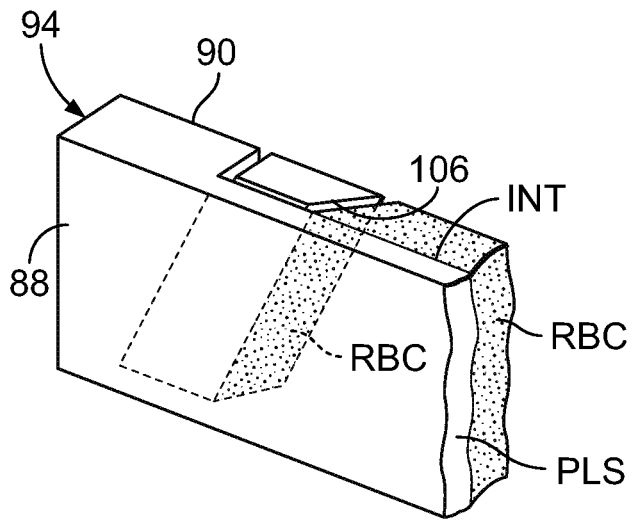
FIG. 19 is an enlarged perspective view of the channel and ramp of FIG. 18, with the interface being at a (typically) undesired high location on the ramp.
Figure 20:
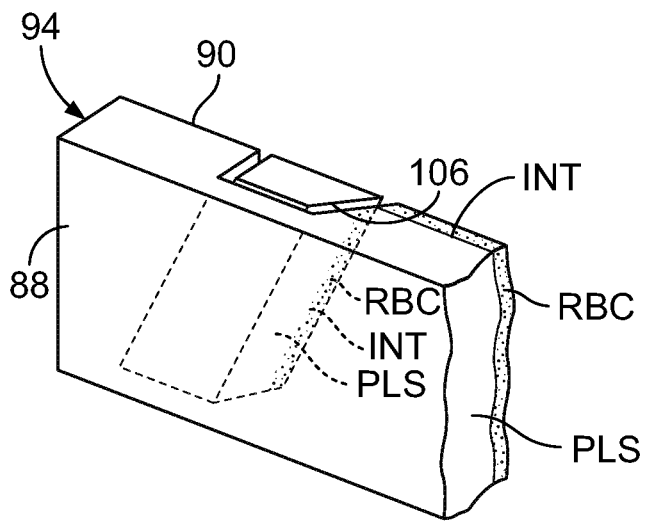
FIG. 20 is an enlarged perspective view of the channel and ramp of FIG. 18, with the interface being at a (typically) undesired low location on the ramp.

As described above, the transition between the optically dense layer RBC and the less optically dense layer PLS may be referred to as the interface INT. In one embodiment, the interface INT contains mononuclear cells and T-cell lymphocytes. The location of the interface INT within the channel 94 of the centrifugal separation chamber 36 can dynamically shift during blood processing, as FIGS. 18-20 show. If the location of the interface INT is too high (that is, if it is too close to the inner side wall portion 88 and the first outlet 102, as in FIG. 19), red blood cells can flow into the first outlet 102, potentially adversely affecting the quality of the low density components (platelet-rich plasma or platelet-poor plasma). On the other hand, if the location of the interface INT is too low (that is, if it resides too far away from the inner wall portion 88, as FIG. 20 shows), the collection efficiency of the system may be impaired. The ideal or target interface INT may be experimentally determined, which may vary depending on any of a number of factors (e.g., the configuration of the centrifugal separation chamber 36, the rate at which the centrifugal separation chamber 36 is rotated about the rotational axis 38, etc.). As will be described herein, it may be advantageous to temporarily move the interface INT away from the location of FIG. 18 during a separation procedure.

As described above, the blood separation device 10 may include an interface monitoring system and a controller 18 with an interface control module to monitor and, as necessary, correct the position of the interface INT. In one embodiment, the centrifugal separation chamber 36 is formed with a ramp 106 extending from the high-g wall portion 90 at an angle α across at least a portion of the channel 94 (FIGS. 10 and 18-20). The angle α, measured with respect to the rotational axis 38 is about 25° in one embodiment. FIGS. 18-20 show the orientation of the ramp 106 when viewed from the low-g side wall portion 88 of the centrifugal separation chamber 36. Although it describes a flexible separation chamber, the general structure and function of the ramp 106 may be better understood with reference to U.S. Pat. No. 5,632,893, which is incorporated herein by reference. The ramp 106 may be positioned at any of a number of locations between the upstream and downstream ends of the channel 94, but in one embodiment, the ramp 106 may be positioned generally adjacent to the first outlet 102, in the path of fluid and/or a fluid component moving from the inlet 96 to the first outlet 102.

The ramp 106 makes the interface INT between the optically dense layer RBC and the less optically dense layer PLS more discernible for detection, displaying the optically dense layer RBC, less optically dense layer PLS, and interface INT for viewing through a light-transmissive portion of the centrifugal separation chamber 36. To that end, the ramp 106 and at least the portion of the centrifugal separation chamber 36 angularly aligned with the ramp 106 may be formed of a light-transmissive material, although it may be advantageous for the entire centrifugal separation chamber 36 to be formed of the same light-transmissive material.

In the illustrated embodiment, the light source 50 of the interface monitoring system is secured to a fixture or wall of the centrifuge compartment 32 and oriented to emit a light that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 88, as shown in FIGS. 5 and 6. The reflector may be a separate piece that is secured to the inner side wall portion 88 (e.g., by being bonded thereto) or may be integrally formed with the body of the centrifugal separation chamber 36.

Figure 21:
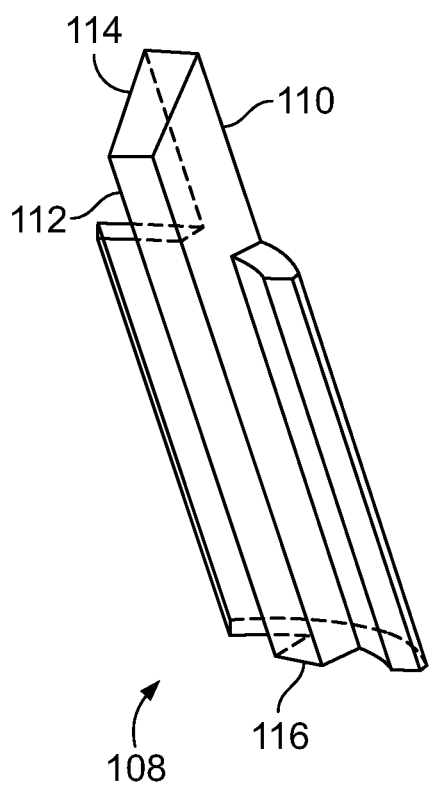
FIG. 21 is a perspective view of a prismatic reflector used in combination with any of the centrifugal separation chambers of FIGS. 10-17.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 108 (FIGS. 7, 21, and 22), which is formed of a light-transmissive material (e.g., a clear plastic material) and has inner and outer walls 110 and 112 and first and second end walls 114 and 116 (FIG. 21). The inner wall 110 is positioned against the inner side wall portion 88 of the centrifugal separation chamber 36 and is oriented substantially perpendicular to the initial path of the light L from the light source 50. This allows light L from the light source 50 to enter into the prismatic reflector 108 via the inner wall 110 while continuing along its initial path. The light L continues through the prismatic reflector 108 along its initial path until it encounters the first end wall 114. The first end wall 114 is oriented at an angle (e.g., an approximately 45° angle) with respect to the first surface 110 and the second end wall 116, causing the light to be redirected within the prismatic reflector 108, rather than exiting the prismatic reflector 108 via the first end wall 114.

Figure 22:
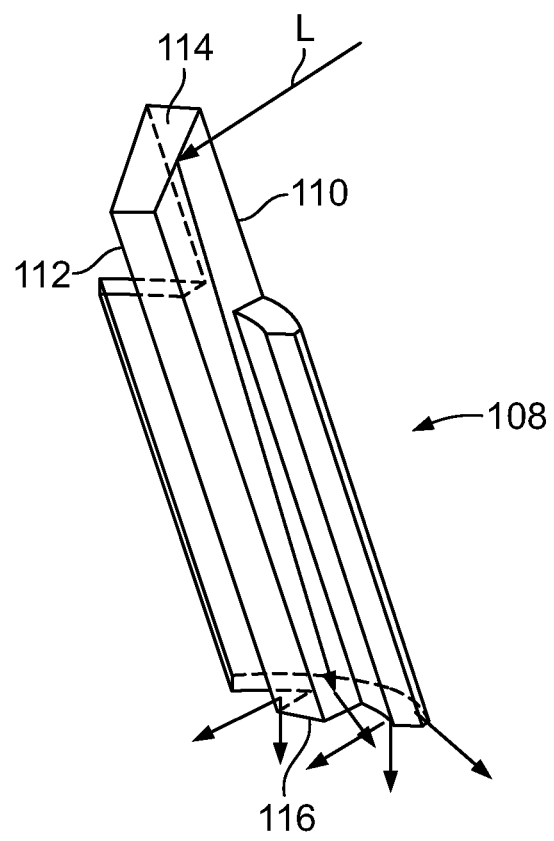
FIG. 22 is a perspective view of the prismatic reflector of FIG. 21, showing light being transmitted therethrough.

The first end wall 114 directs the light L at an angle to its initial path (which may be an approximately 90° angle, directing it from a path toward the rotational axis 38 to a path that is generally parallel to the rotational axis 38) toward the second end wall 116 (FIG. 22). The first end wall 114 and the inner and outer walls 110 and 112 of the prismatic reflector 108 may be configured to transmit the redirected light L from the first end wall 114 to the second end wall 116 by total internal reflection. The second end wall 116 is oriented substantially perpendicular to the redirected path of the light L through the prismatic reflector 108, such that the light L will exit the prismatic reflector 108 via the second end wall 116, continuing along its redirected path. In one embodiment, the second end wall 116 is roughened or textured or otherwise treated or conditioned to diffuse the light L as it exits the prismatic reflector 108, which may better ensure that the light L reaches the light detector 52 (FIG. 7).

Figure 23:
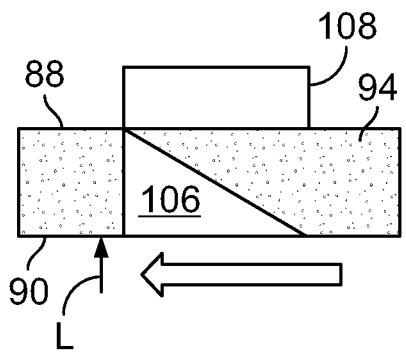
FIGS. 23-26 are diagrammatic views of the ramp and prismatic reflector of the centrifugal separation chamber passing through the path of light from the light source during a calibration phase.
Figure 27:
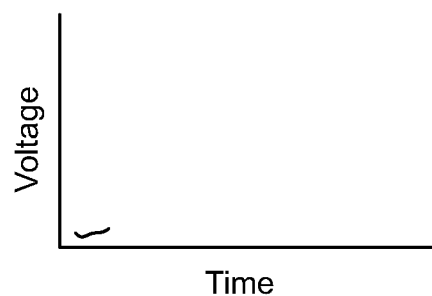
FIGS. 27-30 are diagrammatic views of the voltage output or signal transmitted by the light detector during the conditions shown in FIGS. 23-26, respectively.
Figure 24:
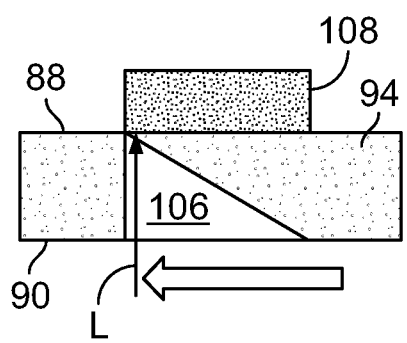

The prismatic reflector 108 may be angularly aligned with the ramp 106, such that the light L from the light source 50 will only enter into the prismatic reflector 108 when the ramp 106 has been rotated into the path of the light L. At all other times (when the ramp 106 is not in the path of the light L), the light L will not reach the prismatic reflector 108 and, thus, will not reach the light detector 52. This is illustrated in FIGS. 23-26, which show the ramp 106 and prismatic reflector 108 as the centrifugal separation chamber 36 is rotated about the rotational axis 38 (while the light source 50 remains in a fixed location). In FIG. 23, the ramp 106 and prismatic reflector 108 have not yet been rotated into the initial path of the light L from the light source 50. At this time, no light is transmitted to the light detector 52, such that the output voltage of the light detector 52 (i.e., the signal transmitted from the light detector 52 to the controller 18) is in a low- or zero-state (FIG. 27).

Figure 28:
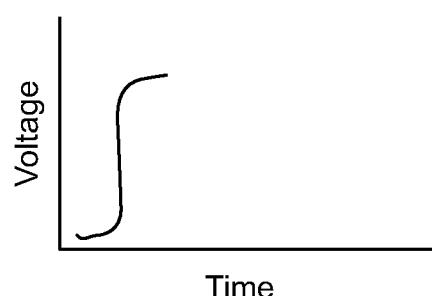

Upon the ramp 106 first being rotated into the initial path of the light L from the light source 50 (FIG. 24), the light L will begin to reach the prismatic reflector 108, which directs the light L to the light detector 52. This causes the voltage output of the light detector 52 (i.e., the signal transmitted from the light detector 52 to the controller 18) to increase to a non-zero value or state, as shown in FIG. 28.

Figure 25:
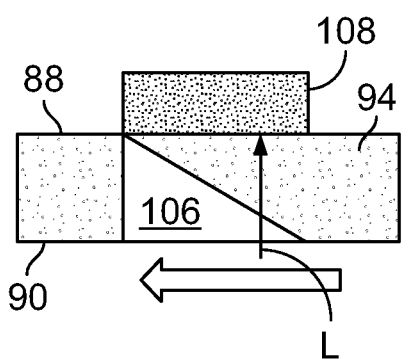
Figure 29:
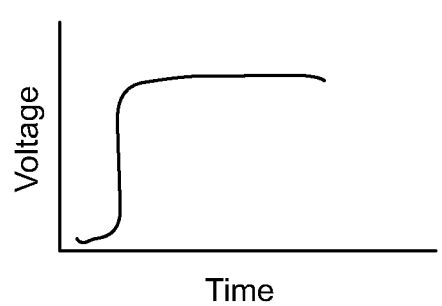
Figure 26:
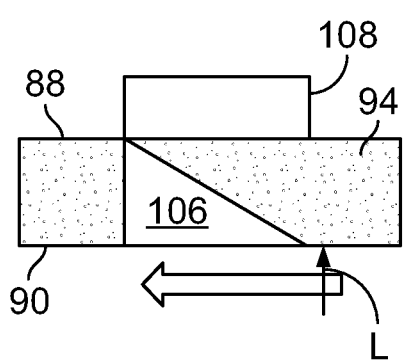

During a calibration phase, the channel 94 is filled with a fluid that will transmit the light L rather than absorbing or reflecting the light or otherwise preventing the light L from reaching the prismatic reflector 108, such that the voltage output of the light detector 52 will remain generally constant as the ramp 106 and prismatic reflector 108 are rotated through the initial path of the light L from the light source 50 (FIGS. 25 and 29). Such a calibration phase may coincide with a priming phase during which saline is pumped through the fluid flow circuit 12 to prime the fluid flow circuit 12 or may comprise a separate phase. A calibration phase may be useful in ensuring the proper operation of the light source 50 and the light detector 52, standardizing the readings taken during a separation procedure in case of any irregularities or imperfections of the centrifugal separation chamber 36, and establishing a baseline value for the signal transmitted from the light detector 52 to the controller 18 when the ramp 106 and prismatic reflector 108 are aligned with the light source 50. As will be described in greater detail, the voltage output of the light detector 52 will typically not remain constant as the ramp 106 and prismatic reflector 108 are rotated through the initial path of the light L from the light source 50 because the different fluid layers displayed on the ramp 106 will allow different amounts of light L to reach the prismatic reflector 108.

Figure 30:
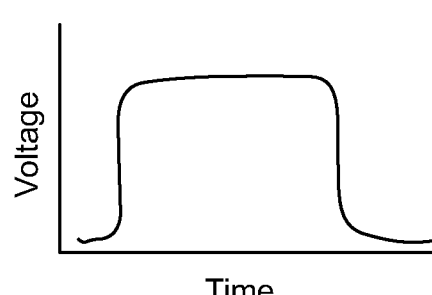
Figure 31:
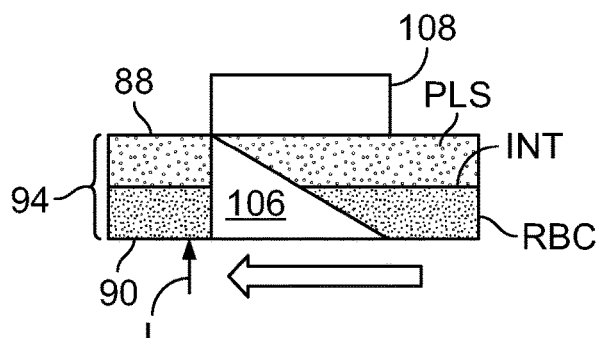
FIGS. 31-34 are diagrammatic views of the ramp and prismatic reflector passing through the path of light from the light source during a separation procedure.

The ramp 106 and prismatic reflector 108 are eventually rotated out of alignment with the light source 50 (FIG. 26), at which time no light L will reach the prismatic reflector 108 and the voltage output of the light detector 52 will return to its low- or zero-state (FIG. 30).

It may be advantageous for the light L to have a relatively small diameter for improved resolution of the signal that is generated by the light detector 52.

2. Exemplary Interface Detection and Correction Procedure

During separation of blood within the channel 94, the light L from the light source 50 travels through a light-transmissive portion of the outer side wall portion 90 and the ramp 106 to intersect the separated blood components thereon when the ramp 106 has been rotated into the initial path of the light L. After passing through the ramp 106, the light continues through the channel 94 and the fluids in the channel 94. At least a portion of the light L (i.e., the portion not absorbed or reflected by the fluids) exits the channel 94 by striking and entering a light-transmissive portion of the inner side wall portion 88. The light L passes through the inner side wall portion 88 and enters the prismatic reflector 108, which redirects the light L from its initial path to the light detector 50, as described above. Thus, it will be seen that the light L reaches the light detector 52 after intersecting and traveling through the separated blood components in the channel 94 only once, in contrast to known systems in which light from a light source travels through a ramp and a fluid-filled channel before being reflected back through the channel to reach a light detector. Requiring the light L to traverse the fluid-filled channel 94 only once before reaching the light detector 52 instead of twice may be advantageous in that it tends to increase the intensity of the light L that reaches the light detector 52, which may improve monitoring and correction of the interface location.

The light detector 52 generates a signal that is transmitted to the interface control module of the controller 18, which can determine the location of the interface INT on the ramp 106. In one embodiment, the location of the interface INT is associated with a change in the amount of light L that is transmitted through the less optically dense layer PLS and the optically dense layer RBC. For example, the light source 50 may be configured to emit a light L that is more readily transmitted by platelet-rich plasma or platelet-poor plasma than by red blood cells, such as red visible light (from a laser or a differently configured light source 50), which is substantially absorbed by red blood cells. The less optically dense layer PLS and the optically dense layer RBC each occupy a certain portion of the ramp 106, with the light detector 52 receiving different amounts of light L depending on whether the light L travels through the less optically dense layer PLS on the ramp 106 or the optically dense layer RBC on the ramp 106. The percentage of the ramp 106 occupied by each layer is related to the location of the interface INT in the channel 94. Thus, by measuring the amount of time that the voltage output or signal from the light detector 52 is relatively high (corresponding to the time during which the light L is passing through only the less optically dense layer PLS on the ramp 106), the controller 18 may determine the location of the interface INT and take steps to correct the location of the interface INT, if necessary.

Figure 32:
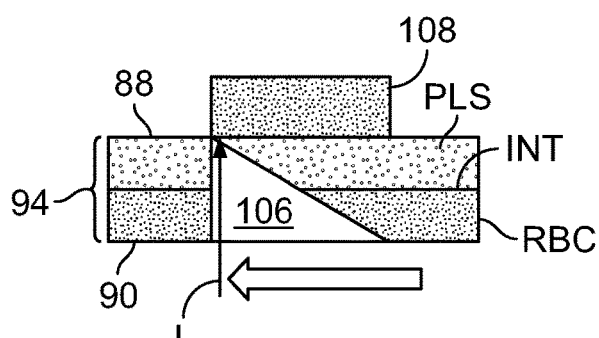
Figure 33:
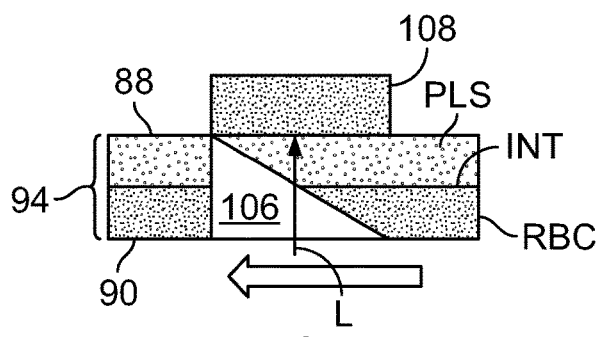
Figure 34:
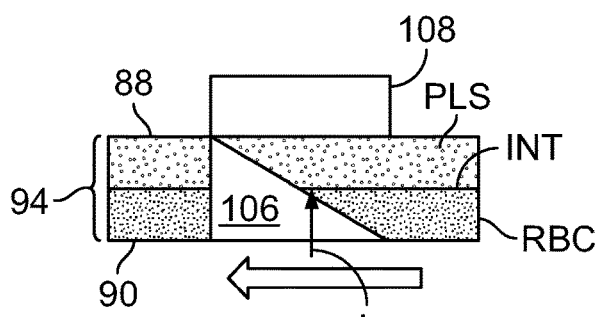

FIGS. 31-34 show a portion of the ramp 106 being rotated into and through the initial path of the light L from the light source 50. Four specific events are shown: just before the ramp 106 is rotated into the path of the light L (FIG. 31), the ramp 106 first being rotated into the path of the light L (FIG. 32), just before the interface INT displayed on the ramp 106 is rotated into the path of the light L (FIG. 33), and just after the interface INT is rotated into the path of the light L (FIG. 34). FIGS. 35-38 respectively illustrate the voltage output of the light detector 52 (corresponding to the signal that it transmits to the controller 18) during each of these events.

Figure 35:
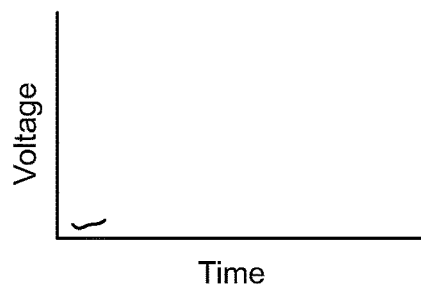
FIGS. 35-38 are diagrammatic views of the voltage output or signal transmitted by the light detector during the conditions shown in FIGS. 31-34, respectively.

As described above, the light detector 52 will receive no light L from the light source 50 when the prismatic reflector 108 is out of alignment with the initial path of the light L from the light source 50, as shown in FIG. 29. FIG. 35 shows that the output voltage of the light detector 52 (i.e., the signal transmitted from the light detector 52) to the controller 18) at this time is in a low- or zero-state.

When the ramp 106 is first rotated into the path of light L from the light source 50 (FIG. 32), the light detector 52 may begin receiving light L. The amount of light L received by the light detector 52 depends upon the fluid on the ramp 106 encountered by the light L (i.e., the fluid in the channel 94 between the ramp 106 and the inner side wall portion 88 that the light L must traverse before being directed to the light detector 52). As described above, the less optically dense layer PLS occupies a certain percentage of the channel 94 adjacent to the inner side wall portion 88, while the optically dense layer RBC occupies a certain percentage of the channel 94 adjacent to the outer side wall portion 90 (with the interface INT positioned at the transition between the two separated blood component layers). The illustrated ramp 106 is closest to the inner side wall portion 88 at its left end (in the orientation of FIGS. 31-34), while being farther spaced from the inner side wall portion 88 at its right end. At and adjacent to its left end, the ramp 106 will display only the fluid positioned closest to the inner side wall portion 88 (i.e., the less optically dense layer PLS), while the ramp 106 will display only the fluid positioned closest to the outer side wall portion 90 (i.e., the optically dense layer RBC) at and adjacent to its right end, as shown in FIGS. 31-34. At some point between its ends, the angled ramp 106 will be at a radial position where it will display the transition between the less optically dense layer PLS and the optically dense layer RBC (i.e., the interface INT). Hence, the location of the interface INT on the ramp 106 is dependent upon the percentage of the width of the ramp 106 that displays the less optically dense layer PLS (which is indicative of the percentage of the channel 94 occupied by the less optically dense layer PLS) and the percentage of the width of the ramp 106 that displays the optically dense layer RBC (which is indicative of the percentage of the channel 94 occupied by the optically dense layer RBC). It should be understood that the percentage of the ramp 106 occupied by the less optically dense layer PLS and by the optically dense layer RBC is not necessarily equal to the percentage of the channel 94 occupied by the less optically dense layer PLS and by the optically dense layer RBC, but that the percentage of the ramp 106 occupied by a separated blood component layer may be merely indicative of the percentage of the channel 94 occupied by that separated blood component layer.

Figure 36:
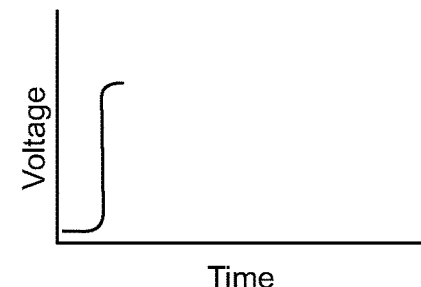

In such an embodiment, as the ramp 106 is rotated into the path of the light L from the light source 50, the light L will first encounter the portion of the ramp 106 that is positioned closest to the inner side wall portion 88 (i.e., the section of the ramp 106 that most restricts the channel 94), as shown in FIG. 32. As described above, the less optically dense layer PLS will be positioned adjacent to the inner side wall portion 88 as it separates from the optically dense layer RBC, such that the fluid displayed on this radially innermost section of the ramp 106 (i.e., the fluid present in the channel 94 between the ramp 106 and the inner side wall portion 88) will be the less optically dense layer PLS. The light is substantially transmitted through the less optically dense layer PLS to the inner side wall portion 88, and through the light-transmissive inner side wall portion 88 to the prismatic reflector 108, which redirects the light L to the light detector 52. This causes the voltage output of the light detector 52 (i.e., the signal transmitted from the light detector 52 to the controller 18) to increase to a non-zero value or state, as shown in FIG. 36. Depending on the nature of the light L, the amount of light L received by the light detector 52 (and, hence, the magnitude of the voltage output) after the light L has passed through the less optically dense layer PLS may be greater than, less than, or equal to the amount of light L received by the light detector 52 after passing through saline during the calibration phase described above.

Figure 37:
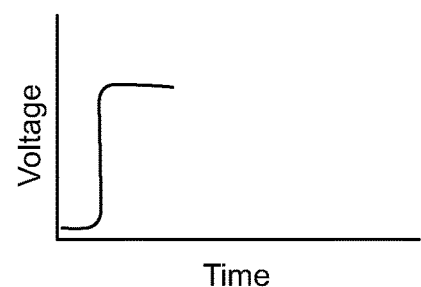

Further rotation of the ramp 106 through the path of light L from the light source 50 exposes the light L to portions of the ramp 106 that are increasingly spaced from the inner side wall portion 88 (i.e., the light L travels through portions of the channel 94 that are less restricted by the ramp 106 as the ramp 106 is rotated through the path of the light L). Up until the time that the interface INT on the ramp 106 is rotated into the path of the light L (as shown in FIG. 33), the only fluid in the channel 94 that the light L will have passed through will be the less optically dense layer PLS, such that a generally uniform level of light reaches the light detector 52 between the conditions shown in FIGS. 32 and 33. Accordingly, the voltage output of the light detector 52 will be generally uniform (at an elevated level) the whole time that the ramp 106 passes through the path of the light L before being exposed to the interface INT, as shown in FIG. 37. The controller 18 may be programmed and/or configured to consider a signal that deviates from a maximum signal level (e.g., a 10% decrease) to be part of the elevated signal for purposes of calculating the pulse width of the signal. The controller 18 will treat a greater deviation (i.e., a greater decrease in the magnitude of the signal) as the end of the elevated signal for purposes of calculating the pulse width of the signal.

Just after the interface INT has been rotated into the path of light L from the light source 50, the light L will begin to encounter the optically dense layer RBC in the channel 94, as shown in FIG. 34). As described above, the optically dense layer RBC will be positioned adjacent to the outer side wall portion 90 as it separates from the less optically dense layer PLS, such that the optically dense layer RBC will not be displayed on the ramp 106 until the ramp 106 is spaced a greater distance away from the inner side wall portion 88 (i.e., toward the right end of the ramp 106 in the orientation of FIGS. 31-34). Less light L is transmitted through the optically dense layer RBC than through the less optically dense layer PLS (which may include all or substantially all of the light L being absorbed by the optically dense layer RBC), such that the amount of light L that reaches the light detector 52 will decrease compared to the amount of light L that reaches the light detector 52 while traveling through only the less optically dense layer PLS in the channel 94 (FIGS. 32 and 33).

Figure 38:
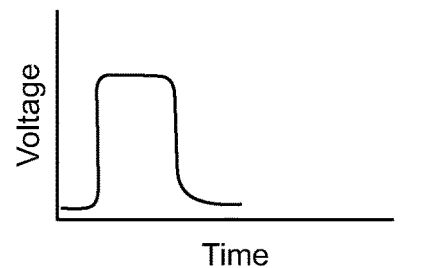

When receiving less light L, the voltage output or signal from the light detector 52 will decrease to a lower level than when the light L was passing through only the less optically dense layer PLS in the channel 94, as shown in FIG. 38. When the light L encounters the optically dense layer RBC in the channel 94, the light detector 52 may be generating a signal or voltage output that is approximately equal to its zero-state (as in FIG. 35, when the light detector 52 is receiving no light L) or a signal or voltage output that is some degree less than the magnitude of the signal or voltage output generated while the light L encounters only the less optically dense layer PLS in the channel 94. The controller 18 may be programmed and/or configured to recognize this lower level signal as representing the presence of the optically dense layer RBC on the ramp 106 (and in the portion of the channel 94 being traversed by the light L) and treat this lower level signal as the end point of the elevated signal generated by the light detector 52 while light L passes through only the less optically dense layer PLS in the channel 94.

Figure 39:
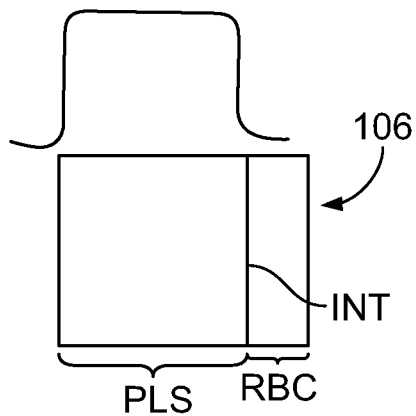
FIGS. 39 and 40 are diagrammatic views of separated blood components on the ramp and the pulse widths of a signal generated by the light detector for each condition.
Figure 40:
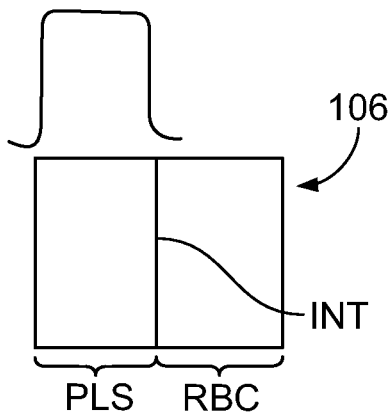

Thus, the pulse width of the elevated signal from the light detector 52 to the controller 18 (i.e., the time during which light L is traversing only the less optically dense layer PLS in the channel 94) is determined by the percentages of the ramp 106 that are occupied by the less optically dense layer PLS and the optically dense layer RBC. Accordingly, a greater pulse width of the signal from the light detector 52 to the controller 18 is associated with the less optically dense layer PLS occupying a larger portion of the ramp 106 (as shown in FIG. 39 from the point of view of the light source 50, which may correspond to the condition shown in FIG. 19) and will be indicative of a thinner optically dense layer RBC on the ramp 106 (and in the channel 94). Conversely, a signal from the light detector 52 to the controller 18 having a narrower pulse width is associated with the less optically dense layer PLS occupying a smaller portion of the ramp 106 (as shown in FIG. 40) and will be indicative of a thicker optically dense layer RBC on the ramp 106 (and in the channel 94).

Figure 41:
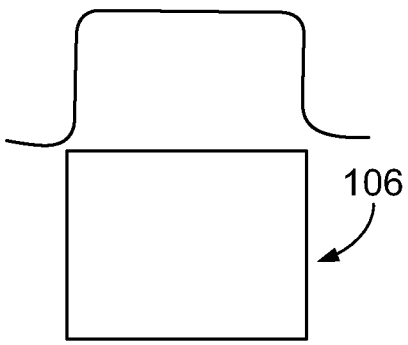
FIG. 41 is a diagrammatic view of saline on the ramp and the pulse width of a signal generated by the light detector for such a condition.

The controller 18 may compare the pulse width of the signal to the pulse width generated during the calibration phase (described above and shown in FIG. 41), which corresponds to the pulse width when light L is transmitted to the light detector 52 over the entire width of the ramp 106. The pulse width of the signal generated by the light detector 52 during the calibration phase may be referred to as the saline calibration signal. Comparing these two pulse widths will indicate the percentage of the ramp 106 that is occupied by the less optically dense layer PLS and by the optically dense layer RBC, which information the controller 18 may use to determine the location of the interface INT within the channel 94. In particular, the interface position may be calculated as follows:

$$\text{Interface position (\%)} = ((\text{saline calibration pulse width} - \text{current plasma pulse width})/\text{saline calibration pulse width})*100 \quad \text{[Equation 1]}$$

It will be seen that Equation 1 effectively calculates the percentage of the ramp 106 that is occupied by the optically dense layer RBC, as the difference between the two pulse widths corresponds to the length of time that the ramp 106 is rotated through the path of the light L without the light detector 52 received an elevated level of light L (i.e., the amount of time that the ramp 106 is rotated through the path of the light L while the optically dense layer RBC is present on the ramp 106).

Figure 42:
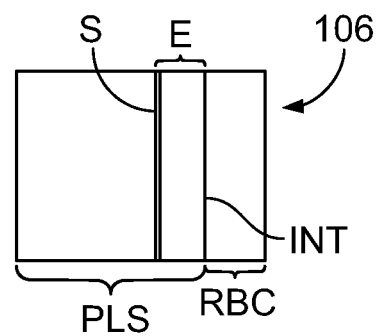
FIG. 42 is a diagrammatic view of the position of an interface between separated blood components on the ramp compared to a target interface position.

When the location of the interface INT on the ramp 106 has been determined, the interface control module compares the actual interface location with a desired interface location, which may be referred to as the setpoint S. The difference between the setpoint S and the calculated interface position may be referred to as the error signal E, which is shown in FIG. 42. It should be understood that so expressing the error signal E in terms of a targeted red blood cell percentage value (i.e., the percentage of the ramp 106 that is actually occupied by the optically dense layer RBC vs. the percentage of the ramp 106 which should be occupied by the optically dense layer RBC) is merely exemplary, and that the error signal E may be expressed or calculated in any of a number of other ways.

When the control value is expressed in terms of a targeted red blood cell percentage value, a negative error signal E indicates that the optically dense layer RBC on the ramp 106 is too large (as FIG. 19 shows). The interface control module of the controller 18 generates a signal to adjust an operational parameter accordingly, such as by reducing the rate at which platelet-rich plasma is removed through the first outlet 102 under action of a pump of the blood separation device 10. The interface INT moves toward the desired control position (as FIG. 18 shows), where the error signal is zero.

A positive error signal indicates that the optically dense layer RBC on the ramp 106 is too small (as FIGS. 20 and 42 show). The interface control module of the controller 18 generates a signal to adjust an operational parameter accordingly, such as by increasing the rate at which the plasma constituent is removed through the first outlet 102 under action of a pump of the blood separation device 10. The interface INT moves toward the desired control position (FIG. 18), where the error signal is again zero.

It should be understood that this system for controlling the location of the interface INT is merely exemplary and that differently configured and/or functioning systems may be employed without departing from the scope of the present disclosure.

III. Exemplary Separation Procedure

An exemplary blood separation procedure that may be carried out using systems and techniques according to the present disclosure will now be described.

Depending on the blood separation objectives, there is a suitable procedure for separating and collecting any of a variety of different blood components, either alone or in combination with other blood components. Accordingly, prior to processing, an operator selects the desired protocol (e.g., using an operator interface station, if provided), which informs the controller 18 of the manner in which it is to control the other components of the blood separation device 10 during the procedure.

The operator may also proceed to enter various parameters, such as information regarding the blood source. In one embodiment, the operator also enters the target yield for the various blood components (which may also include entering a characteristic of the blood, such as a platelet pre-count) or some other collection control system (e.g., the amount of whole blood to be processed).

If there are any fluid containers (e.g., a storage solution container) that are not integrally formed with the fluid flow circuit 12, they may be connected to the fluid flow circuit 12 (e.g., by piercing a septum of a tube of the fluid flow circuit 12 or via a luer connector), with the fluid flow circuit 12 then being mounted to the blood separation device 10 (including the fluid containers F1-F7 being hung from the weight scales W1-W6 and the hooks or supports H1 and H2, as appropriate). An integrity check of the fluid flow circuit 12 may be executed by the controller 18 to ensure the various components are properly connected and functioning. Following a successful integrity check, the blood source is connected to the fluid flow circuit 12 and the fluid flow circuit 12 may be primed (e.g., by saline pumped from a saline bag F2 by operation of one or more of the pumps P1-P6 of the blood separation device 10).

When the fluid flow circuit 12 has been primed, blood separation may begin. The stages of blood separation vary depending on the particular procedure, and will be described in greater detail below.

A. T-Cell Lymphocyte Collection

According to one aspect of the present disclosure, the blood separation device 10 may be used to separate and collect mononuclear cells and T-cell lymphocytes as an MNC product. Following collection, the MNC product may be mixed with a formulation containing genetic material and passed through an electroporation device, which enables genetic editing of the T-cells of the MNC product. The MNC product may be washed before and/or after being passed through the electroporation device.

1. Fluid Flow Circuit

FIG. 2 is a schematic view of an exemplary fluid flow circuit 12 having a pair of blood access devices (e.g., needles) for separating and collecting mononuclear cells and T-cell lymphocytes from blood as an MNC product. The fluid flow circuit 12 includes a cassette 48 of the type described above and illustrated in FIG. 4, which connects the various components of the fluid flow circuit 12. The various connections amongst the components of the fluid flow circuit 12 are shown in FIG. 2, which also shows the fluid flow circuit 12 mounted to the blood separation device 10.

Components of the fluid flow circuit 12 interact with many of the components of the blood separation device 10, as will be described, but there are selected components of the blood separation device 10 that are not used in separating and collecting mononuclear cells and T-cells using the fluid flow circuit 12 of FIG. 2. Most notably, one of the pressure sensors A3 is not used in the procedure described herein. The fluid flow circuit 12 includes a fluid container F3 (which may be referred to as a first waste bag) that, in the illustrated procedures of FIGS. 43-58, is only used during the preprocessing priming phase, in which saline from the saline bag F2 is pumped through the fluid flow circuit 12 to prime it, before being conveyed to the first waste bag F3 for disposal at the end of the procedure.

2. MNC Collection Phase

Figure 43:
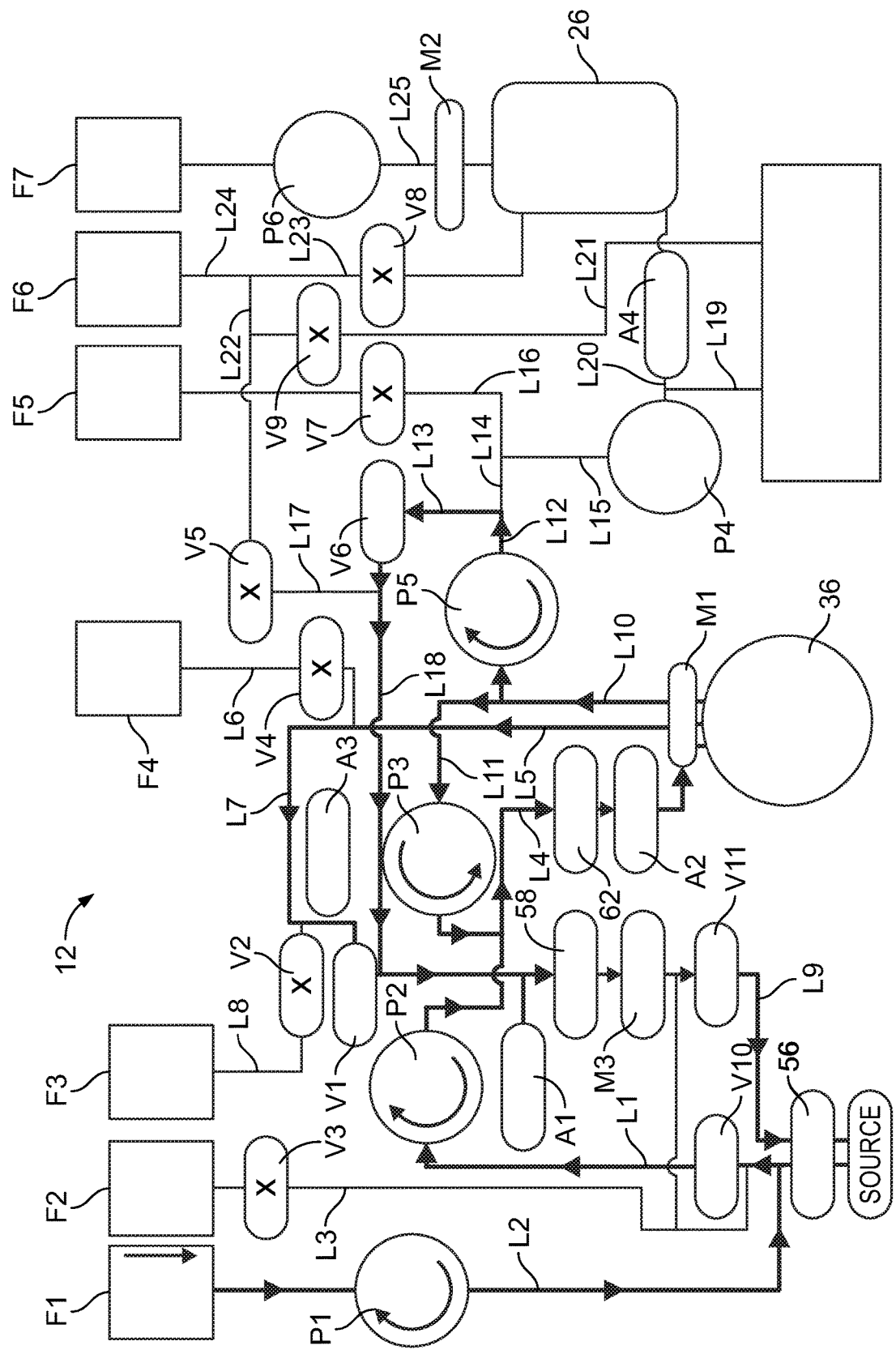
FIGS. 43-58 are schematic views of the fluid circuit of FIG. 2, showing the system carrying out different fluid flow tasks in connection with separation and collection of mononuclear cells and T-cells, followed by genome editing and (optionally) washing of the T-cells.

Blood is drawn into the fluid flow circuit 12 from a blood source (e.g., using a needle) via line L1, as shown in FIG. 43. The line L1 may include a manual clamp 56 that may initially be in a closed position to prevent fluid flow through the line L1. When processing is to begin, an operator may move the manual clamp 56 from its closed position to an open position to allow fluid flow through the line L1.

The blood is drawn into the line L1 by the source pump P2. Anticoagulant from the anticoagulant bag F1 may be added to the blood via line L2 by action of the anticoagulant pump P1. The valve V10 associated with valve station C10 is open to allow flow through line L1, while the valve V3 associated with valve station C3 is closed to prevent flow through line L3, thereby directing the blood toward the centrifugal separation chamber 36 via lines L1 and L4. Prior to reaching the centrifugal separation chamber 36, the blood may pass through the air trap 62, the sensor station S2 associated with pressure sensor A2, and the centrifugal separator sensor M1. The centrifugal separator sensor M1 may detect the hematocrit of the fluid entering the centrifugal separation chamber 36 (which may be used to set the flow rate of the plasma pump P5), while the pressure sensor A2 may monitor the pressure in the centrifugal separation chamber 36.

The centrifugal separator 16 of the blood separation device 10 manipulates the centrifugal separation chamber 36 of the fluid flow circuit 12 to separate the blood in the centrifugal separation chamber 36 into platelet-rich plasma and packed red blood cells, with a mononuclear cell-containing layer or interface positioned therebetween. While the interface is referred to herein as the mononuclear cell-containing layer, it should be understood that it also contains T-cell lymphocytes, which are to be collected with the mononuclear cells as an MNC product. Granulocytes may tend to move into the same layers as the packed red blood cells, rather than remaining in the mononuclear cell-containing layer. In one embodiment, the centrifugal separation chamber 36 is rotated nominally at 4,500 rpm, but the particular rotational speed may vary depending on the flow rates of fluids into and out of the centrifugal separation chamber 36.

The packed red blood cells (and granulocytes) exit the centrifugal separation chamber 36 via line L5. The valve V4 associated with line L6 is closed, such that the packed red blood cells are directed through line L7. Valve V2 associated with line L8 is closed, while valve V1 is open to direct the packed red blood cells through line L9, the return line filter 58, air detector M3, and the valve station C11 associated with open valve V11 on their way to a recipient (which is typically the blood source).

Platelet-rich plasma is drawn out of the centrifugal separation chamber 36 via line L10 by the combined operation of the recirculation pump P3 and the plasma pump P5. The platelet-rich plasma travels through line L10 until it reaches a junction, which splits into lines L11 and L12. The recirculation pump P3, which is associated with line L11, redirects a portion of the platelet-rich plasma to a junction, where it mixes with blood in line L4 that is being conveyed into the centrifugal separation chamber 36 by the source pump P2. Recirculating a portion of the platelet-rich plasma into the centrifugal separation chamber 36 with inflowing blood decreases the hematocrit of the blood entering the centrifugal separation chamber 36, which may improve separation efficiency of the platelets from the red blood cells. By such an arrangement, the flow rate of the fluid entering the centrifugal separation chamber 36 is equal to the sum of the flow rates of the source pump P2 and the recirculation pump P3.

As the platelet-rich plasma drawn out of the centrifugal separation chamber 36 into line L11 by the recirculation pump P3 is immediately added back into the centrifugal separation chamber 36, the bulk or net platelet-rich plasma flow rate out of the centrifugal separation chamber 36 is equal to the flow rate of the plasma pump P5. Line L12 has a junction, where it splits into lines L13 and L14, with line L14 itself including a junction, where it splits into lines L15 and L16. A valve V7 associated with valve station C7 is closed to prevent fluid flow through the line L16, while the transfer pump P4 associated with line L15 is inactive, thereby directing the separated platelet-rich plasma through line L13 and the valve station C6 associated with open valve V6. Line L13 includes a junction downstream of valve station C6, where it splits into lines L17 and L18. The valve V5 associated with valve station C5 is closed to prevent fluid flow through line L15, thereby directing the separated platelet-rich plasma through line L18. The platelet-rich plasma in line L18 combines with the packed red blood cells in line L9, with the platelet-rich plasma being conveyed to a recipient (as described above with respect to the packed red blood cells) with the packed red blood cells as a combined fluid.

The mononuclear cell-containing layer remains within the centrifugal separation chamber 36 and increases in volume throughout this phase while the packed red blood cells and the platelet-rich plasma are removed from the centrifugal separation chamber 36. This phase continues for a predetermined amount of time or until the occurrence of a predetermined event. In one embodiment, this phase continues until a predetermined volume of blood (e.g., 1,000-2,000 ml) has been processed, which is experimentally determined to be the blood volume that can be processed before mononuclear cells begin to escape the centrifugal separation chamber 36.

Figure 44:
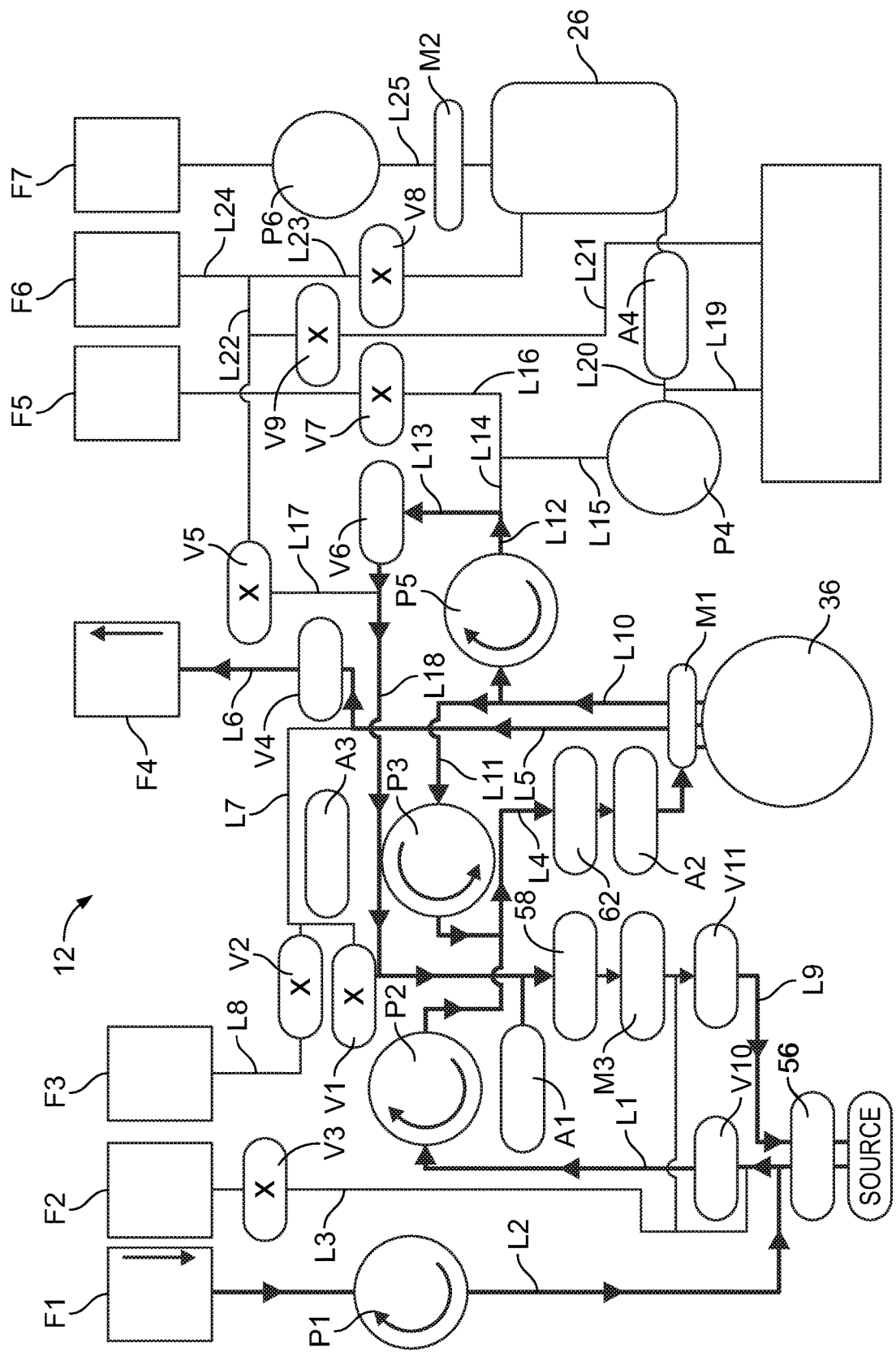

Toward the end of the MNC collection phase, the valve V1 associated with valve station C1 is closed, while the valve V4 associated with valve station C4 is opened, as shown in FIG. 44. This prevents the packed red blood cells from being conveyed to the recipient (e.g., the blood source) and instead directs the packed red blood cells through line L6 and into the red blood cell collection container F4. This phase lasts long enough to collect a specific volume of packed red blood cells, which are used to transfer the mononuclear cell-containing layer out of the centrifugal separation chamber 36, as will be described in greater detail herein. In one embodiment, approximately 50 ml of packed red blood cells is collected, although the particular volume may vary without departing from the scope of the present disclosure.

3. MNC Transfer Phase

When the target volume of packed red blood cells has been collected, the MNC transfer phase begins. This phase may begin by allowing the centrifugal separator 16 to rotate the centrifugal separation chamber 36 without flow for approximately 30-60 seconds to allow the mononuclear cell distribution along the interface between the platelet-rich plasma and the red blood cell layer in the centrifugal separation chamber 36 to stabilize.

Figure 45:
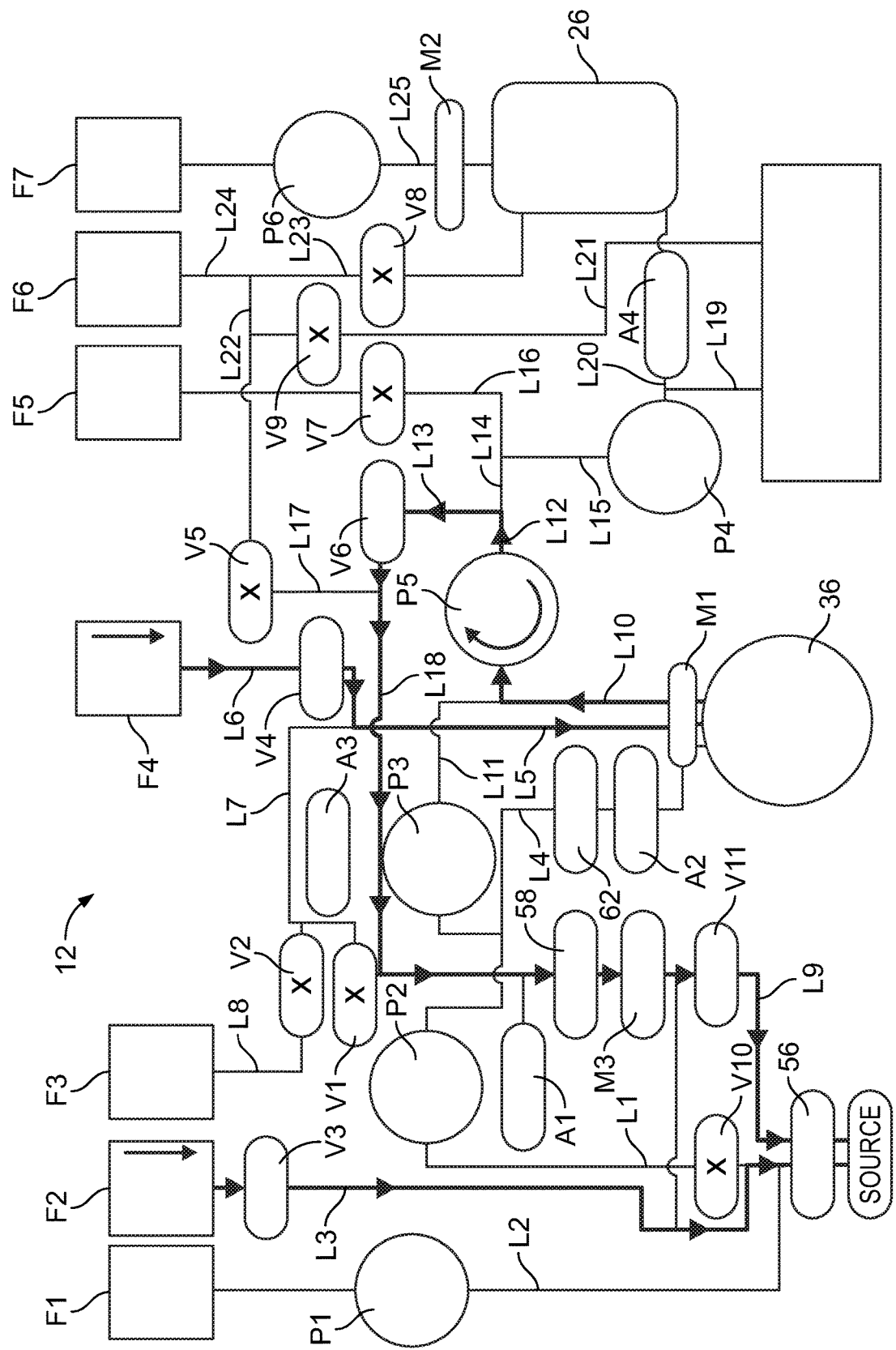

Blood draw is stopped during the MNC transfer phase by closing the valve V10 associated with valve station C10, while also ceasing operation of the anticoagulant pump P1 and the source pump P2, as shown in FIG. 45. The valve V3 associated with valve station C3 is opened to allow saline to flow out of the saline container F2 via gravity. The saline flows through line L3 and to the blood source via line L1 to prevent coagulation of any blood present in the fistula of line L1 that has not yet been anticoagulated.

To transfer the mononuclear cell-containing layer out of the centrifugal separation chamber 36, the thickness of the red blood cell layer is increased until it forces the mononuclear cell-containing layer out of the centrifugal separation chamber 36. This is done by ceasing operation of the recirculation pump P3, while the plasma pump P5 continues to operate. This pulls the packed red blood cells in the red blood cell collection container F4 via line L6. On account of valves V1 and V2 being closed, the packed red blood cells are directed back into the centrifugal separation chamber 36 via line L5 (i.e., via the red blood cell outlet).

The centrifugal separator 16 continues to rotate the centrifugal separation chamber 36 at the same speed as during the MNC collection phase (e.g., approximately 4,500 rpm), such that the returning packed red blood cells quickly increase the thickness of the red blood cell layer within the centrifugal separation chamber 36. This causes the mononuclear cell-containing layer on top of the red blood cell layer to exit the centrifugal separation chamber 36 via line L10 (i.e., the plasma outlet). It should be understood that no fluid will exit the centrifugal separation chamber 36 via line L4 (i.e., the inlet) due to the source pump P2 and the recirculation pump P3 being inactive.

The centrifugal separator sensor M1 detects the optical density and/or the redness of the fluid exiting the centrifugal separation chamber 36 via line L10. Initially, platelet-rich plasma will be exiting the centrifugal separation chamber 36 via line L10, in which case the centrifugal separator sensor M1 will observe low optical density and/or low redness. While platelet-rich plasma is exiting the centrifugal separation chamber 36 via line L10, the valve V7 associated with valve station C7 will be closed to prevent fluid flow through line L16, with the transfer pump P4 being inactive to prevent fluid flow through line L15. The valve V6 associated with valve station C6 is open, thus directing the platelet-rich plasma through line L13 for receipt by a recipient (e.g., the blood source), as described above.

Figure 46:
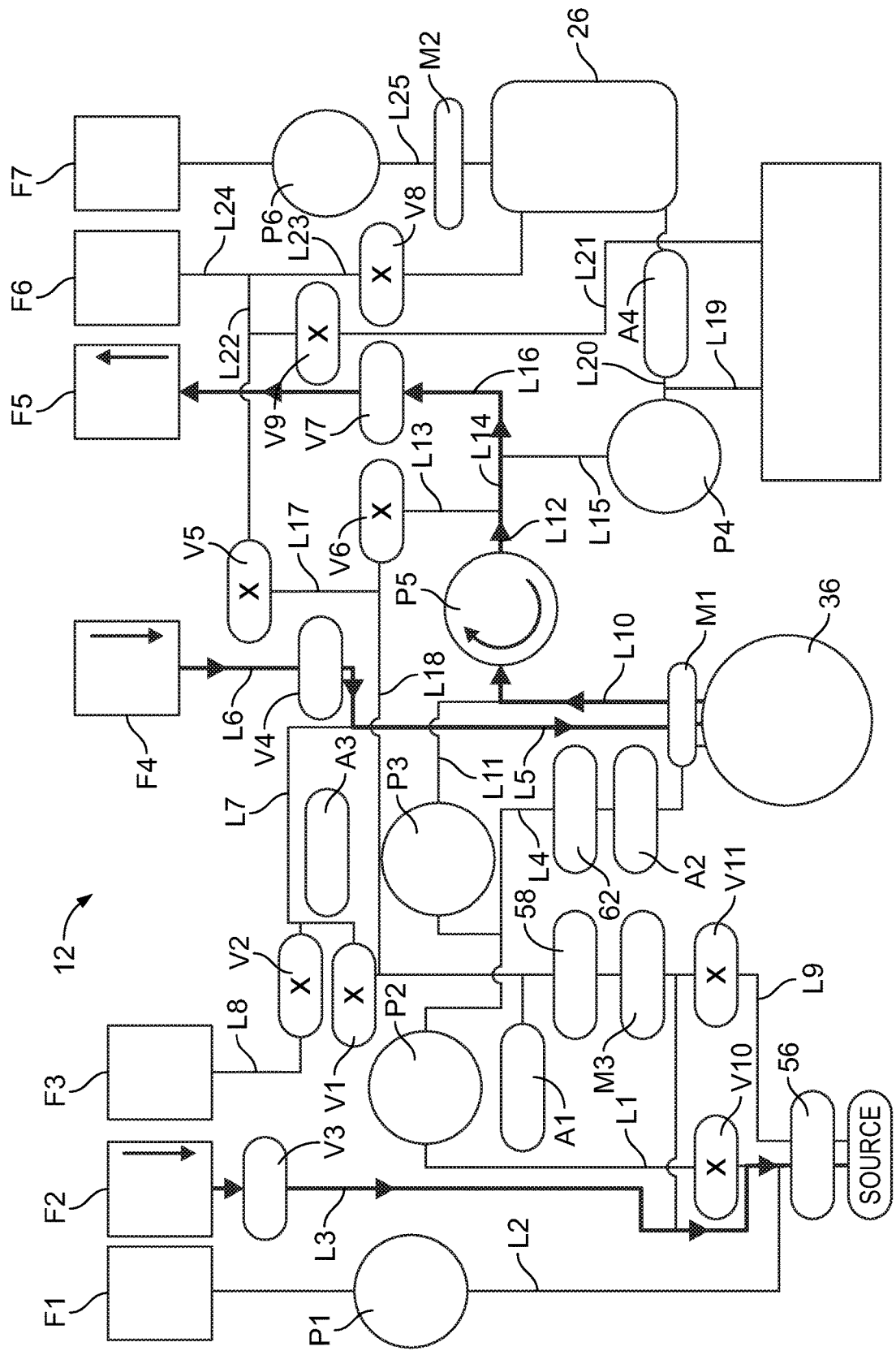

Once the centrifugal separator sensor M1 detects a sufficient number of mononuclear cells exiting the centrifugal separation chamber 36 via line L10 (which corresponds to an increase in the optical density and redness of the fluid flowing through the plasma outlet), the valve V7 associated with valve station C7 opens and the valve V6 associated with valve station C6 closes, as shown in FIG. 46. This will direct the fluid in line L10 (i.e., the mononuclear cell-containing layer) through lines L14 and L16 and into the MNC collection container F5.

Once the centrifugal separator sensor M1 detects that the fluid in line L10 is packed red blood cells (due to detection of an elevated optical density and/or redness level), this phase is ended to prevent packed red blood cells from flowing into the MNC collection container F5.

It should be noted that the collected red blood cells are conveyed into the centrifugal separation chamber 36 via the red blood cell outlet (i.e., line L5) to harvest mononuclear cells and T-cell lymphocytes. This is in contrast to conventional approaches, in which collected red blood cells instead enter a blood separation chamber via a whole blood inlet to harvest mononuclear cells. The approach described herein may be advantageous to the extent that a second inlet (or a fluid flow path between the red blood cell collection container and the whole blood inlet) are not required, which may reduce the number of components of the fluid flow circuit 12 and its complexity.

It should also be understood that operating the plasma pump P5 to pull the contents of the red blood cell collection container back into the centrifugal separation chamber 36 via the red blood cell outlet is only one possible approach. In another embodiment, a pump may be associated with line L5 to instead push the contents of the red blood cell collection container back into the centrifugal separation chamber 36 via line L5.

4. Plasma Flush Phase

Upon completion of the MNC transfer phase, lines L10 and L12 will contain mostly packed red blood cells (which were used to push the mononuclear cell-containing layer out of the centrifugal separation chamber 36), while lines L14 and L16 will contain mononuclear cells and T-cell lymphocytes that were not conveyed all the way into the MNC collection container F5. To collect the mononuclear cells and T-cells in lines L14 and L16, a plasma flush phase is executed.

Figure 47:
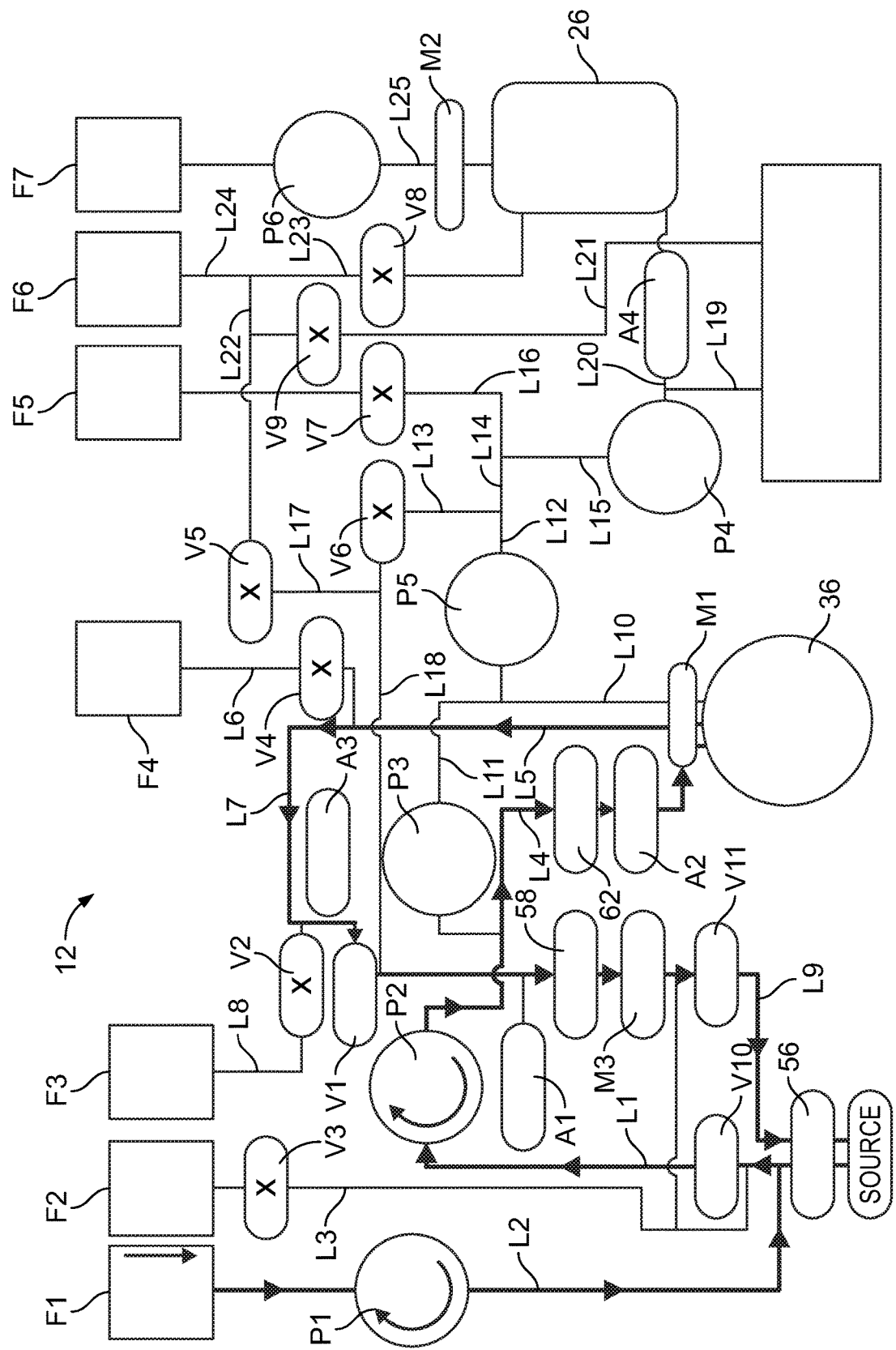

The plasma flush phase begins by first closing the valves V4 and V7 associated with valve stations C4 and C7 (respectively), opening the valve V6 associated with valve station C6, and reestablishing separation. For an initial predetermined amount of time (e.g., approximately 10-20 seconds), anticoagulated blood is drawn into the centrifugal separation chamber 36 and separated (as in the MNC collection phase of FIGS. 43 and 44), but without operation of the recirculation pump P3 and the plasma pump P5, as shown in FIG. 47. By preventing operation of the recirculation pump P3 and the plasma pump P5, fluid will only exit the centrifugal separation chamber 36 via line L5 (i.e., the red blood cell outlet). By such a configuration, the thickness of the red blood cell layer within the centrifugal separation chamber 36 will decrease.

At the end of the MNC transfer phase, the centrifugal separation chamber 36 is substantially entirely filled with packed red blood cells (in order to push the mononuclear cell-containing layer out of the centrifugal separation chamber 36). Rather than decreasing the thickness of the red blood cell layer to the level that is typically preferred during separation (e.g., in the range of approximately 50-75% of the total fluid thickness of the centrifugal separation chamber 36, as in FIG. 18), the red blood cell layer is instead brought to a lower thickness (as in FIG. 20) in order to cause platelet-poor plasma instead of platelet-rich plasma to exit the centrifugal separation chamber 36 via line L10 (i.e., the plasma outlet). The exact thickness of the red blood cell layer may vary without departing from the scope of the present disclosure, but it may be experimentally determined as the thickness at which platelet-poor plasma (instead of platelet-rich plasma) will tend to exit the centrifugal separation chamber 36 via line L10 (i.e., the plasma outlet). In one example, the thickness of the red blood cell layer is reduced to a level that is less than half of the typically preferred thickness of the red blood cell layer during separation. In another example, the thickness of the red blood cell layer is reduced to a level (e.g., approximately 20% or less of the total fluid thickness of the centrifugal separation chamber 36) that is approximately one-third of the thickness of the red blood cell layer that is typically preferred during separation (e.g., approximately 60% of the total fluid thickness of the centrifugal separation chamber 36).

Figure 48:
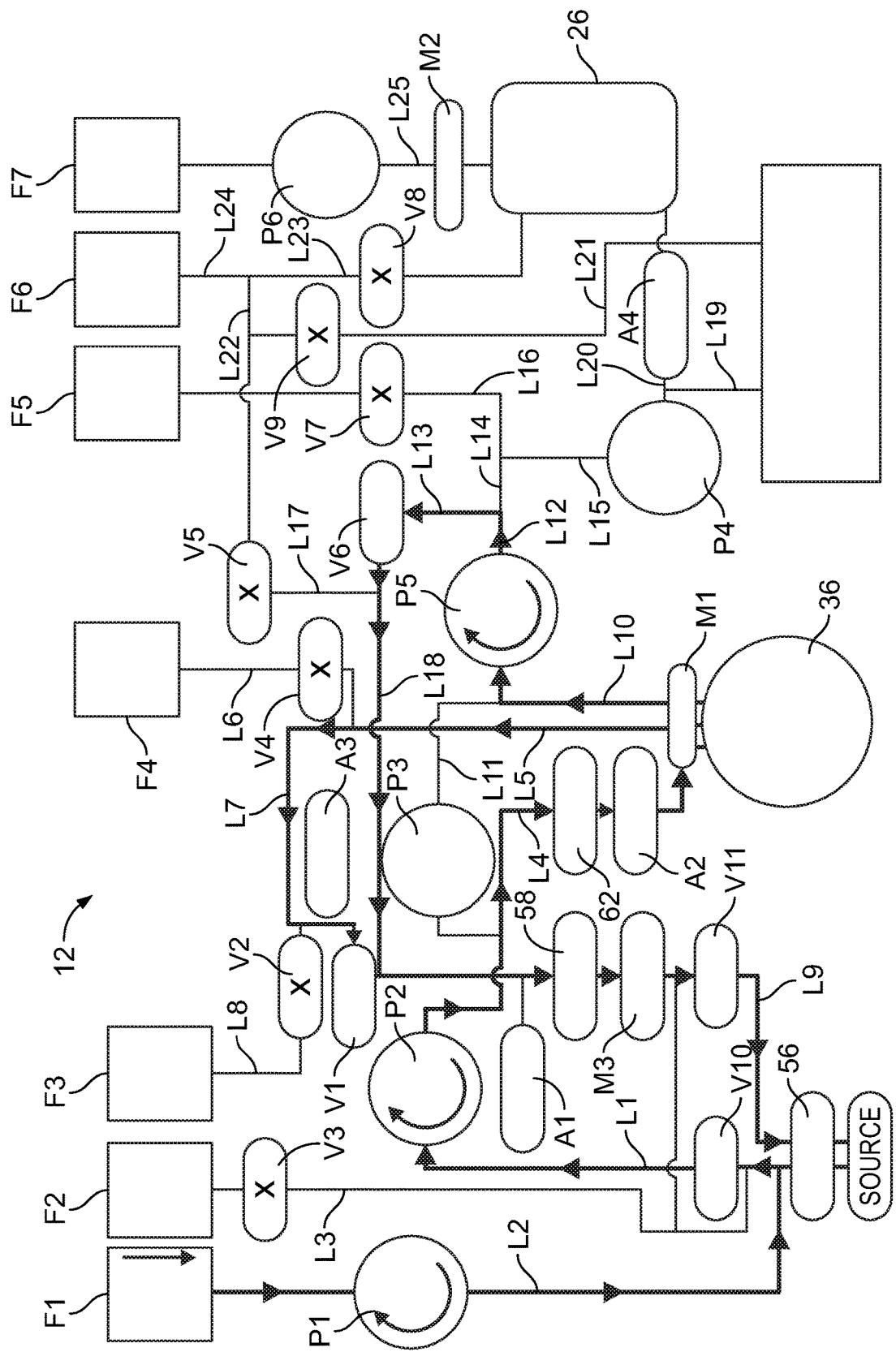

When the thickness of the red blood cell layer within the centrifugal separation chamber 36 has been reduced to a low enough level so as to produce platelet-poor plasma instead of platelet-rich plasma, the plasma pump P5 is restarted (as shown in FIG. 48). The platelet-poor plasma exiting the centrifugal separation chamber 36 via line L10 clears the packed red blood cells remaining in lines L10 and L12 at the end of the MNC transfer phase. The platelet-poor plasma pushes the packed red blood cells from lines L10 and L12 to a recipient (e.g., the blood source) via lines L13, L18, and L9.

Figure 49:
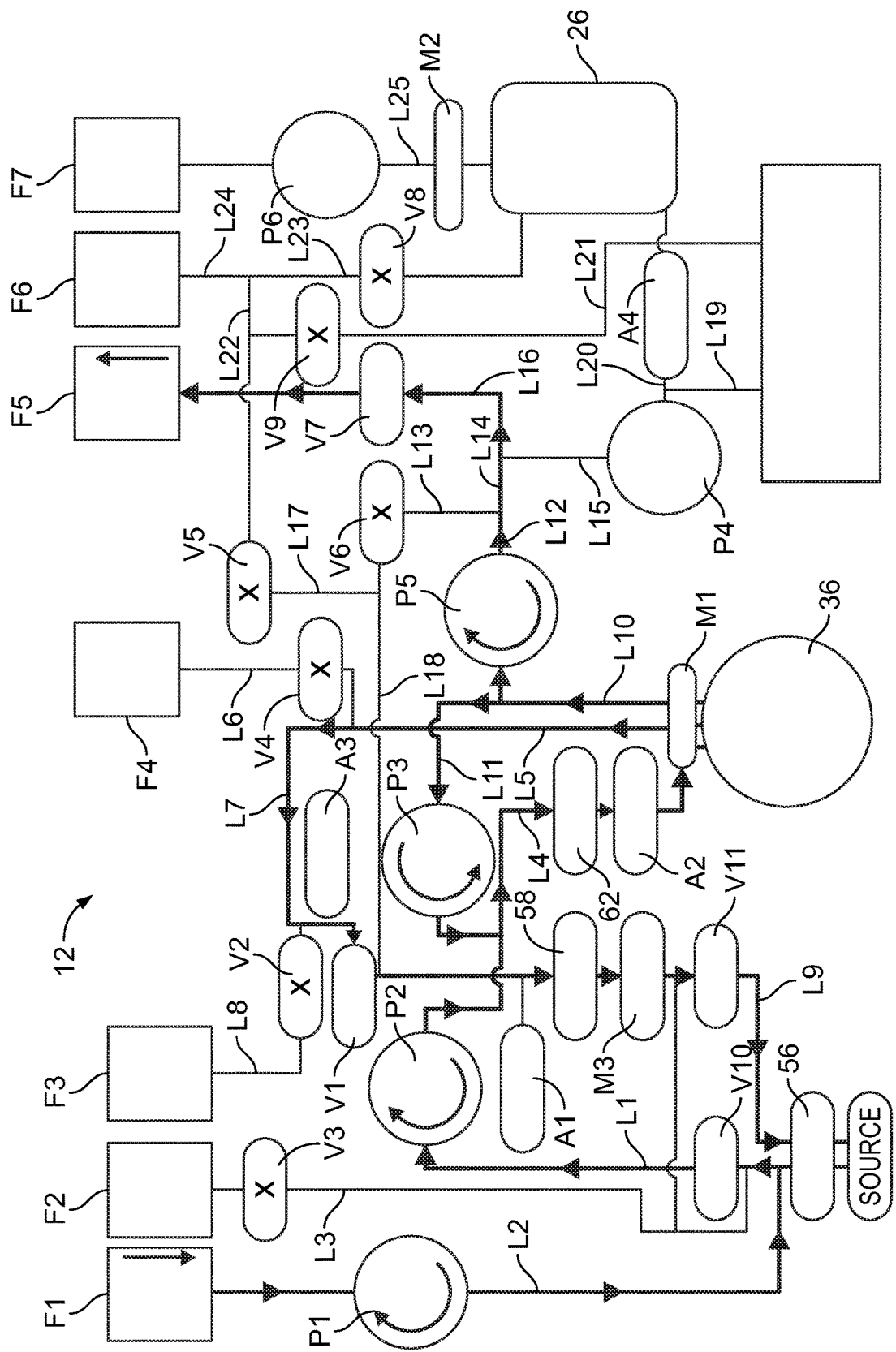

Once lines L10 and L12 are clear of packed red blood cells (which may be determined, for example, by a time delay after the centrifugal separator sensor M1 detects platelet-poor plasma flowing through line L10), the recirculation pump P3 is restarted, the valve V6 associated with valve station C6 closes (to prevent further platelet-poor plasma from flowing through line L13), and the valve V7 associated with valve station C7 opens (as shown in FIG. 49). This causes the platelet-poor plasma exiting the centrifugal separation chamber 36 via line L10 to flow through lines L12, L14, and L16, which pushes the mononuclear cells and T-cells in lines L14 and L16 (which were left there at the end of the MNC transfer phase) into the MNC collection container F5. This ensures complete collection of the mononuclear cells and T-cells, while minimizing the number of platelets transferred to the MNC collection container F5 (compared to the number of platelets that would end up in the MNC collection container F5 if platelet-rich plasma were instead used to flush the mononuclear cells and T-cells into the MNC collection container F5). This phase can also be executed at the end of collection to ensure that the MNC product in the MNC collection container F5 has the proper storage volume.

Restarting the recirculation pump P3 begins to aid in the reestablishment of steady state separation (by increasing the separation efficiency of platelets from red blood cells and by increasing the thickness of the red blood cell layer within the centrifugal separation chamber 36) if an additional amount of mononuclear cells and T-cells is to be collected (by transitioning back into an MNC collection phase and repeating the foregoing procedure). The centrifugal separator sensor M1 may be used to determine when platelet-rich plasma (instead of platelet-poor plasma) begins exiting the centrifugal separation chamber 36 via line L10, at which point the plasma flush phase transitions to an MNC collection phase and the procedure is repeated. The observed thickness of the red blood cell layer within the centrifugal separation chamber 36 may also be a factor in determining when to transition from the plasma flush phase to an MNC collection phase.

It should be noted that platelet-poor plasma created in the centrifugal separation chamber 36 during reestablishment of separation is used to flush mononuclear cells and T-cells from lines L14 and L16 into the MNC collection container F5. This is in contrast to conventional approaches, in which previously collected platelet-poor plasma is instead used to flush mononuclear cells into a collection container. The approach described herein may be advantageous to the extent that a platelet-poor plasma collection container is not required, which may reduce the number of components of the fluid flow circuit 12 and its complexity. Additionally, it is not necessary to execute a platelet-poor plasma collection phase. Furthermore, following one MNC collection cycle, separation must be reestablished in both the conventional procedure and the procedure described herein. By creating and using platelet-poor plasma during a phase that must occur regardless of the approach taken, the time required to complete the procedure may be reduced.

III. Subsequent T-Cell Processing

Figure 50:
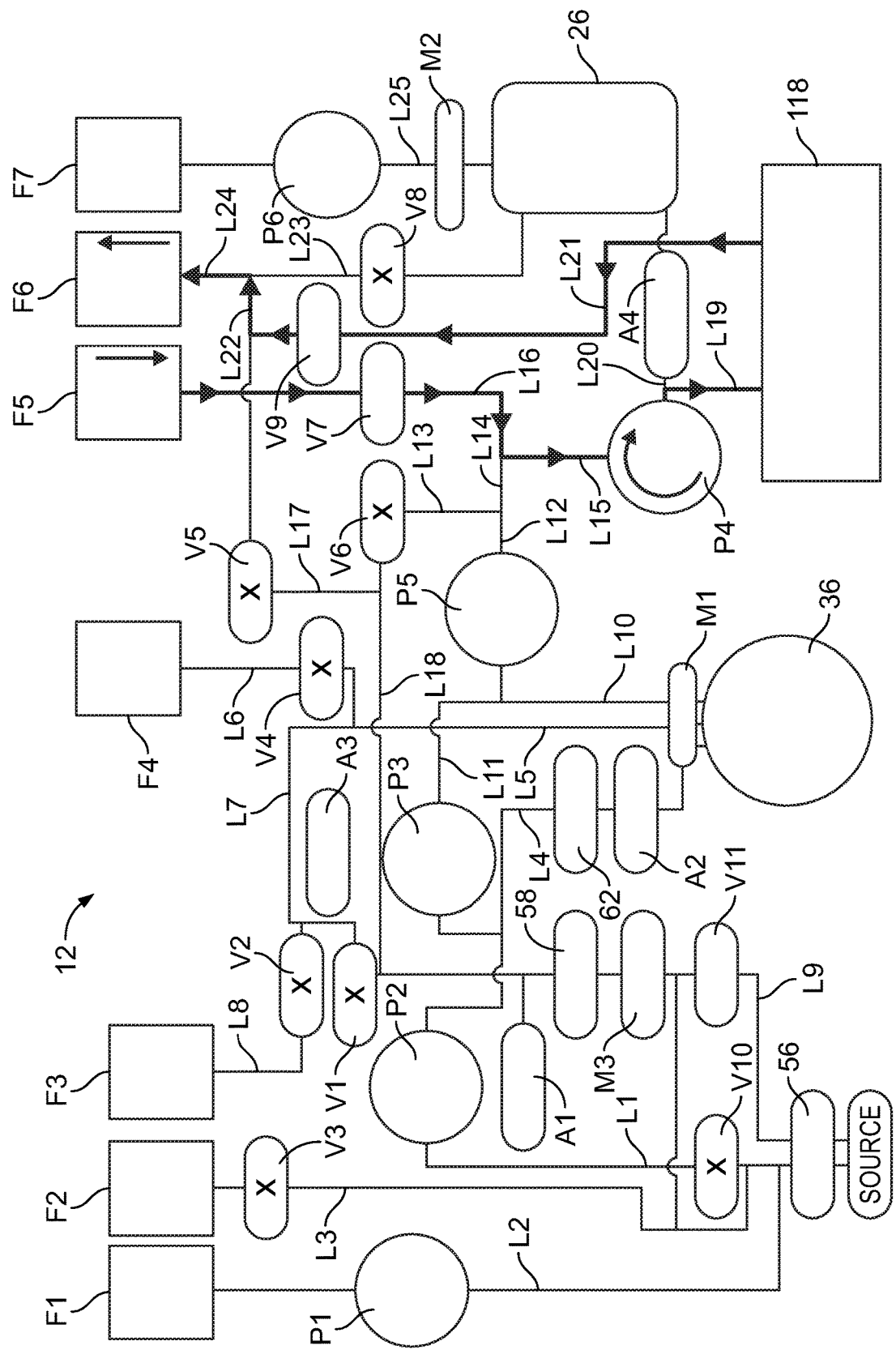
Figure 51:
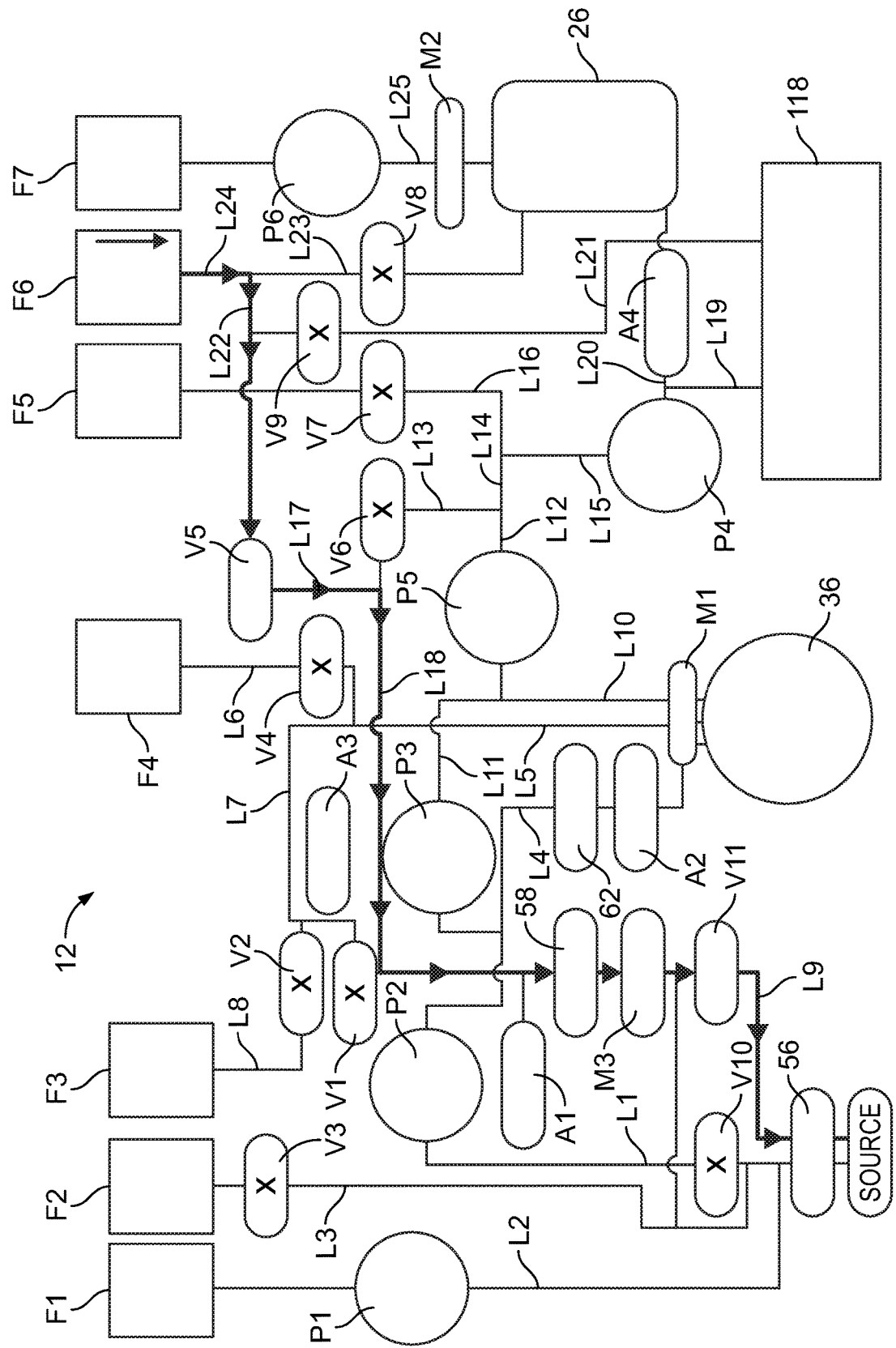

Following collection, the MNC product may be subjected to further processing, including electroporation-based treatment, such as CAR T-cell therapy. This may be carried out using a standalone, multifunctional device configured to execute the various steps of an electroporation-based treatment (including addition of DNA, electroporation, and cell washing), as is shown in FIGS. 50 and 51. Alternatively, this may be carried out using a dedicated electroporation device, which is configured only for electroporation of T-cells, with the blood separation device 10 executing the other steps of the electroporation-based treatment, as shown in FIGS. 52-58.

In either case, it will be seen that the entire process of MNC collection and subsequent processing is completed using a single, closed fluid flow circuit 12 and without disconnecting the source (e.g., a patient) from the fluid flow circuit 12 (i.e., as a "bedside" procedure). This is in contrast to a conventional approach, in which apheresis and electroporation-based processing (such as CAR T-cell therapy) take place in separate locations, with the source/patient being disconnected from an MNC product-containing fluid flow circuit during the electroporation-based treatment. It should be understood that these advantages may be realized regardless of the manner in which the MNC product is collected and is not limited to an MNC product that is separated via centrifugation or the particular process described herein. For example, some other (non-centrifuge) separation device may be used to separate the MNC product from blood prior to executing one of the electroporation-based procedures to be described.

A. Standalone, Multifunctional Device

FIGS. 50 and 51 show an MNC product being conveyed through a standalone, multifunctional device 118 (FIG. 50) and then reinfused to the blood source (FIG. 51). The exact configuration of the device 118 may vary without departing from the scope of the present disclosure, but it is configured to perform the various steps of an electroporation-based procedure (e.g., CAR T-cell therapy). This may include addition of DNA to the MNC product, electroporation of the MNC product (to open pores in a cell membrane of a T-cell, which allows the DNA to enter and modify the genome of the T-cell), and cell washing.

The manner in which the fluid flow circuit 12 is fluidly connected to the device 118 may vary according to the particular configuration of the device 118. For example, as shown in FIGS. 50 and 51, a line or tubing or conduit of the fluid flow circuit 12 may be configured to be connected to the device 118 as an inlet, with at least a portion of the MNC product flowing into the device 118 via the inlet. Another line or tubing or conduit of the fluid flow circuit 12 may be configured to be connected to the device 118 as an outlet, with the modified MNC product exiting the device 118 via the outlet. In other embodiments, the fluid flow circuit 12 may be configured as a closed system, with the fluid flow circuit 12 including a portion configured to be placed into, mounted onto, or otherwise associated with the device 118 (e.g., including one or more containers or vessels configured to be associated with the device 118), rather than a plurality of lines or tubes or conduits of the fluid flow circuit 12 being connected to the device 118.

1. Processing by Standalone, Multi-Functional Device

Regardless of the particular configuration of the standalone, multi-functional device 118, the MNC product is transferred to it from the MNC collection container F5 by operation of the transfer pump P4 (FIG. 50). The valve V7 associated with valve station C7 is opened (if not already open), while the valve V6 associated with valve station C6 is closed (if not already closed). The plasma pump P5 is inactive, thus causing the transfer pump P4 to pull the MNC product out of the MNC collection container F5 via line L16, with the MNC product moving from line L16 toward the transfer pump P4 via line L15.

Line L15 splits into lines L19 and L20 downstream of the transfer pump P4. Line L19 leads into the standalone, multi-functional device 118, while line L20 leads through the sensor station S4 associated with pressure sensor A4 and into the spinning membrane separator 26. The waste pump P6 downstream of the spinning membrane separator 26 is inactive, along with the valve V8 associated with valve station C8 being closed, which causes the MNC product in line L15 to move through line L19 into the device 118, rather than flowing through line L20.

The MNC product passes through the device 118, where it is variously processed to edit the genomes of the T-cells. The processing carried out by the device 118 may include (without being limited to) the addition of DNA, cell washing, and electroporation (in various orders). The modified MNC product exits the device 118 via line L21. The valve V9 associated with valve station C9 is open, while the valve V5 associated with valve station C5 is closed, which directs the modified MNC product through line L22 instead of through line L17. Line 22 splits into lines L23 and L24. The valve V8 associated with valve station C8 is closed, thus preventing flow through line L23, while directing the modified MNC product through line L24 and into an in-process container F6.

In an alternative embodiment, rather than conveying the modified MNC product from the device 118 into the in-process container F6, the modified MNC product may instead be conveyed from the device 118 to the source/patient via the fluid flow circuit 12.

2. Reinfusion

With the modified MNC product in the in-process container F6, the transfer pump P4 is deactivated and the valves V7 and V9 associated with valve stations C7 and C9 (respectively) are closed (FIG. 51). The valves V5 and V11 associated with valve station C5 and C11 (respectively) are opened, which allows the modified MNC product to flow out of the in-process container F6 via line L24 via gravity and through lines L22 and L17. The modified MNC product continues flowing (via gravity) through lines L18 and L9, to be reinfused to the blood source/patient. The modified MNC product may be retained in the in-process container F6 for a holding time prior to reinfusion.

B. Dedicated Electroporation Device without Cell Washing

FIGS. 52-58 show an MNC product being conveyed through a dedicated electroporation device 120 and then reinfused to the blood source. In contrast to the standalone, multifunctional device 118 of FIGS. 50 and 51, the device 120 of FIGS. 52-58 is configured solely for electroporation, while the other steps of an electroporation-based procedure are executed elsewhere (as will be described). The exact configuration of the device 120 may vary without departing from the scope of the present disclosure.

The manner in which the fluid flow circuit 12 is fluidly connected to the device 120 may vary according to the particular configuration of the device 120. For example, as shown in FIGS. 52-58, a line or tubing or conduit of the fluid flow circuit 12 may be configured to be connected to the device 120 as an inlet, with at least a portion of the MNC product flowing into the device 120 via the inlet. Another line or tubing or conduit of the fluid flow circuit 12 may be configured to be connected to the device 120 as an outlet, with the modified MNC product exiting the device 120 via the outlet. In other embodiments, the fluid flow circuit 12 may be configured as a closed system, with the fluid flow circuit 12 including a portion configured to be placed into, mounted onto, or otherwise associated with the device 120 (e.g., including one or more containers or vessels configured to be associated with the device 120), rather than a plurality of lines or tubes or conduits of the fluid flow circuit 12 being connected to the device 120.

The processing of the T-cell lymphocytes may include or omit washing of the MNC product, with cell washing (if any) taking place before and/or after the electroporation stage. An electroporation-based procedure omitting cell washing will be described first, followed by exemplary procedures including one or more cell washing stages.

1. DNA Addition

Figure 52:
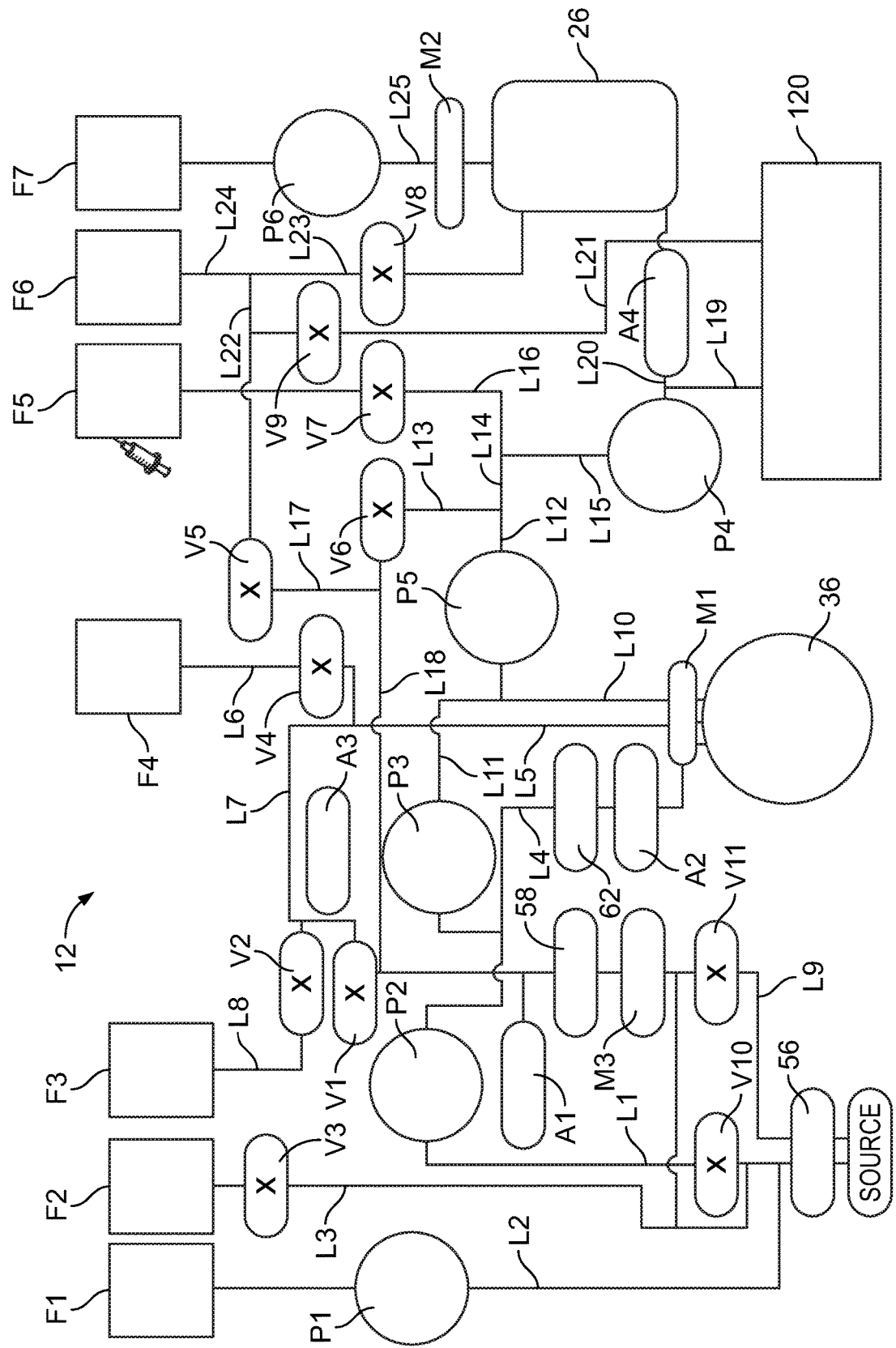

According to an exemplary procedure in which cell washing is omitted, the DNA material required to edit the genome of the T-cells of the MNC product is first added to the MNC product in the MNC collection container F5, as in FIG. 52. The nature of the DNA material may vary depending on the desired configuration of the T-cells to be modified. The DNA material may be added to the MNC collection container F5 according to any suitable approach (e.g., being injected via a port of the MNC collection container F5 either automatically under the direction of the controller 18 or manually) or may be initially provided in the MNC collection container F5 prior to association of the fluid flow circuit 12 to the blood separation device 10. In one embodiment, the MNC product and the DNA material are allowed to remain within the MNC collection container F5 for a holding time before electroporation begins.

2. Electroporation

Figure 53:
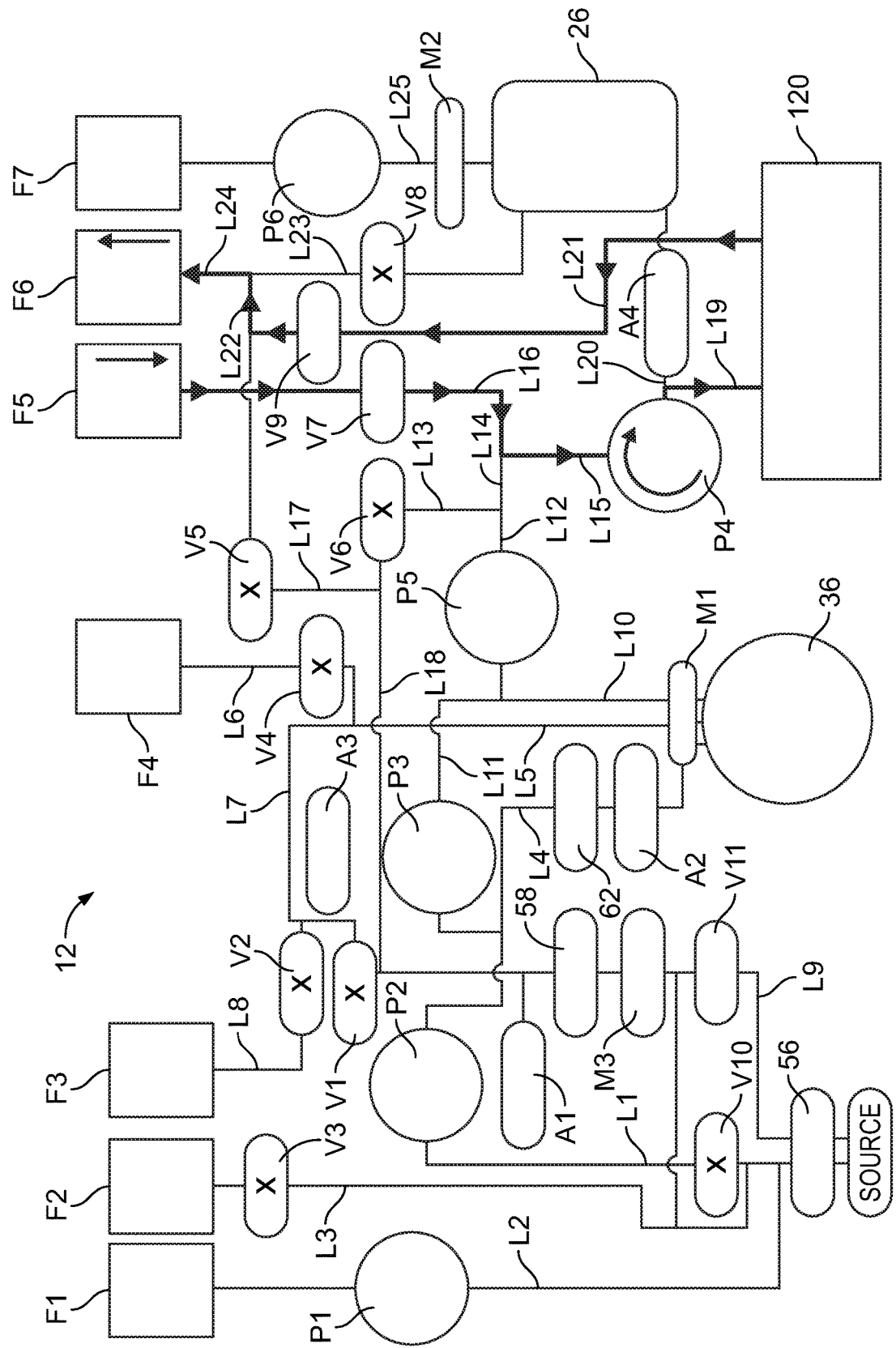

The MNC product and DNA material are transferred to the dedicated electroporation device 120 from the MNC collection container F5 by operation of the transfer pump P4 (FIG. 53). The valve V7 associated with valve station C7 is opened (if not already open), while the valve V6 associated with valve station C6 is closed (if not already closed). The plasma pump P5 is inactive, thus causing the transfer pump P4 to pull the MNC product and DNA material out of the MNC collection container F5 via line L16, with the MNC product and DNA material moving from line L16 toward the transfer pump P4 via line L15. The waste pump P6 downstream of the spinning membrane separator 26 is inactive, along with the valve V8 associated with valve station C8 being closed, which causes the MNC product and DNA material in line L15 to move through line L19 into the device 120, rather than flowing through line L20.

The MNC product and DNA material pass through the device 120, where it is subjected to electroporation, which allows for the DNA material to enter into and modify the genome of the T-cells.

The modified MNC product exits the device 120 via line L21. The valve V9 associated with valve station C9 is open, while the valve V5 associated with valve station C5 is closed, which directs the modified MNC product through line L22 instead of through line L17. The valve V8 associated with valve station C8 is closed, thus preventing flow through line L23, while directing the modified MNC product through line L24 and into the in-process container F6.

In an alternative embodiment, rather than conveying the modified MNC product from the device 120 into the in-process container F6, the modified MNC product may instead be conveyed from the device 120 to the source/patient via the fluid flow circuit 12.

3. Reinfusion

Figure 54:
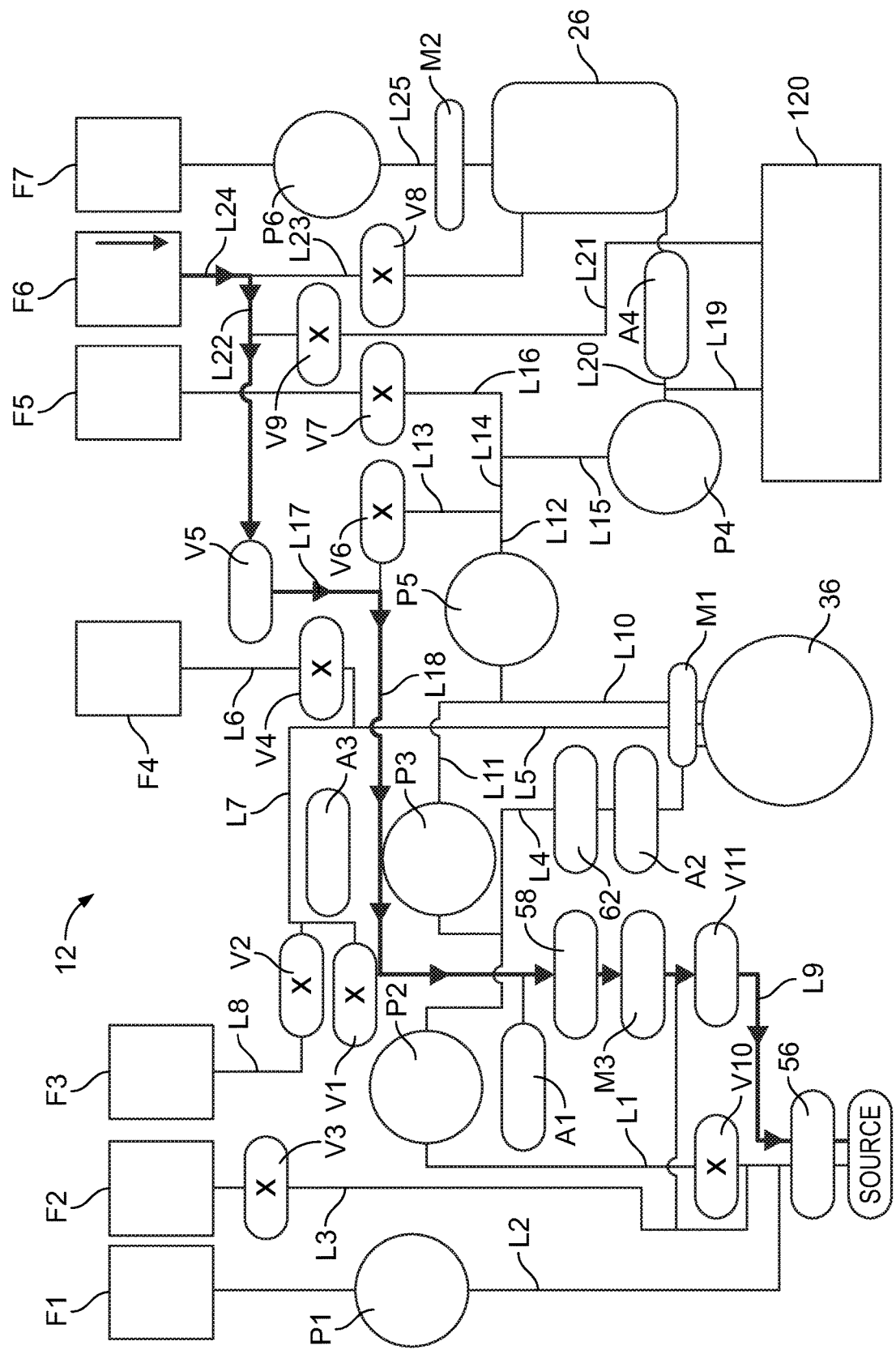

With the modified MNC product in the in-process container F6, the transfer pump P4 is deactivated and the valves V7 and V9 associated with valve stations C7 and C9 (respectively) are closed (FIG. 54). The valves V5 and V11 associated with valve stations C5 and C11 (respectively) are opened, which allows the modified MNC product to flow out of the in-process container F6 via line L24 via gravity and through lines L22 and L17. The modified MNC product continues flowing (via gravity) through lines L18 and L9, to be reinfused to the blood source/patient. The modified MNC product may be retained in the in-process container F6 for a holding time prior to reinfusion.

C. Cell Washing Prior to Electroporation

While cell washing may be omitted, there are situations in which it may be advantageous to wash the MNC product, before and/or after electroporation. Washing the MNC product prior to electroporation may be useful for reducing the plasma volume of the MNC product, replacing one cell suspension fluid (e.g., plasma) with another (e.g., a solution that enables specific actions carried out during the electroporation-based procedure), and/or removing residual cells (e.g., platelets), for example. Thus, cell washing before electroporation may be advantageous if it is deemed necessary or desirable to achieve one or more of the preceding results.

1. Cell Washing

Figure 55:
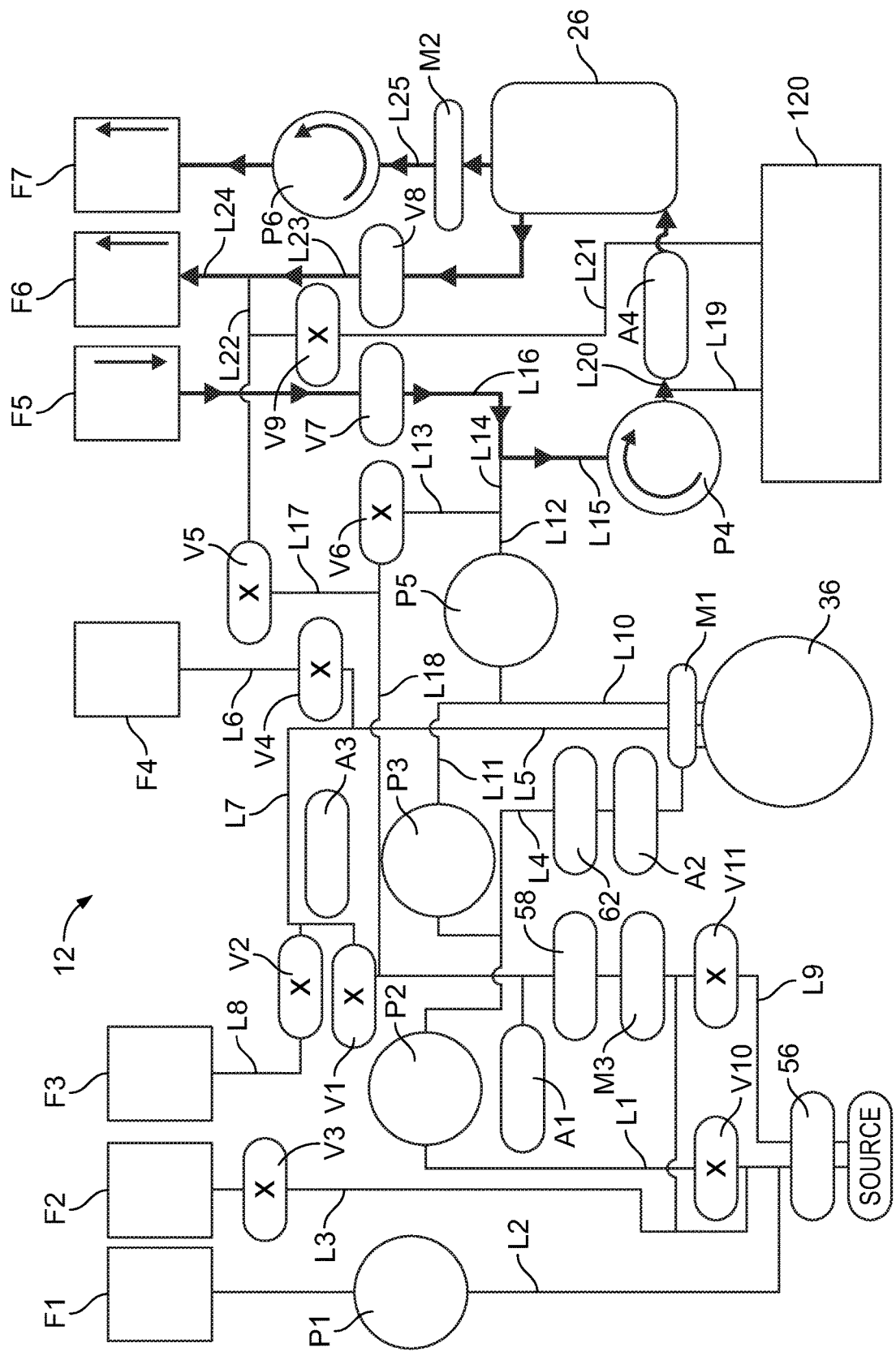

FIG. 55 shows an approach to washing the MNC product prior to electroporation. The MNC product is pulled out of the MNC collection container F5 by operation of the transfer pump P4. The valve V7 associated with valve station C7 is opened (if not already open), while the valve V6 associated with valve station C6 is closed (if not already closed). The plasma pump P5 is inactive, thus causing the transfer pump P4 to pull the MNC product out of the MNC collection container F5 via line L16, with the MNC product moving from line L16 toward the transfer pump P4 via line L15. The waste pump P6 downstream of the spinning membrane separator 26 is operative, along with the valve V8 associated with valve station C8 being open and the valve V9 associated with valve station C9 being closed, which causes the MNC product in line L15 to move through line L20 into the spinning membrane separator 26, rather than flowing through line L19 into the dedicated electroporation device 120.

The MNC product passes into the spinning membrane separator 26, which separates the MNCs and T-cells from a waste product. As described above, the nature of the waste product may vary depending on the configuration of the spinning membrane separator 26, with smaller pores filtering out supernatant and larger pores separating out supernatant and residual cell types (such as platelets and smaller red blood cells), depending on the desired composition of the washed MNC product.

The MNCs and T-cells exit the spinning membrane separator 26 via line L23, while the waste product exits the spinning membrane separator 26 via line L25 and flows into a second waste container F7. The waste product may be monitored by the spinner outlet sensor M2 to detect its optical characteristics for quality purposes (e.g., monitoring for cell loss and/or hemolysis).

The valve V8 associated with valve station C8 is open, while the valves V5 and V9 associated with valve stations C5 and C9 (respectively) are closed, thus directing the MNCs and T-cells into the in-process container F6 via lines L23 and L24 as a washed MNC product.

2. DNA Addition

Figure 56:
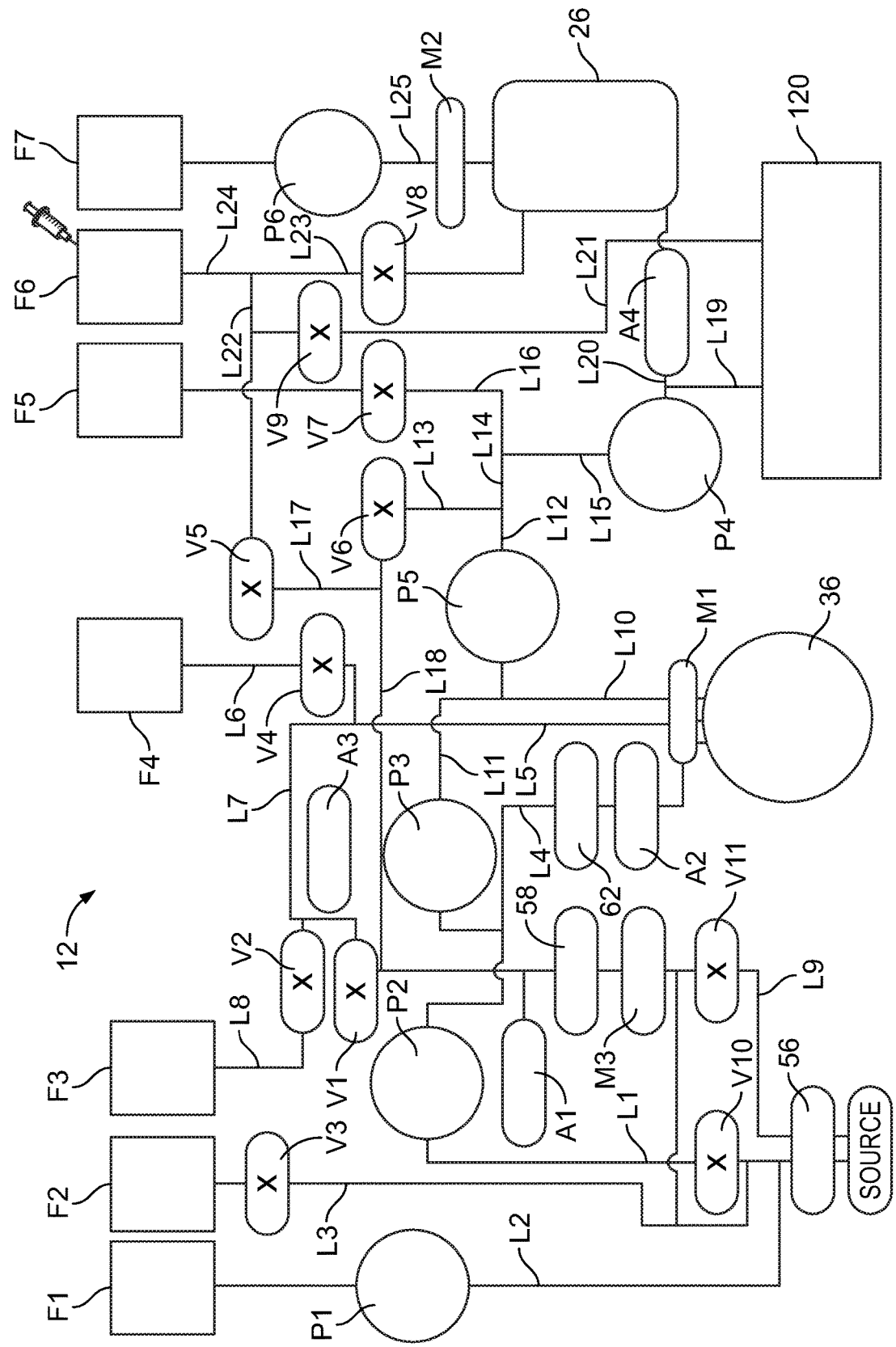

The DNA material required to edit the genome of the T-cells of the washed MNC product is added to the washed MNC product in the in-process container F6, as in FIG. 56. The nature of the DNA material may vary depending on the desired configuration of the T-cells to be modified. The DNA material may be added to the in-process container F6 according to any suitable approach (e.g., being injected via a port of the in-process container F6) or may be initially provided in the in-process container F6 prior to association of the fluid flow circuit 12 to the blood separation device 10. In one embodiment, the washed MNC product and the DNA material are allowed to remain within the in-process container F6 for a holding time before electroporation begins.

3. Electroporation

Figure 57:
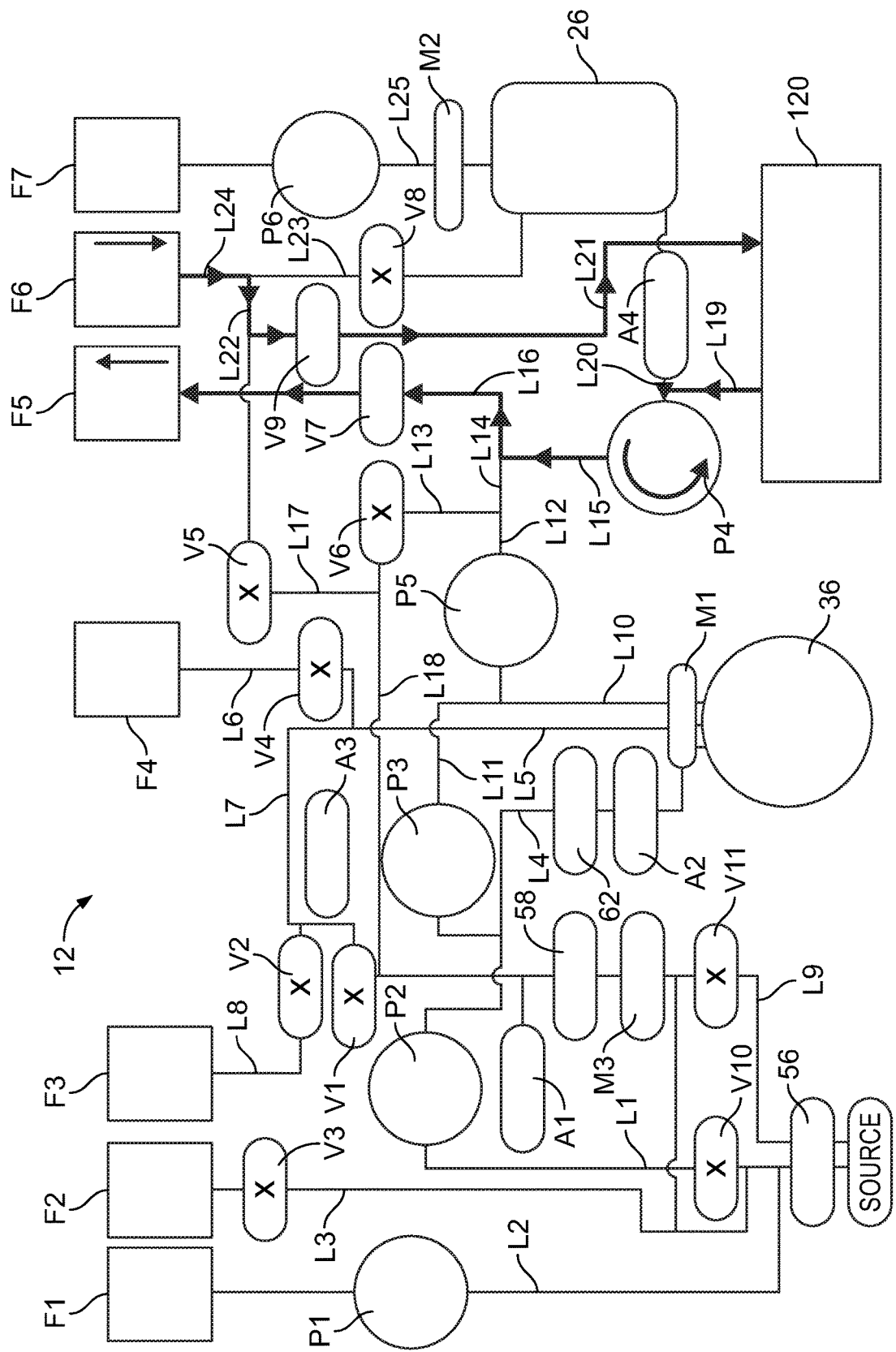

As shown in FIG. 57, the washed MNC product and DNA material are transferred to the dedicated electroporation device 120 from the in-process container F6 by the transfer pump P4 operating in reverse of its direction during the cell washing stage of FIG. 55. The valve V9 associated with valve station C9 is opened, while the valves V5 and V8 associated with valve stations C5 and C8 (respectively) remain closed. This causes the washed MNC product and DNA material to be pulled out of the in-process container F6 via line L24, through lines L22 and L21, and into the dedicated electroporation device 120.

The washed MNC product and DNA material pass through the device 120, where it is subjected to electroporation, which allows for the DNA material to enter into and modify the genome of the T-cells. It will be seen that the flow of fluid through the device 120 is opposite in the electroporation stages of FIG. 53 (in which the MNC product is not washed) and FIG. 57 (in which the MNC product is washed prior to electroporation). In one embodiment, the device 120 is direction independent, such that fluid flowing through it in either direction may be subjected to electroporation. Alternatively, if the device 120 is configured to be direction dependent (i.e., fluid will only be subjected to electroporation upon entering through a designated inlet), different fluid circuits (with opposite orientations of the device 120) may be used depending on whether the MNC product is to be washed before electroporation or not.

The modified MNC product exits the device 120 via line L19. The waste pump P6 downstream of the spinning membrane separator 26 is inactive, along with the plasma pump P5. The valves V6 and V8 associated with valve stations C6 and C8 (respectively) are closed, while the valve V7 associated with valve station C7 is open, which causes the modified MNC product to flow through lines L15 and L16 and into the MNC collection container F5.

In an alternative embodiment, rather than conveying the modified MNC product from the device 120 into the MNC collection container F5, the modified MNC product may instead be conveyed from the device 120 to the source/patient via the fluid flow circuit 12.

4. Reinfusion

With the modified MNC product in the MNC collection container F5, the transfer pump P4 is deactivated and the valves V6 and V11 associated with valve stations C6 and C11 (respectively) are opened (FIG. 58). This allows the modified MNC product to flow out of the MNC collection container F5 via line L16 via gravity and through lines L14 and L13. The modified MNC product continues flowing (via gravity) through lines L18 and L9, to be reinfused to the blood source/patient. The modified MNC product may be retained in the MNC collection container F5 for a holding time prior to reinfusion.

D. Cell Washing Prior to and Following Electroporation

Rather than only washing the MNC product prior to electroporation, it is also within the scope of the present disclosure for the MNC product to be washed prior to electroporation and then again after electroporation. Washing the MNC product following electroporation may be useful for removing any solutions used during electroporation of the MNC product that are not suitable for reinfusion and/or reducing the volume or increasing the concentration of the modified MNC product, for example. Thus, cell washing following electroporation may be advantageous if it is deemed necessary or desirable to achieve one or more of the preceding results (in addition to the results achieved by washing the MNC product before electroporation).

1. Pre-Electroporation Cell Washing

The MNC product may be washed prior to electroporation by the approach shown in FIG. 55 and described above with respect to the procedure in which the MNC product is only washed once. Per the foregoing description, the nature of the waste product filtered from the MNCs and T-cells may vary depending on the configuration of the spinning membrane separator 26.

2. DNA Addition

Following washing, DNA material may be added to the washed MNC product by the approach shown in FIG. 56 and described above with respect to the procedure in which the MNC product is only washed once. Per the foregoing description, the washed MNC product and DNA material may be retained in the in-process container F6 for a holding time prior to the electroporation stage.

3. Electroporation

The washed MNC product and DNA material may be subject to electroporation by the approach shown in FIG. 57 and described above with respect to the procedure in which the MNC product is only washed once. The washed, modified MNC product may be retained in the MNC collection container F5 for a holding time prior to the second washing stage.

4. Post-Electroporation Cell Washing

The washed and modified MNC product flows into the MNC collection container F5 following the electroporation stage. The washed and modified MNC product may then be washed again according to the same approach used for the pre-electroporation washing (i.e., as shown in FIG. 55), with the modified, twice-washed MNC product flowing into the in-process container F6. Washing the modified MNC product may be advantageous in order to remove contaminants, such as suspension media or leftover DNA material that did not enter into a T-cell during the electroporation stage. The modified, twice-washed MNC product may be retained in the in-process container F6 for a holding time prior to reinfusion.

5. Reinfusion

Finally, the modified, twice-washed MNC product may be reinfused to the blood source/patient by the approach shown in FIG. 54 and described above with respect to the procedure in which the MNC product is not washed.

It should be understood that the electroporation-based treatments described herein are merely exemplary and that other electroporation-based treatments are encompassed by the present disclosure. For example, rather than only washing the MNC product prior to electroporation or both before and after electroporation, it is also possible to only wash the MNC product after electroporation, without also washing the MNC product prior to the electroporation stage (e.g., if the benefits of pre-electroporation washing are not required). It should also be understood that cell washing may be carried out in combination with the standalone, multi-functional device 118 of FIGS. 50 and 51, particularly if the device 118 is not configured to wash the MNC product.

ASPECTS

Aspect 1. A fluid processing system, comprising: a separation device; an electroporation device; a pump assembly including a plurality of pumps; and a controller configured to actuate the pump assembly to convey blood from a blood source into the separation device, actuate the separation device to separate a mononuclear cell product from the blood, actuate the pump assembly to convey at least a portion of the mononuclear cell product into the electroporation device to modify a genome of at least one of the cells of the mononuclear cell product, and actuate the pump assembly to convey at least a portion of the modified mononuclear cell product to the blood source.

Aspect 2. The fluid processing system of Aspect 1, wherein the separation device comprises a centrifuge.

Aspect 3. The fluid processing system of any one of the preceding Aspects, further comprising a second separation device configured to be actuated by the controller to wash the mononuclear cell product and/or the modified mononuclear cell product.

Aspect 4. The fluid processing system of Aspect 3, wherein the controller is configured to actuate the second separation device to wash the mononuclear cell product prior to actuating the pump assembly to convey said at least a portion of the mononuclear cell product into the electroporation device.

Aspect 5. The fluid processing system of Aspect 3, wherein the controller is configured to actuate the second separation device to wash the modified mononuclear cell product after actuating the pump assembly to convey said at least a portion of the mononuclear cell product into the electroporation device.

Aspect 6. The fluid processing system of Aspect 3, wherein the controller is configured to actuate the second separation device to wash the mononuclear cell product prior to actuating the pump assembly to convey said at least a portion of the mononuclear cell product into the electroporation device and to actuate the second separation device to wash the modified mononuclear cell product after actuating the pump assembly to convey said at least a portion of the mononuclear cell product into the electroporation device.

Aspect 7. The fluid processing system of any one of the preceding Aspects, wherein the controller is configured to actuate the pump assembly to collect and retain the modified mononuclear cell product for a holding time prior to conveying said at least a portion of the modified mononuclear cell product to the blood source.

Aspect 8. The fluid processing system of any one of Aspects 1-4, wherein the controller is configured to actuate the pump assembly to convey said at least a portion of the modified mononuclear cell product to the blood source without first collecting and retaining the modified cell product for a holding time.

Aspect 9. The fluid processing system of any one of the preceding Aspects, wherein the electroporation device is configured to execute multiple steps of an electroporation-based procedure, including addition of DNA material to the mononuclear cell product and electroporation.

Aspect 10. The fluid processing system of any one of Aspects 1-8, wherein the electroporation device is configured to subject the mononuclear cell product to electroporation, but not configured to add DNA material to the mononuclear cell product.

Aspect 11. A method for processing blood, comprising: drawing blood from a blood source into a fluid flow circuit; separating a mononuclear cell product from the blood; conveying at least a portion of the mononuclear cell product into an electroporation device without disconnecting the blood source from the fluid flow circuit to modify a genome of at least one of the cells of the mononuclear cell product; and returning at least a portion of the modified mononuclear cell product to the blood source.

Aspect 12. The method of Aspect 11, wherein the mononuclear cell product is separated from the blood by centrifugation.

Aspect 13. The method of any one of Aspects 11-12, further comprising washing the mononuclear cell product prior to said at least a portion of the mononuclear cell product being conveyed into the electroporation device.

Aspect 14. The method of any one of Aspects 11-12, further comprising washing the modified mononuclear cell product after said at least a portion of the mononuclear cell product is conveyed into the electroporation device.

Aspect 15. The method of any one of Aspects 11-12, further comprising washing the mononuclear cell product prior to said at least a portion of the mononuclear cell product being conveyed into the electroporation device, and washing the modified mononuclear cell product after actuating the pump assembly to convey said at least a portion of the mononuclear cell product into the electroporation device.

Aspect 16. The method of any one of Aspects 11-15, further comprising collecting and retaining the modified mononuclear cell product for a holding time prior to returning said at least a portion of the modified mononuclear cell product to the blood source.

Aspect 17. The method of any one of Aspects 11-13, wherein said at least a portion of the modified mononuclear cell product is returned to the blood source without first collecting and retaining the modified cell product for a holding time.

Aspect 18. The method of any one of Aspects 11-17, wherein the electroporation device is configured to execute multiple steps of an electroporation-based procedure, including addition of DNA material to the mononuclear cell product and electroporation.

Aspect 19. The method of any one of Aspects 11-17, further comprising manually adding DNA material to the mononuclear cell product prior to said at least a portion of the mononuclear cell product being conveyed into the electroporation device.

Aspect 20. The method of any one of Aspects 11-17, further comprising automatically adding DNA material to the mononuclear cell product prior to said at least a portion of the mononuclear cell product being conveyed into the electroporation device.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing system, comprising:
a first separation device configured to separate mononuclear cells and T-cell lymphocytes from blood;
a second separation device that is separate from the first separation device;
an electroporation device;
a pump assembly including a plurality of pumps; and
a controller configured to execute a mononuclear cell processing procedure to
actuate the pump assembly to convey blood from a blood source into the first separation device,
actuate the first separation device to separate mononuclear cells and T-cell lymphocytes from the blood as a mononuclear cell product,
actuate the pump assembly to convey at least a portion of the mononuclear cell product into the electroporation device to modify a genome of at least one of the cells of the mononuclear cell product so as to create a modified mononuclear cell product, and
actuate the pump assembly to convey at least a portion of the modified mononuclear cell product to the blood source, wherein
the second separation device is configured to wash the mononuclear cell product and to wash the modified mononuclear cell product, and
the controller is configured to selectively control the second separation device during a first version of the mononuclear cell processing procedure to wash the mononuclear cell product, to control the second separation device during a second version of the mononuclear cell processing procedure to wash the modified mononuclear cell product, and to control the second separation device during a third version of the mononuclear cell processing procedure to wash neither the mononuclear cell product nor the modified mononuclear cell product.

2. The fluid processing system of claim 1, wherein the first separation device comprises a centrifuge.

3. The fluid processing system of claim 1, wherein the controller is configured to actuate the second separation device to wash the mononuclear cell product prior to actuating the pump assembly to convey said at least a portion of the mononuclear cell product into the electroporation device and to actuate the second separation device to wash the modified mononuclear cell product after actuating the pump assembly to convey said at least a portion of the mononuclear cell product into the electroporation device.

4. The fluid processing system of claim 1, wherein the controller is configured to actuate the pump assembly to collect and retain the modified mononuclear cell product for a holding time prior to conveying said at least a portion of the modified mononuclear cell product to the blood source.

5. The fluid processing system of claim 1, wherein the controller is configured to actuate the pump assembly to convey said at least a portion of the modified mononuclear cell product to the blood source without first collecting and retaining the modified cell product for a holding time.

6. The fluid processing system of claim 1, wherein the electroporation device is configured to execute multiple steps of an electroporation-based procedure, including addition of DNA material to the mononuclear cell product and electroporation.

7. The fluid processing system of claim 1, wherein the electroporation device is configured to subject the mononuclear cell product to electroporation, but not configured to add DNA material to the mononuclear cell product.

8. The fluid processing system of claim 7, wherein the controller is configured to actuate the pump assembly to add DNA material to the mononuclear cell product.

9. The fluid processing system of claim 8, wherein the controller is configured to control the pump assembly to retain the mixture of the DNA material and the mononuclear cell product for a holding time prior to actuating the pump assembly to convey said at least a portion of the mononuclear cell product into the electroporation device.

10. The fluid processing system of claim 1, wherein the second separation device comprises a spinning membrane separator drive unit.

11. The fluid processing system of claim 1, further comprising an outlet sensor associated with the second separation device and configured to detect optical characteristics of a waste product exiting the second separation device.

* * * * *